(12) United States Patent
McAuley et al.

(10) Patent No.: US 11,554,234 B2
(45) Date of Patent: Jan. 17, 2023

(54) BREATHING ASSISTANCE APPARATUS

(71) Applicant: Fisher & Paykel Healthcare Limited, Auckland (NZ)

(72) Inventors: Alastair Edwin McAuley, Auckland (NZ); Gregory James Olsen, Auckland (NZ); Kamman Law, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/714,853

(22) Filed: Apr. 6, 2022

(65) Prior Publication Data

US 2022/0226596 A1 Jul. 21, 2022

Related U.S. Application Data

(63) Continuation of application No. 17/303,892, filed on Jun. 9, 2021, which is a continuation of application
(Continued)

(51) Int. Cl.
*A61M 16/06* (2006.01)
*A61M 16/10* (2006.01)
(Continued)

(52) U.S. Cl.
CPC .... *A61M 16/0616* (2014.02); *A61M 16/0069* (2014.02); *A61M 16/024* (2017.08);
(Continued)

(58) Field of Classification Search
CPC .......... A61M 16/0605; A61M 16/0611; A61M 16/0616; A61M 16/0622; A61M 16/0627;
(Continued)

(56) References Cited

U.S. PATENT DOCUMENTS

| 301,111 | A | 7/1884 | Genese |
| 472,238 | A | 4/1892 | Van Orden |

(Continued)

FOREIGN PATENT DOCUMENTS

| AU | 2009321054 | 7/2015 |
| CA | 1311662 | 12/1992 |

(Continued)

OTHER PUBLICATIONS

U.S. Appl. No. 60/493,515, filed Aug. 8, 2002, Sleeper et al.
(Continued)

*Primary Examiner* — LaToya M Louis
(74) *Attorney, Agent, or Firm* — Knobbe, Martens, Olson & Bear LLP

(57) ABSTRACT

A breathing assistance apparatus is disclosed, for use with delivery of respiratory gases to a patient. The breathing assistance apparatus includes a patient interface, having a body section adapted to cover the nose, or nose and mouth of a patient and a sealing interface. The sealing interface includes at least an outer sealing member. The outer sealing member is adapted to attach to the body section in a sealing manner and has a substantially thin section in at least its nasal bridge region. The thin section is substantially thinner than the rest of the outer sealing member. The patient interface comprises a mask body and a seal assembly. The seal assembly includes a flexible seal, and a rigid seal clip, the seal assembly being removably attached to the mask body via the rigid seal clip. The mask body and rigid seal clip are profiled to match the contours of a user's face so that the seal has a substantially constant wall depth.

23 Claims, 37 Drawing Sheets

Related U.S. Application Data

No. 14/792,399, filed on Jul. 6, 2015, now abandoned, which is a continuation of application No. 12/502,528, filed on Jul. 14, 2009, now Pat. No. 9,072,852.

(60) Provisional application No. 61/082,007, filed on Jul. 18, 2008, provisional application No. 61/082,974, filed on Jul. 23, 2008, provisional application No. 61/083,554, filed on Jul. 25, 2008.

(51) Int. Cl.
*A61M 16/16* (2006.01)
*A61M 16/08* (2006.01)
*A61M 16/00* (2006.01)

(52) U.S. Cl.
CPC ........ *A61M 16/06* (2013.01); *A61M 16/0622* (2014.02); *A61M 16/0633* (2014.02); *A61M 16/0683* (2013.01); *A61M 16/0825* (2014.02); *A61M 16/10* (2013.01); *A61M 16/109* (2014.02); *A61M 16/1075* (2013.01); *A61M 16/16* (2013.01); *A61M 16/0816* (2013.01); *A61M 2016/0027* (2013.01); *A61M 2205/3368* (2013.01)

(58) Field of Classification Search
CPC .......... A61M 16/0633; A61M 16/0638; A61M 16/0644; A61M 16/065; A61M 16/0655
See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,635,545 A | 7/1927 | Drager |
| 2,126,755 A | 8/1938 | Dreyfus |
| 2,228,218 A | 1/1941 | Schwartz |
| 2,241,535 A | 5/1941 | Boothby et al. |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,452,845 A | 11/1948 | Fisher |
| 2,508,050 A | 5/1950 | Valente |
| 2,684,066 A | 7/1954 | Glidden |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 2,875,759 A | 3/1959 | Galleher |
| 2,894,506 A | 7/1959 | Rose |
| 2,939,458 A | 6/1960 | Lundquist |
| 3,424,633 A | 1/1969 | Corrigall et al. |
| 3,490,452 A | 1/1970 | Greenfield |
| 3,599,635 A | 8/1971 | Kenneth |
| 3,682,171 A | 8/1972 | Dali et al. |
| 3,834,682 A | 9/1974 | McPhee |
| 3,850,171 A | 11/1974 | Ball et al. |
| 3,894,562 A | 7/1975 | Moseley et al. |
| 3,972,321 A | 8/1976 | Proctor |
| 3,977,432 A | 8/1976 | Vidal |
| 3,992,720 A | 11/1976 | Nicolinas |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| 4,150,464 A | 4/1979 | Tracy |
| D252,322 S | 7/1979 | Johnson |
| 4,201,205 A | 5/1980 | Bartholomew |
| 4,258,710 A | 3/1981 | Reber |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Warncke et al. |
| 4,437,462 A | 3/1984 | Piljay |
| 4,454,880 A | 6/1984 | Muto et al. |
| 4,574,799 A | 3/1986 | Warncke et al. |
| 4,603,602 A | 8/1986 | Montesi |
| 4,621,632 A | 11/1986 | Bartels et al. |
| 4,644,974 A | 2/1987 | Zingg |
| 4,676,241 A | 6/1987 | Webb et al. |
| D293,613 S | 1/1988 | Wingler |
| 4,753,233 A | 6/1988 | Grimes |
| 4,782,832 A | 11/1988 | Trimble et al. |
| 4,803,981 A | 2/1989 | Vickery |
| 4,804,160 A | 2/1989 | Harbeke |
| 4,836,200 A | 6/1989 | Clark et al. |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| D310,431 S | 9/1990 | Bellm |
| 4,958,658 A | 9/1990 | Zajac |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| D320,677 S | 10/1991 | Kumagai et al. |
| D321,419 S | 11/1991 | Wallace |
| 5,062,421 A | 11/1991 | Burns et al. |
| 5,065,756 A | 11/1991 | Rapoport |
| D322,318 S | 12/1991 | Sullivan et al. |
| 5,074,297 A | 12/1991 | Venegas |
| 5,094,236 A | 3/1992 | Tayebi |
| 5,113,857 A | 5/1992 | Dickerman et al. |
| 5,121,745 A | 6/1992 | Israel et al. |
| 5,148,802 A | 9/1992 | Sanders et al. |
| 5,164,652 A | 11/1992 | Johnson et al. |
| 5,231,979 A | 8/1993 | Rose |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,267,556 A | 12/1993 | Feng |
| 5,269,296 A | 12/1993 | Landis et al. |
| 5,315,859 A | 5/1994 | Schommer |
| 5,349,949 A | 9/1994 | Schegerin |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,979 A | 8/1995 | Johnson et al. |
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,460,174 A | 10/1995 | Chang |
| 5,461,932 A | 10/1995 | Hall |
| 5,477,852 A | 12/1995 | Landis et al. |
| 5,513,634 A | 5/1996 | Jackson |
| 5,518,802 A | 5/1996 | Colvin et al. |
| 5,533,506 A | 7/1996 | Wood |
| 5,540,223 A | 7/1996 | Starr et al. |
| 5,542,128 A | 8/1996 | Lomas |
| 5,551,419 A | 9/1996 | Froehlich et al. |
| 5,558,090 A | 9/1996 | James |
| 5,560,354 A | 10/1996 | Berthon-Jones et al. |
| 5,570,689 A | 11/1996 | Starr et al. |
| 5,588,423 A | 12/1996 | Smith |
| 5,595,174 A | 1/1997 | Gwaltney |
| 5,601,078 A | 2/1997 | Schaller et al. |

(56) References Cited

U.S. PATENT DOCUMENTS

| | | |
|---|---|---|
| D378,610 S | 3/1997 | Reischel et al. |
| 5,649,532 A | 7/1997 | Griffiths |
| 5,657,752 A | 8/1997 | Landis et al. |
| 5,662,101 A | 9/1997 | Ogden et al. |
| 5,664,566 A | 9/1997 | Mcdonald et al. |
| 5,687,715 A | 11/1997 | Landis |
| 5,690,097 A | 11/1997 | Howard et al. |
| 5,724,677 A | 3/1998 | Bryant et al. |
| 5,724,965 A | 3/1998 | Handke et al. |
| 5,746,201 A | 5/1998 | Kidd |
| 5,752,510 A | 5/1998 | Goldstein |
| 5,755,578 A | 5/1998 | Contant et al. |
| 5,789,660 A | 8/1998 | Kofoed et al. |
| 5,806,727 A | 9/1998 | Joseph |
| 5,807,295 A | 9/1998 | Hutcheon et al. |
| 5,857,460 A | 1/1999 | Popitz |
| 5,884,624 A | 3/1999 | Barnett et al. |
| 5,904,278 A | 5/1999 | Barlow et al. |
| 5,918,598 A | 7/1999 | Belfer |
| 5,921,239 A | 7/1999 | McCall et al. |
| 5,924,420 A | 7/1999 | Reischel |
| 5,941,245 A | 8/1999 | Hannah et al. |
| 5,943,473 A | 8/1999 | Levine |
| 5,953,763 A | 9/1999 | Gouget |
| 5,966,745 A | 10/1999 | Schwartz et al. |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,135,109 A | 10/2000 | Blasdell et al. |
| 6,135,432 A | 10/2000 | Hebblewhite et al. |
| 6,192,886 B1 | 2/2001 | Rudolph |
| D440,302 S | 4/2001 | Wolfe |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| D455,891 S | 4/2002 | Biedrzycki |
| 6,398,197 B1 | 6/2002 | Dickinson et al. |
| 6,412,487 B1 | 7/2002 | Gunaratnam et al. |
| 6,412,488 B1 | 7/2002 | Barnett |
| 6,418,928 B1 | 7/2002 | Bordewick et al. |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,526,978 B2 | 3/2003 | Dominguez |
| 6,530,373 B1 | 3/2003 | Patron et al. |
| 6,561,188 B1 | 5/2003 | Ellis |
| 6,561,190 B1 | 5/2003 | Kwok |
| 6,561,191 B1 | 5/2003 | Kwok |
| 6,571,798 B1 | 6/2003 | Thornton |
| 6,581,594 B1 | 6/2003 | Drew et al. |
| 6,581,601 B2 | 6/2003 | Ziaee |
| 6,581,602 B2 | 6/2003 | Kwok et al. |
| 6,584,977 B1 | 7/2003 | Serowski |
| 6,588,424 B2 | 7/2003 | Bardel |
| 6,615,832 B1 | 9/2003 | Chen |
| 6,629,531 B2 | 10/2003 | Gleason et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| D485,905 S | 1/2004 | Moore |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,736,139 B1 | 5/2004 | Wix |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,997,187 B2 | 2/2006 | Wood et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,051,765 B1 | 5/2006 | Kelley et al. |
| 7,066,179 B2 | 6/2006 | Eaton et al. |
| 7,077,126 B2 | 7/2006 | Kummer et al. |
| D526,094 S | 8/2006 | Chen |
| 7,096,864 B1 | 8/2006 | Mayer et al. |
| D533,269 S | 12/2006 | McAuley et al. |
| 7,178,525 B2 | 2/2007 | Matula, Jr. et al. |
| 7,178,528 B2 | 2/2007 | Lau |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,261,104 B2 | 8/2007 | Keifer |
| 7,287,528 B2 | 10/2007 | Ho et al. |
| 7,290,546 B2 | 11/2007 | Sprinkle et al. |
| 7,296,575 B1 | 11/2007 | Radney |
| 7,318,437 B2 | 1/2008 | Gunaratnam et al. |
| 7,353,827 B2 | 4/2008 | Geist |
| 7,357,136 B2 | 4/2008 | Ho et al. |
| 7,406,966 B2 | 8/2008 | Wondka |
| 7,448,386 B2 | 11/2008 | Ho et al. |
| 7,487,772 B2 | 2/2009 | Ging et al. |
| 7,493,902 B2 | 2/2009 | White et al. |
| D589,139 S | 3/2009 | Guney |
| 7,523,754 B2 | 4/2009 | Lithgow et al. |
| D595,841 S | 7/2009 | McAuley et al. |
| 7,562,658 B2 | 7/2009 | Madaus et al. |
| 7,597,100 B2 | 10/2009 | Ging |
| 7,640,934 B2 | 1/2010 | Zollinger et al. |
| 7,647,926 B2 | 1/2010 | Gerder et al. |
| 7,658,189 B2 | 2/2010 | Davidson et al. |
| 7,665,464 B2 | 2/2010 | Kopacko et al. |
| D612,933 S | 3/2010 | Prentice |
| 7,681,575 B2 | 3/2010 | Wixey et al. |
| 7,694,677 B2 | 4/2010 | Tang |
| 7,703,457 B2 | 4/2010 | Barnett et al. |
| 7,708,017 B2 | 5/2010 | Davidson |
| 7,753,051 B2 | 7/2010 | Burrow et al. |
| D623,288 S | 9/2010 | Lubke |
| 7,814,911 B2 | 10/2010 | Bordewick et al. |
| 7,827,990 B1 | 11/2010 | Melidis et al. |
| 7,856,982 B2 | 12/2010 | Matula et al. |
| 7,877,817 B1 | 2/2011 | Ho |
| 7,896,003 B2 | 3/2011 | Matula et al. |
| 7,931,024 B2 | 4/2011 | Ho et al. |

(56) References Cited

U.S. PATENT DOCUMENTS

| | | |
|---|---|---|
| 7,934,501 B2 | 5/2011 | Fu |
| 7,942,150 B2 | 5/2011 | Guney et al. |
| 7,992,560 B2 | 8/2011 | Burton et al. |
| 8,042,539 B2 | 10/2011 | Chandran et al. |
| 8,042,541 B2 | 10/2011 | Amarasinghe et al. |
| 8,109,271 B2 | 2/2012 | Vandine et al. |
| 8,136,524 B2 | 3/2012 | Ging et al. |
| 8,136,525 B2 | 3/2012 | Lubke et al. |
| 8,171,933 B2 | 5/2012 | Xue et al. |
| D661,796 S | 6/2012 | Andrews et al. |
| 8,245,711 B2 | 8/2012 | Matula et al. |
| 8,371,302 B2 | 2/2013 | Ging et al. |
| 8,397,727 B2 | 3/2013 | Ng et al. |
| 8,443,807 B2 | 5/2013 | McAuley et al. |
| D686,313 S | 7/2013 | Matula et al. |
| 8,479,726 B2 | 7/2013 | McAuley |
| 8,479,741 B2 | 7/2013 | McAuley et al. |
| 8,567,404 B2 | 10/2013 | Davidson et al. |
| 8,631,793 B2 | 1/2014 | Omura et al. |
| 8,631,799 B2 | 1/2014 | Davenport |
| 8,636,005 B2 | 1/2014 | Gradon et al. |
| 8,701,667 B1 | 4/2014 | Ho et al. |
| 8,714,157 B2 | 5/2014 | McAuley et al. |
| 8,720,444 B2 | 5/2014 | Chang |
| 8,757,157 B2 | 6/2014 | Price et al. |
| 8,783,257 B2 | 7/2014 | McAuley et al. |
| 8,869,797 B2 | 10/2014 | Davidson et al. |
| 8,869,798 B2 | 10/2014 | Wells et al. |
| 8,875,709 B2 | 11/2014 | Davidson et al. |
| 8,944,061 B2 | 2/2015 | D'Souza et al. |
| 8,950,404 B2 | 2/2015 | Formica et al. |
| 8,960,196 B2 | 2/2015 | Henry |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,072,852 B2 | 7/2015 | McAuley et al. |
| 9,095,673 B2 | 8/2015 | Barlow et al. |
| 9,119,929 B2 | 9/2015 | McAuley et al. |
| 9,119,931 B2 | 9/2015 | D'Souza et al. |
| 9,138,555 B2 | 9/2015 | McAuley et al. |
| 9,149,596 B2 | 10/2015 | Valcic et al. |
| 9,186,474 B1 | 11/2015 | Rollins |
| 9,242,062 B2 | 1/2016 | Melidis et al. |
| 9,292,799 B2 | 3/2016 | McAuley et al. |
| 9,295,799 B2 | 3/2016 | McAuley et al. |
| 9,302,065 B2 | 4/2016 | Smith et al. |
| 9,320,566 B1 | 4/2016 | Alston, Jr. |
| 9,320,866 B2 | 4/2016 | McAuley et al. |
| 9,333,315 B2 | 5/2016 | McAuley et al. |
| 9,339,624 B2 | 5/2016 | McAuley |
| 9,339,662 B2 | 5/2016 | McAuley et al. |
| 9,375,545 B2 | 6/2016 | Darkin et al. |
| 9,381,316 B2 | 7/2016 | Ng et al. |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 | 2/2017 | McAuley et al. |
| 9,561,339 B2 | 2/2017 | McAuley et al. |
| 9,744,385 B2 | 8/2017 | Henry et al. |
| 9,884,160 B2 | 2/2018 | McAuley et al. |
| 9,901,699 B2 | 2/2018 | Veliss et al. |
| 9,901,700 B2 | 2/2018 | McAuley et al. |
| 9,907,925 B2 | 3/2018 | McAuley et al. |
| 9,974,914 B2 | 5/2018 | McAuley |
| 10,080,856 B2 | 9/2018 | McLaren et al. |
| 10,137,271 B2 | 11/2018 | McAuley et al. |
| 10,201,678 B2 | 2/2019 | Guney et al. |
| 10,252,015 B2 | 4/2019 | McAuley et al. |
| 10,258,756 B2 | 4/2019 | Mainusch et al. |
| 10,258,757 B2 | 4/2019 | Allan et al. |
| 10,272,218 B2 | 4/2019 | McAuley et al. |
| 10,328,226 B2 | 6/2019 | Allan et al. |
| 10,363,387 B2 | 7/2019 | Allan et al. |
| 10,384,029 B2 | 8/2019 | McAuley et al. |
| 10,413,694 B2 | 9/2019 | Allan et al. |
| 10,463,825 B2 | 11/2019 | McAuley et al. |
| 10,742,451 B2 | 8/2020 | Allan et al. |
| 10,821,251 B2 | 11/2020 | McAuley et al. |
| 10,835,702 B2 | 11/2020 | McAuley et al. |
| 10,842,964 B2 | 11/2020 | McAuley et al. |
| 10,980,962 B2 | 4/2021 | McAuley et al. |
| 11,179,535 B2 | 11/2021 | McAuley et al. |
| 11,247,013 B2 | 2/2022 | McAuley et al. |
| 11,260,194 B2 | 3/2022 | McAuley et al. |
| 11,291,790 B2 | 4/2022 | McAuley et al. |
| 2001/0017134 A1 | 8/2001 | Bahr |
| 2001/0020474 A1 | 9/2001 | Hecker et al. |
| 2001/0029952 A1 | 10/2001 | Curran |
| 2002/0005198 A1 | 1/2002 | Kwok et al. |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0039867 A1 | 4/2002 | Curro et al. |
| 2002/0046755 A1 | 4/2002 | Voss |
| 2002/0053347 A1 | 5/2002 | Ziaee |
| 2002/0059935 A1 | 5/2002 | Wood |
| 2002/0069467 A1 | 6/2002 | Immediato et al. |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0075180 A1 | 4/2003 | Raje |
| 2003/0075182 A1 | 4/2003 | Heidmann et al. |
| 2003/0079749 A1 | 5/2003 | Strickland et al. |
| 2003/0084996 A1 | 5/2003 | Alberg et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0011087 A1 | 1/2004 | Rebouillat et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0092999 A1 | 5/2004 | Lojewski |
| 2004/0094157 A1 | 5/2004 | Dantanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118212 A1 | 6/2004 | Orr et al. |
| 2004/0118406 A1 | 6/2004 | Lithgow |
| 2004/0118412 A1 | 6/2004 | Piletti-Reyes |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2004/0261797 A1 | 12/2004 | White et al. |

(56) References Cited

U.S. PATENT DOCUMENTS

| | | |
|---|---|---|
| 2005/0011521 A1 | 1/2005 | Sprinkle et al. |
| 2005/0011524 A1 | 1/2005 | Thomlinson et al. |
| 2005/0016532 A1 | 1/2005 | Farrell |
| 2005/0028822 A1 | 2/2005 | Sleeper et al. |
| 2005/0028833 A1 | 2/2005 | Vena et al. |
| 2005/0033247 A1 | 2/2005 | Thompson |
| 2005/0045182 A1 | 3/2005 | Wood et al. |
| 2005/0051171 A1 | 3/2005 | Booth |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0172969 A1 | 8/2005 | Ging |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0054169 A1 | 3/2006 | Han et al. |
| 2006/0060200 A1 | 3/2006 | Ho et al. |
| 2006/0076019 A1 | 4/2006 | Ho |
| 2006/0081250 A1 | 4/2006 | Bordewick et al. |
| 2006/0081256 A1 | 4/2006 | Palmer |
| 2006/0096598 A1 | 5/2006 | Ho et al. |
| 2006/0102185 A1 | 5/2006 | Drew et al. |
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0196511 A1 | 9/2006 | Lau et al. |
| 2006/0201514 A1 | 9/2006 | Jones et al. |
| 2006/0207599 A1 | 9/2006 | Busch |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283458 A1 | 12/2006 | Woodard |
| 2006/0283459 A1 | 12/2006 | Geiselhart et al. |
| 2006/0283461 A1 | 12/2006 | Lubke et al. |
| 2007/0006492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163594 A1 | 7/2007 | Ho et al. |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0272249 A1 | 11/2007 | Chandran |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0053450 A1 | 3/2008 | Van Kerkwyk et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0083412 A1 | 4/2008 | Henry et al. |
| 2008/0092905 A1 | 4/2008 | Gunaratnam |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0135050 A1 | 6/2008 | Hitchcock et al. |
| 2008/0142019 A1 | 6/2008 | Lewis |
| 2008/0149104 A1 | 6/2008 | Eifler |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0236586 A1 | 10/2008 | Mcdonald et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0314390 A1 | 12/2008 | Kwok et al. |
| 2008/0319334 A1 | 12/2008 | Yamamori |
| 2009/0014007 A1 | 1/2009 | Brambilla et al. |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0183734 A1 | 7/2009 | Kwok et al. |
| 2009/0183739 A1 | 7/2009 | Wondka |
| 2009/0211583 A1 | 8/2009 | Carroll et al. |
| 2009/0223519 A1 | 9/2009 | Eifler et al. |
| 2009/0320842 A1 | 12/2009 | Doherty |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0051031 A1 | 3/2010 | Lustenberger et al. |
| 2010/0051034 A1 | 3/2010 | Howard |
| 2010/0083969 A1 | 4/2010 | Crumblin |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0067704 A1 | 3/2011 | Kooij |
| 2011/0072553 A1 | 3/2011 | Ho |
| 2011/0088699 A1 | 4/2011 | Skipper |
| 2011/0126838 A1 | 6/2011 | Alberici |
| 2011/0162654 A1 | 7/2011 | Carroll et al. |
| 2011/0232649 A1 | 9/2011 | Collazo et al. |
| 2011/0259337 A1 | 10/2011 | Hitchcock et al. |
| 2011/0265796 A1 | 11/2011 | Amarasinghe et al. |

(56) References Cited

U.S. PATENT DOCUMENTS

| | | |
|---|---|---|
| 2011/0290253 A1 | 12/2011 | McAuley |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318265 A1 | 12/2012 | Amirav et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0261432 A1 | 9/2014 | Eves et al. |
| 2014/0311492 A1 | 10/2014 | Stuebiger et al. |
| 2014/0338672 A1 | 11/2014 | D'Souza et al. |
| 2015/0033457 A1 | 2/2015 | Tryner et al. |
| 2015/0090266 A1 | 4/2015 | Melidis et al. |
| 2015/0246198 A1 | 9/2015 | Bearne et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0038707 A1 | 2/2016 | Allan et al. |
| 2016/0051786 A1 | 2/2016 | McAuley et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2017/0246411 A1 | 8/2017 | Mashal et al. |
| 2017/0296770 A1 | 10/2017 | Gunaratnam et al. |
| 2017/0304574 A1 | 10/2017 | McAuley et al. |
| 2017/0368288 A1 | 12/2017 | Stephens et al. |
| 2018/0250483 A1 | 9/2018 | Olsen et al. |
| 2018/0256844 A1 | 9/2018 | Galgali et al. |
| 2019/0001095 A1 | 1/2019 | Rose et al. |
| 2019/0232010 A1 | 8/2019 | McAuley et al. |
| 2020/0046928 A1 | 3/2020 | Allan |
| 2020/0108219 A1 | 4/2020 | McAuley et al. |
| 2020/0171260 A1 | 6/2020 | McLaren |
| 2020/0197644 A1 | 6/2020 | McAuley et al. |
| 2021/0228829 A1 | 7/2021 | McAuley et al. |
| 2021/0386951 A1 | 12/2021 | McAuley et al. |
| 2021/0402121 A1 | 12/2021 | McAuley et al. |
| 2022/0105294 A1 | 4/2022 | McAuley et al. |

FOREIGN PATENT DOCUMENTS

| | | |
|---|---|---|
| CA | 2648690 | 11/2007 |
| CD | 000966064-0001 | 9/2008 |
| CD | 000966064-0002 | 9/2008 |
| CD | 000966064-0003 | 9/2008 |
| CD | 000966064-0004 | 9/2008 |
| CD | 000966064-0017 | 9/2008 |
| CN | 2172538 | 7/1994 |
| CN | 1780265 | 12/2005 |
| CN | 1784250 | 6/2006 |
| CN | 1901961 | 1/2007 |
| DE | 895692 | 11/1953 |
| DE | 29723101 U1 | 7/1998 |
| DE | 19603949 | 11/1998 |
| DE | 102006011151 | 4/2006 |
| DE | 102006011151 | 9/2007 |
| EP | 0 350 322 | 1/1990 |
| EP | 0 427 474 | 5/1991 |
| EP | 0 462 701 | 12/1991 |
| EP | 0 747 078 | 12/1996 |
| EP | 1 099 452 | 5/2001 |
| EP | 0 830 180 | 3/2002 |
| EP | 1 258 266 | 11/2002 |
| EP | 1 488 820 | 12/2004 |
| EP | 1 582 231 | 10/2005 |
| EP | 2 042 209 | 4/2009 |
| EP | 2 130 563 | 12/2009 |
| EP | 2 145 645 | 1/2010 |
| EP | 1 753 495 | 9/2010 |
| EP | 1 481 702 | 9/2012 |
| EP | 2 749 176 | 7/2014 |
| EP | 1 646 910 | 8/2015 |
| EP | 2 022 528 | 3/2016 |
| EP | 2 451 518 | 10/2017 |
| FR | 2658725 | 8/1991 |
| FR | 2749176 | 12/1997 |
| GB | 190224431 | 12/1902 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2186801 | 8/1987 |
| GB | 2385533 | 8/2003 |
| JP | 62-024721 | 2/1987 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| WO | WO 82/003548 | 10/1982 |
| WO | WO 97/32494 | 9/1997 |
| WO | WO 98/04310 | 2/1998 |
| WO | WO 98/004310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/74509 | 12/2000 |
| WO | WO 00/074758 | 12/2000 |
| WO | WO 00/078384 | 12/2000 |
| WO | WO 01/00266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/94721 | 12/2001 |
| WO | WO 01/097892 | 12/2001 |
| WO | WO 01/97892 | 12/2001 |
| WO | WO 01/097893 | 12/2001 |
| WO | WO 02/005883 | 1/2002 |
| WO | WO 02/011804 | 2/2002 |
| WO | WO 02/047749 | 6/2002 |
| WO | WO 02/074372 | 9/2002 |
| WO | WO 03/035156 | 5/2003 |
| WO | WO 03/076020 | 9/2003 |
| WO | WO 03/082406 | 10/2003 |
| WO | WO 03/092755 | 11/2003 |
| WO | WO 04/007010 | 1/2004 |
| WO | WO 04/096332 | 1/2004 |
| WO | WO 04/012803 | 2/2004 |
| WO | WO 04/022146 | 3/2004 |
| WO | WO 04/022147 | 3/2004 |
| WO | WO 04/030736 | 4/2004 |
| WO | WO 04/041341 | 5/2004 |
| WO | WO 04/041342 | 5/2004 |
| WO | WO 04/052438 | 6/2004 |
| WO | WO 04/071565 | 8/2004 |

(56) References Cited

FOREIGN PATENT DOCUMENTS

| | | |
|---|---|---|
| WO | WO 04/073777 | 9/2004 |
| WO | WO 04/073778 | 9/2004 |
| WO | WO 04/079066 | 9/2004 |
| WO | WO 05/010608 | 2/2005 |
| WO | WO 05/016403 | 2/2005 |
| WO | WO 05/018523 | 3/2005 |
| WO | WO 05/021075 | 3/2005 |
| WO | WO 05/051468 | 6/2005 |
| WO | WO 05/063326 | 7/2005 |
| WO | WO 05/063328 | 7/2005 |
| WO | WO 05/076874 | 8/2005 |
| WO | WO 05/079726 | 9/2005 |
| WO | WO 05/086943 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/053878 | 5/2007 |
| WO | WO 07/114492 | 10/2007 |
| WO | WO 07/147088 | 12/2007 |
| WO | WO 08/007985 | 1/2008 |
| WO | WO 08/011682 | 1/2008 |
| WO | WO 08/014543 | 2/2008 |
| WO | WO 08/030831 | 3/2008 |
| WO | WO 08/036625 | 3/2008 |
| WO | WO 08/060295 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 10/148453 | 12/2010 |
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

U.S. Appl. No. 60/496,059, filed Aug. 18, 2003, Ho et al.
U.S. Appl. No. 60/529,696, filed Dec. 16, 2003, Lithgow et al.
U.S. Appl. No. 61/064,406, filed Mar. 4, 2008, Wehbeh.
U.S. Appl. No. 61/071,893, filed May 22, 2008, Wehbeh et al.
U.S. Appl. No. 61/136,617, filed Sep. 19, 2008, Wehbeh et al.
Resmed Mirage Swift™ II Nasal Pillows System product page (http://www.resmed.com/en-us/products/masks/mirage_swift_II_nasal_pillows. system/Mirage-Swift-II-Nasal-Pillows-System.html?menu=products); archived Jul. 21, 2008, 2 pp.
Resmed Mirage Swift™ II user brochure (http://www.resmed.com/en us/products/masks/mirage-swift_II_nasal_pillows_system/documents/mirage-swift-ii-np-brochure-patient-english-usa.pdf) copyright 2007, 4 pp.
ResMed Mirage Swift II Fitting guide (http://www;resmed.com/en-us/products/masks/mirage_swift_II_nasal_pillows_system/documents/mirage-swift_ii_np-fitting_English.pdf) copyright 2006, 2 pp.
ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.
ResMed Mirage Swift II user guide (http://www.resmed.com/en-us/products/service_and_support/documents/60593rl_mirage_swiftII_nasal_userglide_us_multi.pdf) copyright 2006, 1 p.
ResMed Mirage Swift II component card (http://www.resmed.com/en-us/products/masks/mirage_swift_II_nasal_pillows_system/documents/mirage-swift-ii-np-cc-usa.pdf); copyright 2006 2 pp.
Resmed Swift™ LT Nasal Pillows System, product page, (http://www.resmed.com/en-us/products/masks/mirage_swift_II_nasal_pillows_system/Mirage-Swift-II-Nasal_Pillows-System.html?menu=products), Jul. 3, 2008, 2 pp.
Resmed Swift LT user brochure, (http://www.resmed.com/en-us/products/masks/mirage_swift_II_nasal_pillows_system/documents/mirage-swift-ii-np-brochure-patient-english-usa.pdf), copyright 2008, 4 pp.
Resmed Swift™ LT component card (http://www.resmed.com/en-us/assets/documents/products/swift_lt/components_card/1012463_swift-lt_components-card_usa_eng.pdf) copyright 2008, 46 pp.
Resmed Swift™ LT fitting guide, (http://www.resmed.com/en-us/assets/documents/product/swift-II/clinical_fact_sheet/1012406 swift-ii_fact-sheet_usa_eng.pdf), 2008, 2 pp.
Resmed Swift™ LT fact sheet (http://www.resmed.com/en-us/assets/documents/product/swift-lt/clinical_fact_sheet/1012406 swiftlt_fact-sheet_usa_eng.pdf, copyright 2008, 4 pp.
Resmed Swift™ LT image gallery (http://www.resmed.com/en-us/products/masks/swift_lt_nasal_pillows_system/imagegallery.html?menu=products, Apr. 25, 2008, 2 pp.
Resmed Swift™ LT interactive fitting guide—screenshot from troubleshooting part (http://www.resmed.com/enus/assets/multimedia/product/swift-lt/flash/swift-lt-fitting-eng.swf), Jul. 3, 2008, 2 pp.
Puritan Bennett Breeze® SleepGear® CPAP Interface, product page (http://puritanbennett.com/prod/product.aspx?id=233); archived Oct. 19, 2007, 2 pp.
Puritan Bennett Breeze® SleepGear® User's Guide (http://puritanbennett.com/_catalog/pdf/dfu/107598a00[I].pdf); copyright 2007, 18 pp.
Puritan Bennett Breeze® SleepGear® sales sheet (http://www.puritanbennett.com/_Catalog/PDF/Product/BreezeSleepGear.pdf) copyright 2016, 7 PP.
Puritan Bennett mask coding matrix (http://www.puritanbennett.com/_Catalog/PDF/Product/BreezeSlpGear(ST03700).pdf copyright 2006, 3 pp.
Puritan Bennett Breeze fitting guide (http://www.puritanbennett.com/_Catalog/PDF/Product/BreezeFittingPoster.pdf, Oct. 19, 2007, 1 p.
Respironics Optilife Pillows mask product page (http://optilife.respironics.com:80/); archived Nov. 21, 2007, 2 pp.

(56) References Cited

OTHER PUBLICATIONS

Respironics Optilife Pillows mask part numbers page (http://optilife.respironics.com:80/Parts.aspx); archived Nov. 23, 2007, 4 pp.
Respironics Optilife Pillows mask FAQ (http://optilife.respironics.com:80/faqs.aspx): archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask filling guide screen shot (http://optilife.respironics.com:80/fittingGuide.aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp.
Puritan Bennett Breeze description; copyright 2000 by Mallinckrodt Inc., 4 pp.
Fisher & Paykel Opus product page, archived Sep. 3, 2009, 2 pp.
Fisher & Paykel Opus patient interface product photographs, Jul. 2007, 6 pp.
Photographs of Opus 360 nasal pillows mask patient instructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2 pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Fisher & Paykel HC200 Series Nasal CPAP Blower & Heated Humidifier User Manual, 17 pp., May 1998.
Fisher & Paykel Healthcare, FlexiFit® 431 Full Face Mask instructions, 2010, 4 pp.
Fisher & Paykel Healthcare, FlexiFit™ 431 Full Face Mask, specification sheet, 2004, 2 pp.
Fisher & Paykel Healthcare, Interface Solutions Product Profile, 2006, 12 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464-7893), 4 pp.
Malloy, 1994, Plastic Part Design for Injection Molding, Hanswer Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri-es-cpap-humidifier-manual.pdf front cover, pp. 3-4 and 6.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
Resmed, Jun. 29, 1997, Mask Frames (Source: Wayback Machine Internet Archive); http://web.archive.org/web/19970629053430/http://www.resmed.com/-/maskframes/mask.htm, 2 pp.
ResMed, Mirage Swift™ Nasal Pillows System from ResMed, product brochure, 2004, 6 pp.
Resmed, Mirage Swift™ Nasal Pillows System: User's Guide, product brochure, 2004,11 pp.
Resmed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.—wedding.sub.—band-s.sub.—metal/48214W.html), 3 pp.
U.S. Appl. No. 61/064,406, 34 pages, copy provided by USPTO, filed Feb. 23, 2009.
U.S. Appl. No. 61/071,893, 43 pages, copy provided by USPTO, filed Feb. 23, 2009.
U.S. Appl. No. 61/136,617, 82 pages, copy provided by USPTO, filed Feb. 23, 2009.
Petition for inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016.
Declaration of Dr. John Izuchukwu, Ph.D., P.E., U.S. Pat. No. 8,479,741, IPR Nos. 2016-1714 & 2016-1718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for inter Partes Review of U.S. Pat. No. 8,443,807, IPR2016-01726, filed Dec. 13, 2016.
Decision Denying institution of Inter Partes Review of U.S. Pat. No. 8,443,807 Pursuant to 37 C.F.R. § 42.108, IPR2016-01726, entered Mar. 6, 2017.
Petition for Inter Partes Review of U.S. Pat. No. 8,443,807 Pursuant to 35 U.S.C. §§ 311-19, 37 C.F.R. § 42, IPR201 6-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al, published Oct. 1, 2009.
File History of U.S. Pat. No. 8,443,807 to McAuley et al, published Jan. 7, 2010.
Patent Owner's Complaint for Fisher & Paykel Healthcare Ltd. v. ResMed Corp., Case No. 2:16-cv-06099-R-AJW (C.D. Cal.), dated Aug. 15, 2016.
Patent Owner's Notice of Voluntary Dismissal Without Prejudice for Fisher & Paykel Healthcare Ltd. v. ResMed Corp., Case No. 2:16-cv-06099-R-AJW (C.D. Cal.), dated Aug. 16, 2016.
Patent Owner's Complaint for Fisher & Paykel Healthcare Ltd. v. ResMed Corp., Case No. 3:16-cv-02068-GPC-WVG (S.D. Cal.), dated Aug. 16, 2016.
Petitioners' Complaint for ResMed Inc., et al. v. Fisher & Paykel Healthcare Corp. Ltd., et al., Case No. 3:16-cv-02072-JAH-MDD (S.D. Cal.), dated Aug. 16, 2016.
Petitioners' Notice of Voluntary Dismissal Without Prejudice for ResMed Inc., et al. v. Fisher & Paykel Healthcare Corp. Ltd., et al., Case No. 3:16-cv-02072-JAH-MDD (S.D. Cal.), dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.

(56) References Cited

OTHER PUBLICATIONS

Statutory Declaration made by Alistair Edwin McAuley, Apr. 14, 2015, in the matter of an Opposition by Fisher & Paykel Healthcare Limited of Australian patent application 2009221630 in the name of ResMed Limited.

Statutory Declaration made by Alistair Edwin McAuley, Apr. 17, 2015, in the matter of an Opposition by Fisher & Paykel Healthcare Limited of Australian patent application 2009221630 in the name of ResMed Limited.

Statutory Declaration made by Alistair Edwin McAuley, Sep. 16, 2015, in the matter of an Opposition by Fisher & Paykel Healthcare Limited of Australian patent application 2009221630 in the name of ResMed Limited.

First Affidavit of Alistair Edwin McAuley, Dec. 5, 2016, in the matter of Fisher and Paykel Healthcare Limited v. ResMed Limited filed in the Federal Court of Australia.

Second Affidavit of Alistair Edwin McAuley, Dec. 21, 2016, in the matter of Fisher and Paykel Healthcare Limited v. ResMed Limited filed in the Federal Court of Australia.

Third Affidavit of Alistair Edwin McAuley, Jan. 31, 2017, in the matter of Fisher and Paykel Healthcare Limited v. ResMed Limited filed in the Federal Court of Australia, 284 pp.

Declaration of Anthony Michael Ging In IPR 2019-000172, IPR 2019-000173, IPR 2019-000177, IPR 2019-000178, dated Nov. 8, 2018, 329 pp.

McGraw-Hill Dictionary of Scientific and Technical Terms, Sixth Edition, 2003, Tube, p. 2200.

Claim Chart for AirFit P10, U.S. Pat. No. 9,333,315, dated Nov. 7, 2018, 3 pp.

Scheduling Order dated Jul. 16, 2019 in IPR2019-00180, 12 pp.

Decision to institute dated Jul. 16, 2019 in IPR2019-00180, 34 pp.

Decision Denying Institute of Inter Partes Review dated Jul. 16, 2019 in IRP2019-00179, 32 pp.

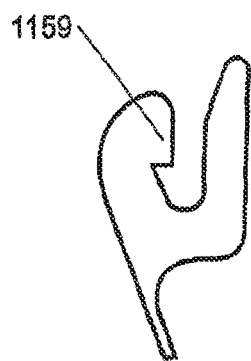
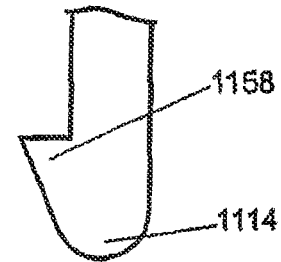
FIGURE 5　　　　FIGURE 6
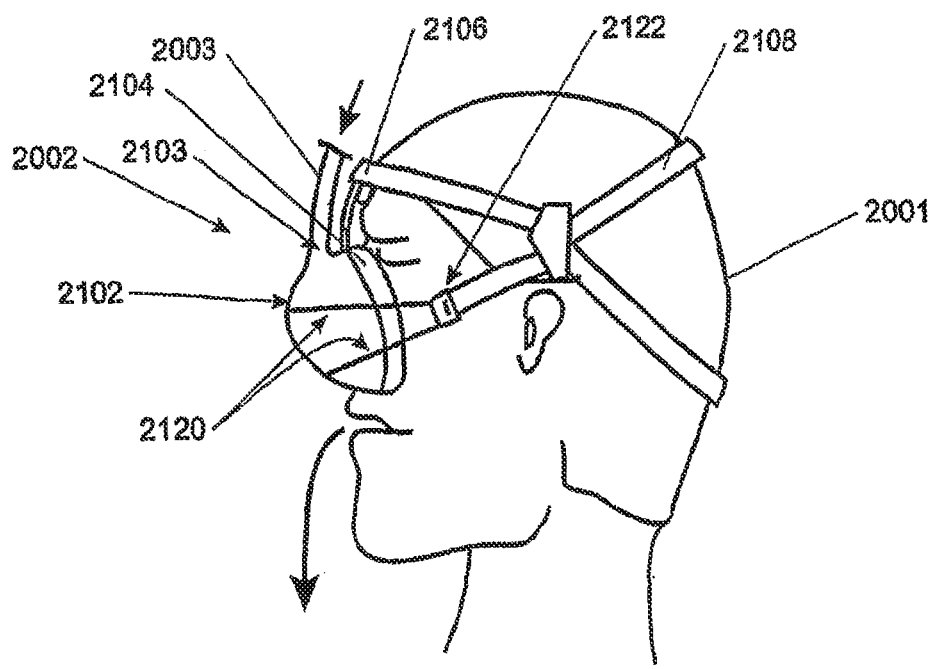
FIGURE 7

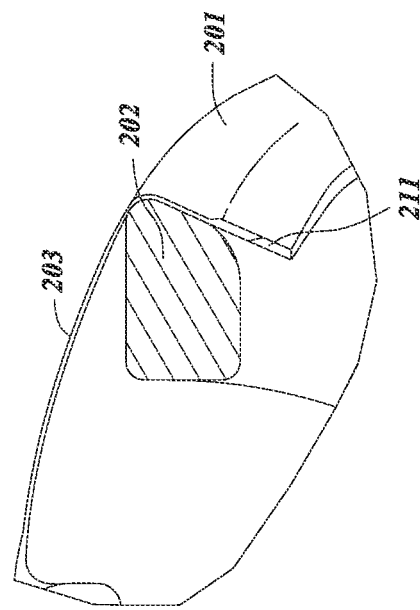
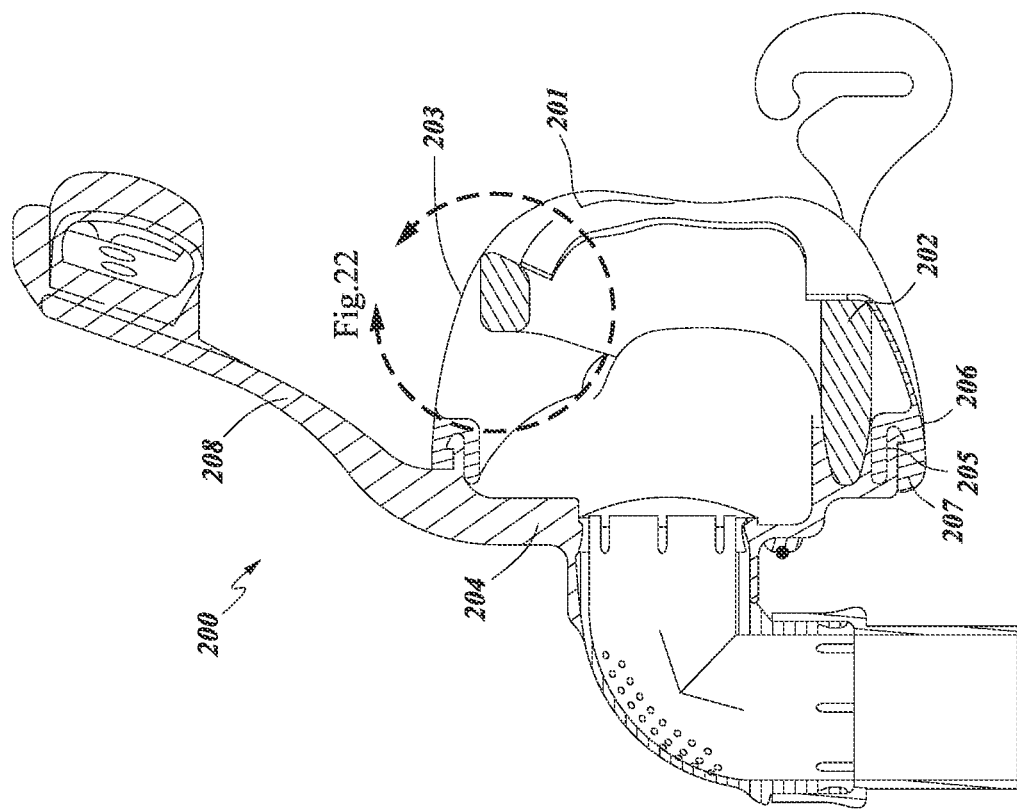

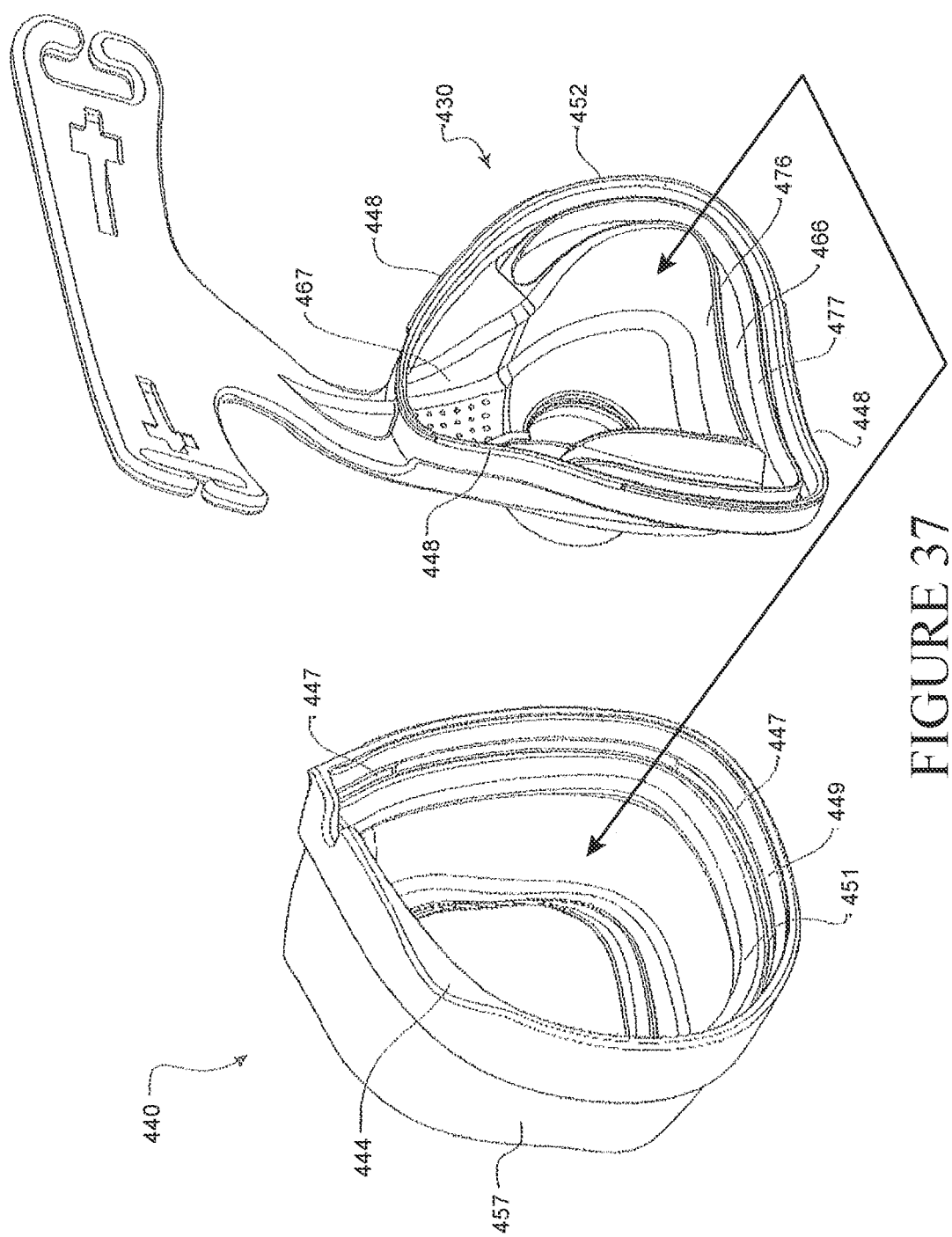

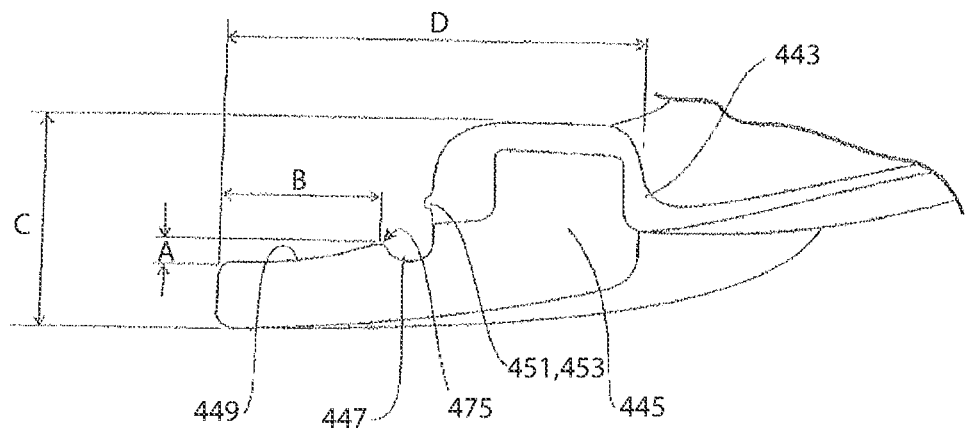
FIGURE 43
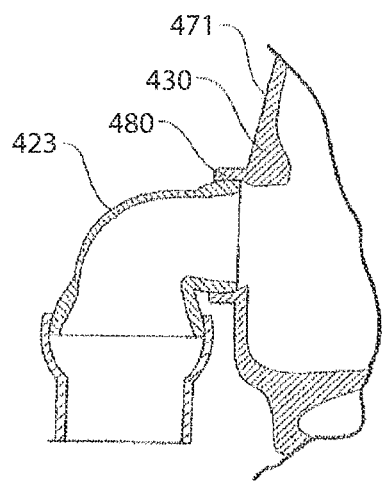 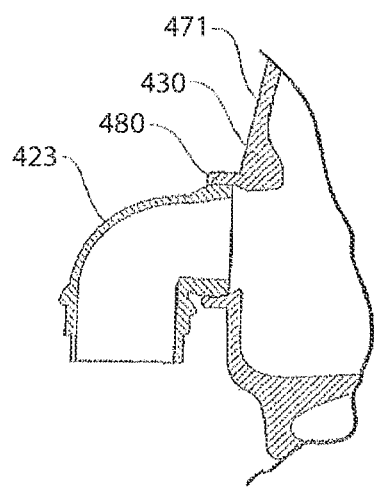
FIGURE 44A  FIGURE 44B

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a Continuation application of U.S. patent application Ser. No. 17/303, 892, filed Jun. 9, 2021, which is a Continuation application of U.S. patent application Ser. No. 14/792,399, filed Jul. 6, 2015, which is a Continuation application of U.S. patent application Ser. No. 12/502,528, filed Jul. 14, 2009, now U.S. Pat. No. 9,072,852. U.S. patent application Ser. No. 12/502,528 also claims the benefit of U.S. provisional application Ser. Nos. 61/082,007 filed on Jul. 18, 2008; 61/082, 974 filed on Jul. 23, 2008; and 61/083,554 filed on Jul. 25, 2008. Each of the above applications is hereby incorporated by reference in its entirety.

BACKGROUND OF THE INVENTION

Field of the Invention

This invention relates to patient interfaces particularly though not solely for use in delivering CPAP therapy to patients suffering from obstructive sleep apnoea (OSA).

Description of the Related Art

In the art of respiration devices, there are well known variety of respiratory masks which cover the nose and/or month of a hitman user in order to provide a continuous seal around the nasal and/or oral areas of the face such that gas may be provided at positive pressure within the mask for consumption by the user. The uses for such masks range from high altitude breathing (i.e. aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. Nos. 5,243,971 and 6,112,746 are examples of prior art attempts to improve the mask system. U.S. Pat. No. 5,570,689 and PCT publication No. WO 00/78384 are examples of attempts to improve the forehead rest.

Where such masks are used in respiratory therapy, in particular treatment of obstructive sleep apnea (OSA) using continuous positive airway pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. A further requisite of such masks is the washout of gas from the mask to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and any bed partners.

In common with all attempts to improve the fit, sealing and user comfort is the need to avoid a concentrated flow of air at any portion of the respiratory tracts. In particular with oral masks or mouthpieces it is a disadvantage of prior art devices that the oral cavity may become overly dehydrated by use of the device, causing irritation and possible later complications.

Furthermore, a common complaint of a user of CPA therapy is pressure sores caused by the mask about the nose and face and in particular in the nasal bridge region of the user.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a mask assembly for use as part of an apparatus for supplying a flow of respiratory gases to a user comprising:

a mask body, said mask body including an inlet through which said flow of respiratory gases are provided to the interior of said mask body, the inlet adapted to in use be connected, to a gases conduit, a mask seal assembly comprising a flexible seal and a rigid clip, said seal having a first side and a second side, the first side of said seal being shaped to approximately match the contours of a user's face and in use substantially seal against a user's face, said second side adapted for attachment to said clip, said clip being shaped to generally follow the contours of a user's face, and a rear periphery of said mask body also being correspondingly shaped to generally follow the contours of a user's face, said clip providing a rigid interface extending substantially the full perimeter or periphery of the mask seal assembly for releasably attaching the mask seal assembly to the mask body, and one of the clip or the mask body having at least one recess and the other one of the mask body or the clip having a series of bumps, interference between the bumps and the clip or the mask body during attachment of the clip to the mask body providing a positive snap type engagement of the clip to the mask body as the bumps locate in the at least one recess, and one of the clip or the mask body having a lead in section providing a gradual deflection of the clip, or the mask body, or both, when attaching the clip to the mask body, the lead-in section extending substantially the full perimeter of the clip or the mask body.

Preferably the seal has a wall portion extending around the periphery of the seal assembly between the first and second sides, the wall being approximately or substantially constant in depth.

Preferably wherein the recesses are located immediately behind the lead-in section.

Preferably a cross section of the mask seal assembly at the clip has a width to height ratio of 1.5 to 2.

Preferably the clip is adapted to disengage the seal assembly from the mask body when squeezed at opposite perimeter portions at positions absent of a said bump.

Preferably the corresponding shape of the clip and the mask body provides for automatic correction of angular misalignment between the seal assembly and the mask body when fitting the seal assembly to the mask body.

Preferably the seal assembly attaches to the mask body in a sealed engagement, a first bearing surface of the seal bearing against: a corresponding second bearing surface of the mask body in a butting engagement.

Preferably the first bearing surface comprising a raised rim, in use the raised rim being compressed against the second bearing surface.

Preferably the clip has at least one wing portion, the wing portion providing a gripping flange to assist with removing the seal assembly from the mask body.

Preferably the lead-in section extends at least 50% of the full perimeter of the seal assembly clip or the mask body.

Preferably the mask assembly further comprises headgear for securing the mask assembly to the head of a user.

Preferably the mask assembly further comprises an inner cushion around the outer periphery of the mask body between the mask body and the first side of the sea).

Hie term "comprising" as used in this specification means "consisting at least in part of". Related terms such as "comprise" and "comprised" are to be interpreted in the same manner.

To those skilled in the art to which the invention relates, many changes in construction and widely differing embodiments and applications of the invention will suggest themselves without departing from the scope of the invention as defined, in the appended claims. The disclosures and the descriptions herein are purely illustrative and are not intended to be in any sense limiting The invention consists in the foregoing and also envisages constructions of which the following gives examples.

BRIEF DESCRIPTION OF THE DRAWINGS

Preferred forms of the present invention will now be described with reference to the accompanying drawings.

FIG. 5 is a cutaway view of the periphery of the outer sealing member or membrane.

FIG. 6 is a cutaway view of the periphery of the mask body portion.

FIG. 7 shows a mask and sealing interface as used with a forehead rest on a patient.

FIG. 21 is a side view of a nasal mask of the present invention where the outer sealing member is substantially thinner in width in the nasal bridge region than the rest of the outer sealing member.

FIG. 22 is a close-up view of detail A in FIG. 21.

FIG. 36 b is a perspective view of the seal clip of the mask seal assembly of FIG. 36 a.

FIG. 37 is a perspective view showing the mask body and the mask seal assembly, with the mask seal assembly removed from the mask body.

FIG. 39 b is a part sectional view showing a first alternative form of the interface arrangement between the mask body and the mask seal assembly.

FIG. 39 c is a part sectional view showing a second alternative form of the interface arrangement between the mask body and the mask seal assembly.

FIG. 39 d is a part sectional view showing a third alternative form of the interface arrangement between the mask body and the mask seal assembly.

FIG. 39 e is a part sectional view showing a forth alternative form of the interface arrangement between the mask body and the mask seal assembly.

FIG. 43 is a part sectional view from the side showing tire clip and seal arrangement of the mask seal assembly of FIG. 34.

FIG. 44 a and FIG. 44 b are pail sectional views from tire side of preferred forms of connector for connecting a conduit, to the mask assembly.

FIGS. 45 b and 45 bb show a perspective view and a rear view of a second alternative form of connector for connecting a conduit to the mask assembly, the connector incorporating a single wave like baffle.

FIGS. 45 c and 45 cc show a perspective view and a rear view of a third alternative form of connector for connecting a conduit to the mask assembly, the connector incorporating a single circular baffle centrally located within the connector.

FIGS. 45 d and 45 dd show a cutaway side view and a rear view of a fourth alternative embodiment of connector for connecting a conduit to the mask assembly, the connector incorporating two radially aligned baffles.

DETAILED DESCRIPTION OF THE PREFERRED EMBODIMENT

The sealing interface of the present invention provides improvements in the delivery of CPAP therapy. In particular a patient interface is described which reduces the pressure of the mask on the patient's face and may be quieter for the patient to wear and reduces the side leakage as compared with the prior art. It will be appreciated that the patient interface as described in the preferred embodiment of the present invention can be used in respiratory care generally or with a ventilator, but will now be described below with reference to use in a humidified CPAP system. It will also be appreciated that the present invention can be applied to any form of patient interface including, but not limited to, nasal masks, oral masks and mouthpieces.

Figure 1:
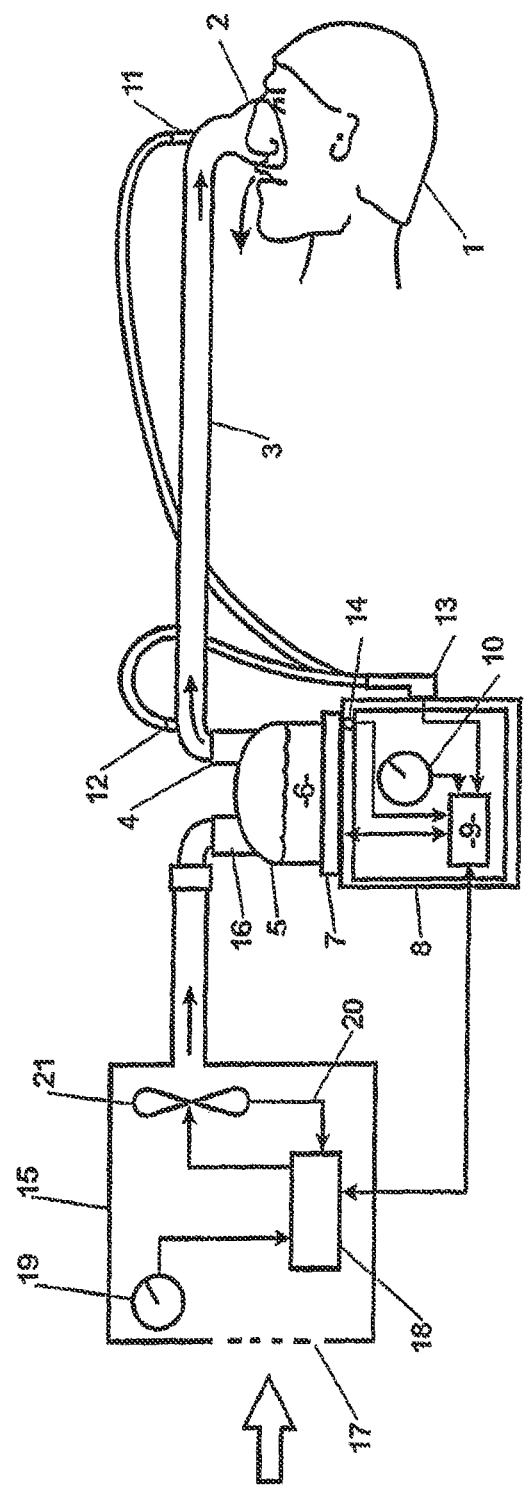
FIG. 1 is a block diagram of a humidified continuous positive airway pressure (system) as might be used in conjunction with the sealing interface of the present invention.

With reference to FIG. 1 a humidified Continuous Positive Airway Pressure (CPAP) system is shown in which a patient 1 is receiving humidified and pressurised gases through a patient interface 2, 50 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 that contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources: for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller IS could carried out by controller 9) in response to inputs from controller 9 and a user set predetermined required value (preset value) of pressure or fan speed via dial 19.

Nasal Mask

Figure 2:
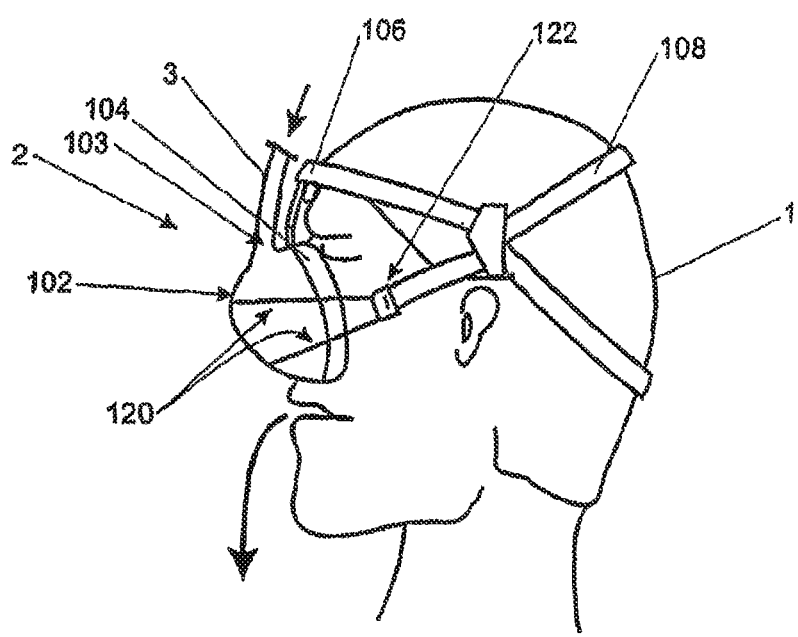
FIG. 2 is an illustration of the nasal mask including a sealing interface in use according to the preferred embodiment of the present invention.

According to a first embodiment of the present invention the patient interface is shown in FIG. 2 as a nasal mask. The mask includes a hollow body 102 with an inlet 103 connected to the inspiratory conduit 3. The mask 2 is positioned around the nose of the patient 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
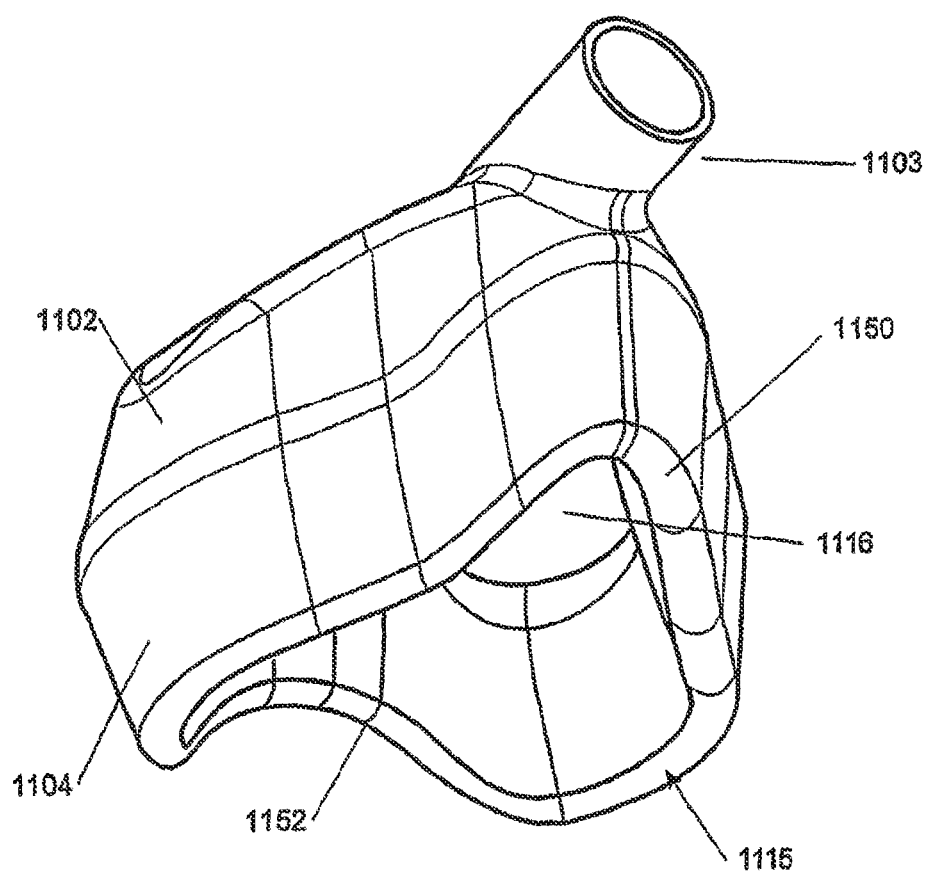
FIG. 3 shows a perspective view of a mask with a sealing interface that is a cushion.
Figure 4:
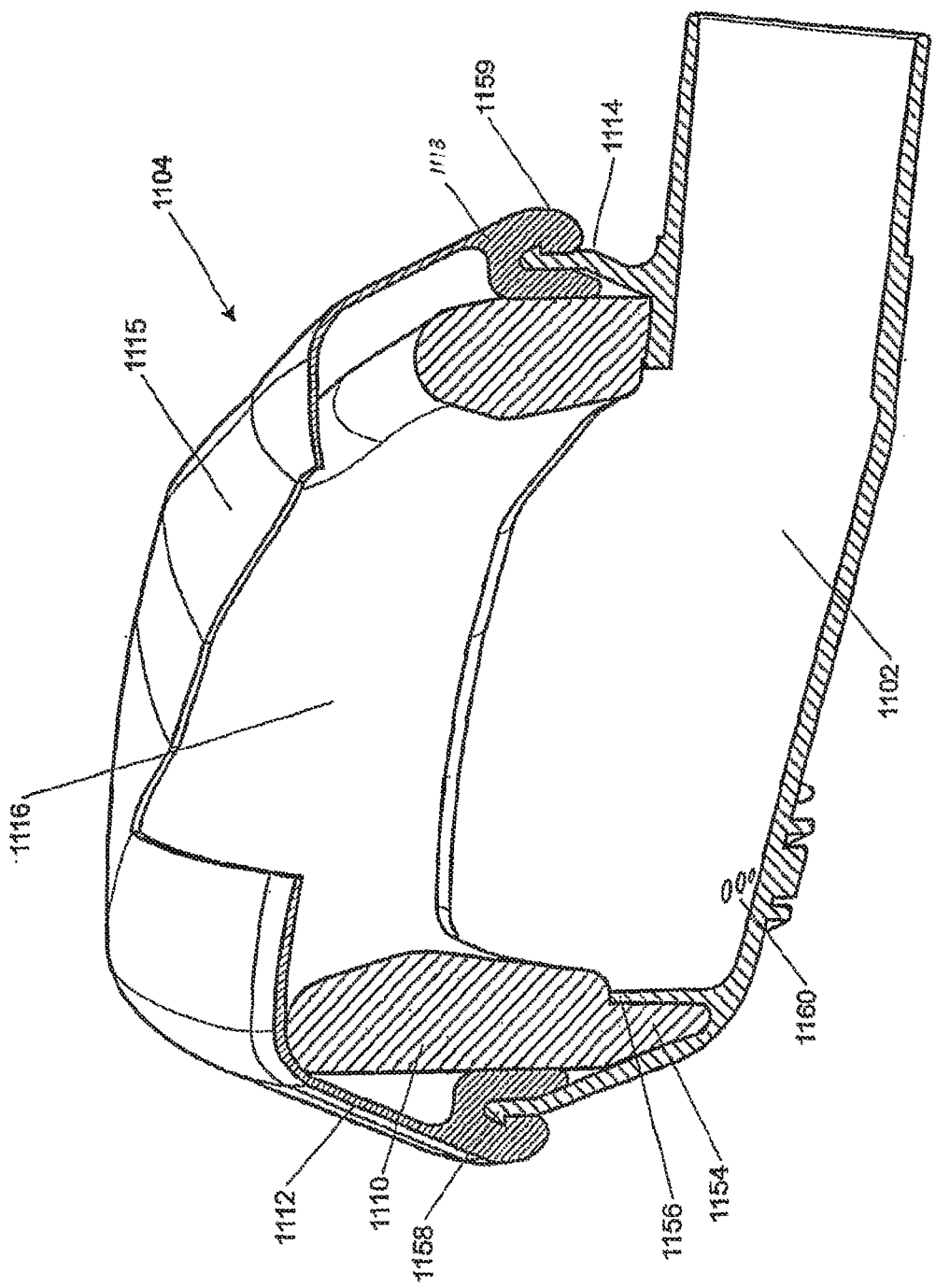
FIG. 4 is a cutaway view of the mask showing the sealing interface cushion that has an inner sealing member and an outer sealing member.

Referring now to FIGS. 3 and 4 in particular, the mask cushion 1104 is provided around the periphery of the nasal mask 1102 to provide an effective seal onto the face of the patient to prevent leakage. The mask cushion 1104 is shaped to approximately follow the contours of a patient's face. The mask cushion 1104 will deform when pressure is applied by the headgear 2108 (see FIG. 7) to adapt to the individual contours of any particular patient, in particular, there is an indented section 1150 intended to fit over the bridge of the patient's nose as well as an indented section 1152 to seal around the section beneath the nose and above the upper lip.

In FIG. 4 we see that the mask cushion 1104 is composed of an inner sealing member that is an inner cushion 1110 covered by an outer sealing sheath or member 1112. The inner cushion 1110 is constructed of a resilient material for example polyurethane foam, to distribute the pressure evenly along the sea) around the patient's face. In other forms the inner cushion 1110 may be formed of other appropriate material, such as silicone or other composite materials. The inner cushion 1110 is located around the outer periphery 1114 of the open face 1116 of the hollow body 1102. Similarly the outer sheath 1112 may be commonly attached at its base 1113 to the periphery 1114 and loosely covers over the top of the inner cushion 1110.

In the preferred embodiment of the present invention as shown in FIGS. 4 to 6 the bottom of the inner cushion 1110 fits into a generally triangular cavity 1154 in the hollow body 1102. The cavity 1154 is formed from a flange 1156 running mid-way around the interior of the hollow body.

The outer sheath 1112 fits in place over the cushion 1110, holding it in place. The sheath 1112 is secured by a snap-fit to the periphery 1114 of the hollow body. In FIGS. 5 to 6 the periphery 1114 is shown including an outer bead 1158. The sheath 1112 includes a matching bead 1159, whereby once stretched around the periphery; the two beads engage to hold the sheath in place.

Figure 9:
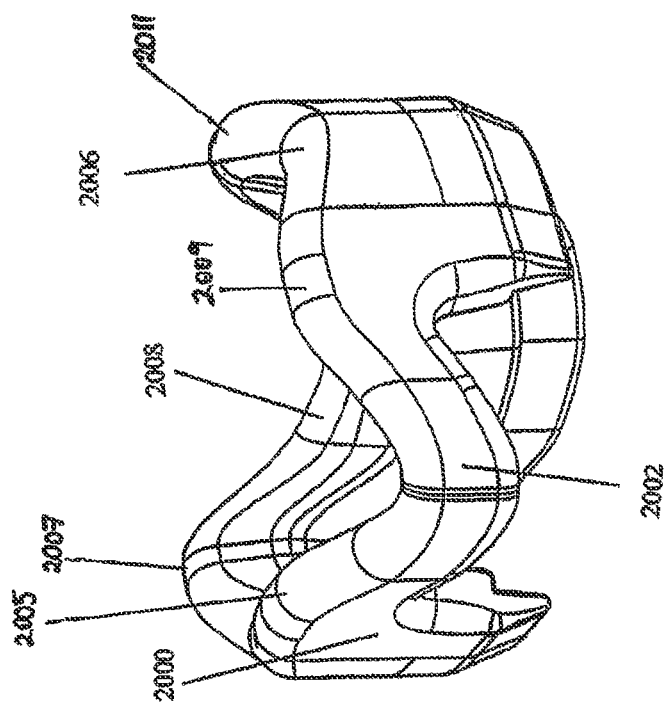
FIG. 9 shows perspective view of an inner sealing member of the second preferred embodiment of the sealing interface.
Figure 8:
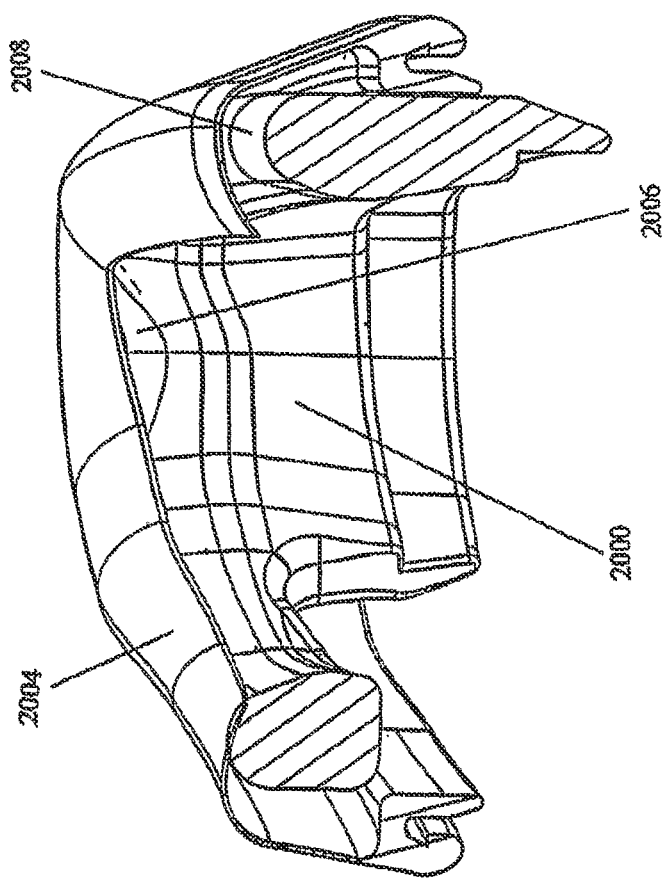
FIG. 8 shows a cross section of a second preferred embodiment of the sealing interface.
Figure 10:
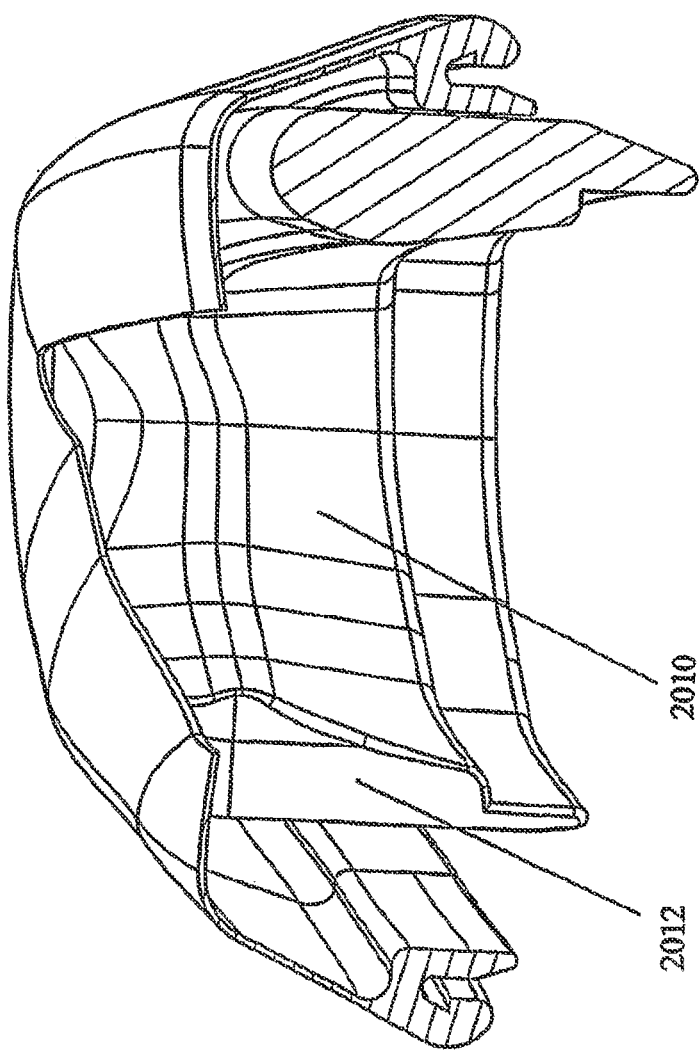
FIG. 10 shows a cross section of a third preferred embodiment of the inner and outer sealing members of the present invention.

A second preferred embodiment to the mask cushion is depicted in FIGS. 9 and 10. In the second embodiment the inner cushion 2000 includes a raised bridge 2002 in the nasal bridge region. The raised bridge 2002 can also be described as a cut out section made in the cushion. Also, the notch in the contacting portion (between the inner cushion and outer sheath) is less pronounced than, proceeding embodiments. However, as the raised bridge 2002 is unsupported it is much more flexible and results in less pressure on the nasal bridge of the patient. The outer sheath 2004 contacts the inner cushion 2000 throughout the raised bridge 2002. The peaks 2005, 2007, 2009, 2011 in the inner cushion 2000 between each of the indented sections 2006, 2008 and the raised bridge 2002 contact the outer sheath 2004 and when in use the sheath 2004 contacts the facial contours of the patient in the regions of these peaks.

Referring particularly to FIG. 10 the inner cushion 2000 includes a cheek contour 2006 to follow the cartilage extending from the middle of the nose, and a contoured lip scaling portion 2008 to seal between the base of the nose and the upper lip.

Figure 12:
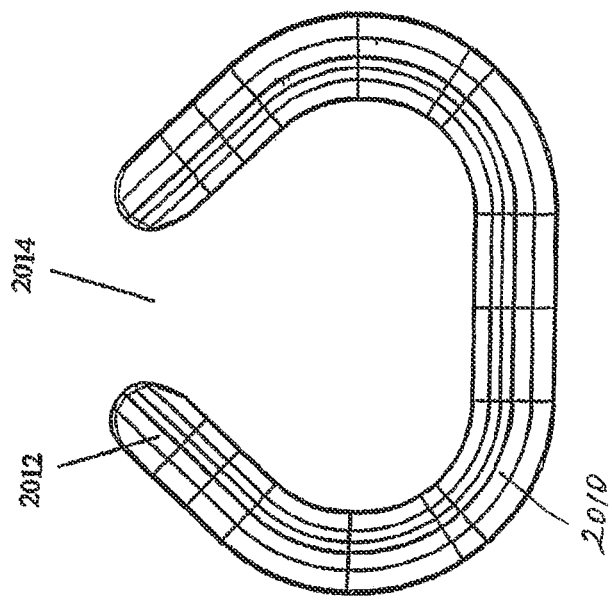
FIG. 12 shows a plan view of the inner sealing member of the third preferred embodiment of the mask cushion.
Figure 11:
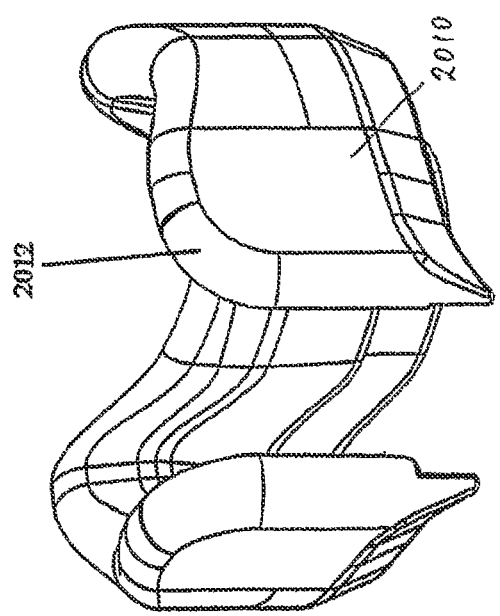
FIG. 11 shows a perspective view of the inner sealing member of the third preferred embodiment of the sealing interface.

Referring now to FIGS. 11 and 12 a third preferred embodiment of the mask cushion is depicted, in this case, the inner cushion 2010 tapers down 2012 towards the nasal bridge region 2014. For a short portion either side of the nasal bridge region 2014 the inner cushion 2010 is absent, forming a semi annular form in plan view as seen in FIG. 12.

Figure 13:
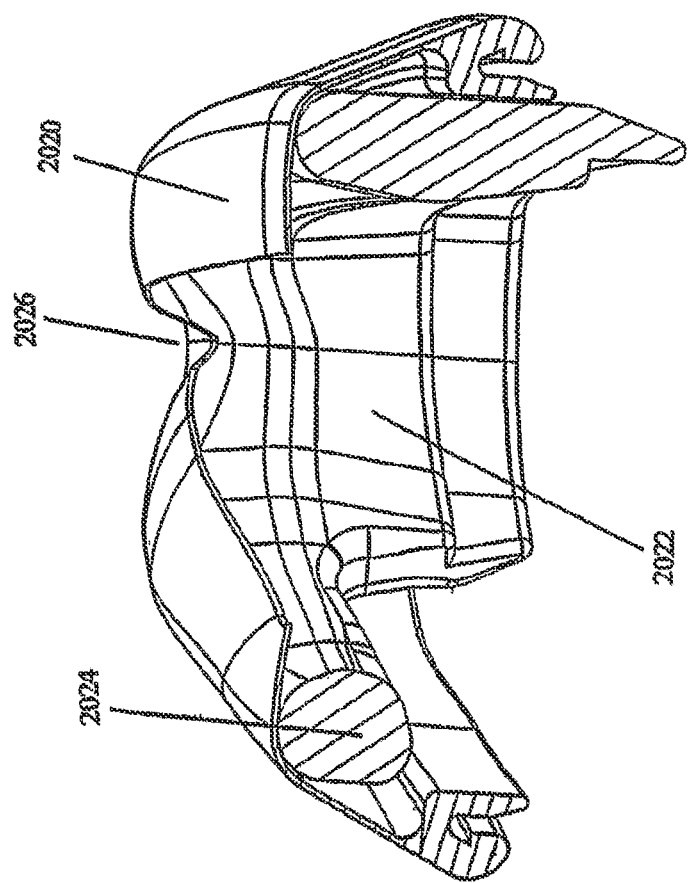
FIG. 13 shows a cross section of a fourth preferred embodiment of the sealing interface of the present invention.
Figure 18:
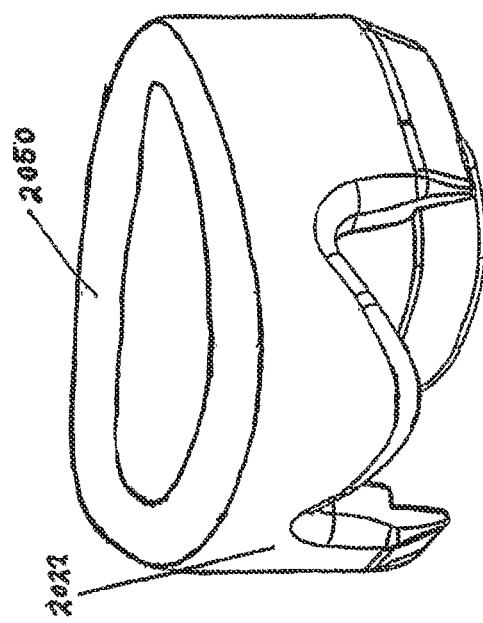
FIG. 18 shows a perspective view of the inner sealing member according to a ninth preferred embodiment of the sealing interface of the present invention.
Figure 20:
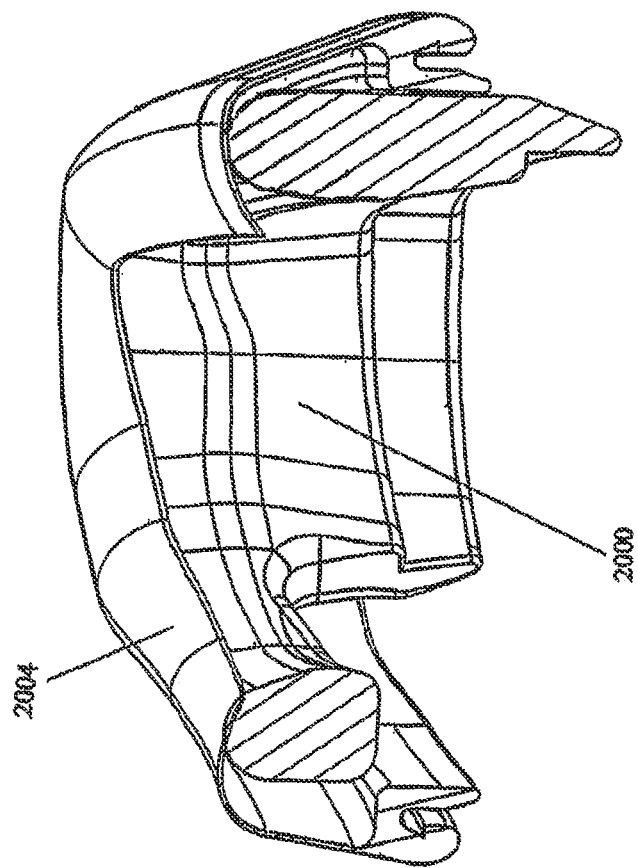
FIG. 20 shows across section of a further embodiment of the sealing interface of die present invention where the inner sealing foam member touches the outer sealing member at all times.

Referring to FIG. 13, a fourth preferred embodiment of the mask cushion is depicted. The outer sheath 2020 is adapted to contact the inner cushion 2022 completely about the inner cushion, including in the nasal bridge region 2024 and the check contour 2026. FIG. 18 shows the inner cushion 2022 where the upper edge 2050 of the cushion docs not have any contours and thus will contact the outer sheath all around the edge of the inner cushion. FIG. 20 shows a sealing interface similar to that of FIG. 13 where the inner cushion also follows and touches the outer sheath all around its edge.

Figure 14:
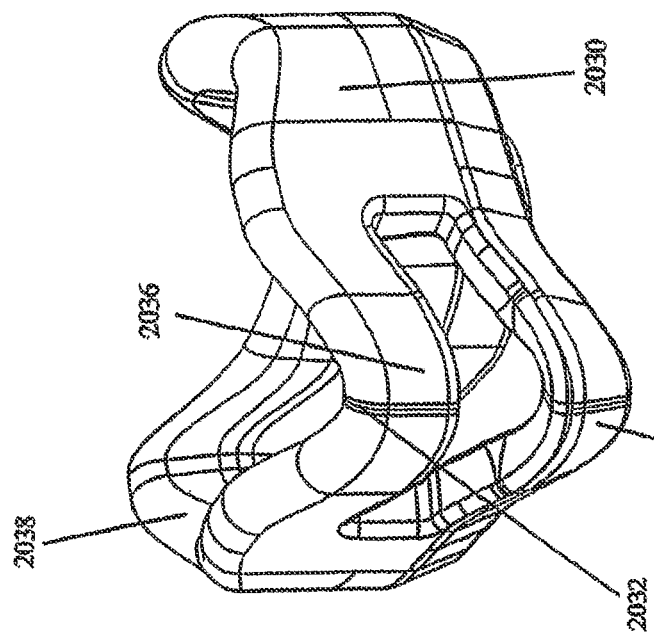
FIG. 14 shows a perspective view of the inner sealing member according to a fifth preferred embodiment of the sealing interface of the present invention.

FIG. 14 illustrates a fifth preferred embodiment of the inner cushion 2030. In the nasal bridge region 2032 the inner cushion includes a lower bridge 2034 and upper bridge 2036. Due to the gap the upper bridge 2036 is unsupported to reduce pressure on the patient's nasal bridge, but the lower rim 2034 of the inner cushion 2030 is continuous, which aids installation.

Figure 16:
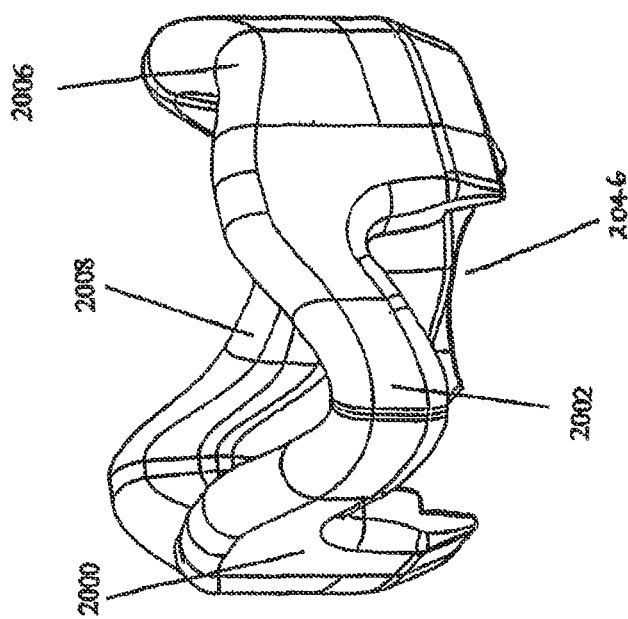
FIG. 16 shows a perspective view of the inner sealing member according to a seventh preferred embodiment of the sealing interface of the present invention.
Figure 15:
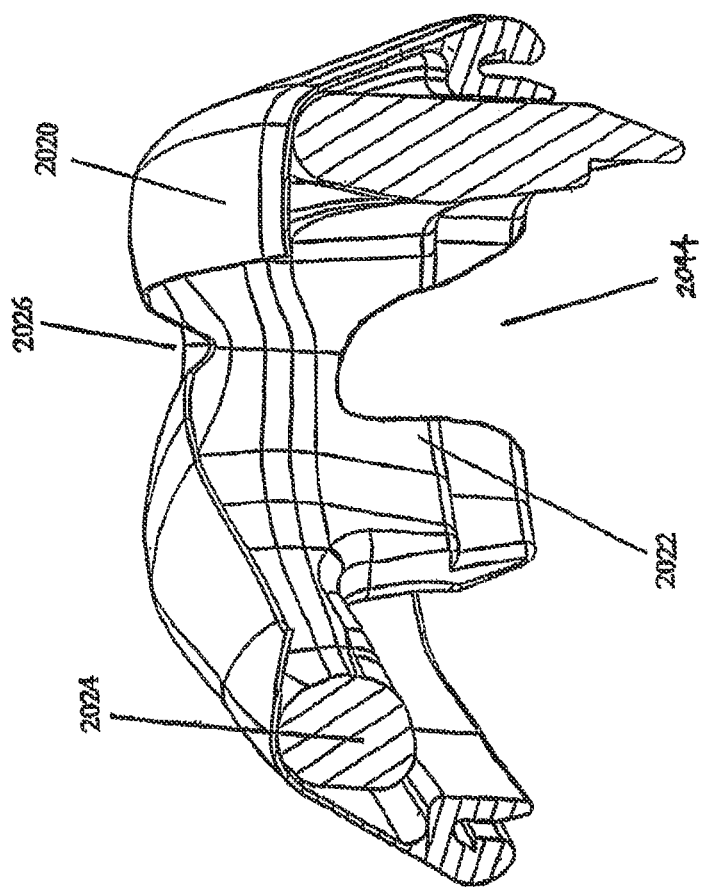
FIG. 15 shows a cross section of a sixth preferred embodiment of the sealing interface of the present invention.
Figure 17:
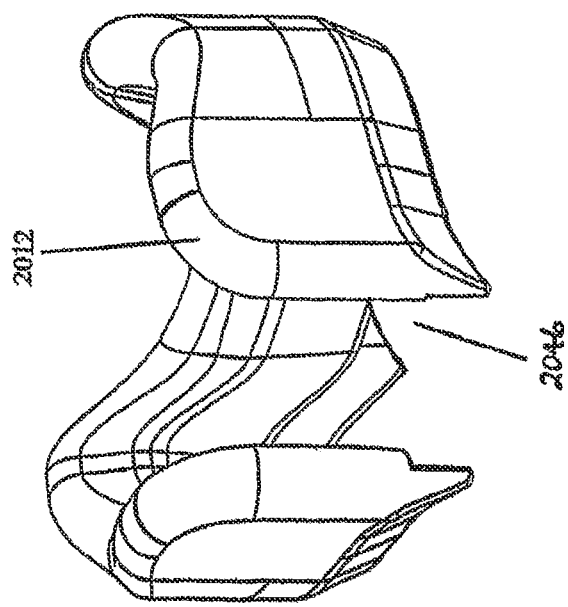
FIG. 17 shows a perspective view of the inner sealing member according to an eighth preferred embodiment of the sealing interface of the present invention.

In yet other forms of the sealing interface of the present invention the inner cushion may be provided with other contours on the front side of the inner cushion or cut outs on the back side of the inner cushion, so that in the areas where there are regions cutout of die back side of the cushion the cushion is more flexible. In particular, cut outs in the nasal bridge, cheek and upper lip regions provide the patient with a mask cushion that is more flexible and thus more comfortable. FIG. 15 shows an embodiment of an inner cushion 2024 that has a curved cut out or dead space 2044 in the cheek region. FIGS. 16 and 17 show embodiments of an inner cushion 2000 that has a cut out or dead space 2046 in the area where the patient's upper lip rests in the foam.

Figure 19:
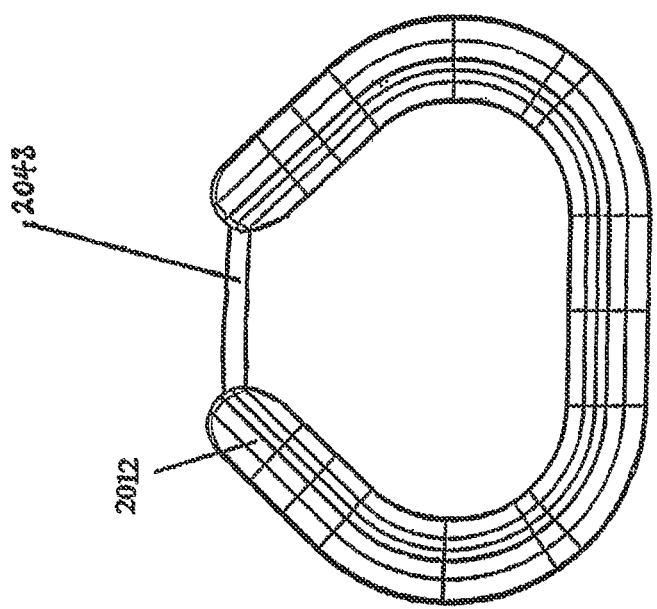
FIG. 19 shows a perspective view of the inner sealing member according to a tenth preferred embodiment of the sealing interface of the present invention.

A final form of a sealing interface is shown in FIG. 19, here the inner foam member has an annular shape but has a thin bridge or membrane 2048 that, extends across and provides flexibility to the nasal bridge region.

Referring now to FIG. 21, to improve the comfort to the patient the nasal mask 200 includes a thin bridge section 203 in the nasal bridge region of the outer sealing member 201, that is, that part extending over the bridge of a patient's nose.

Similar to that described above the outer sealing member or outer sheath 201 fits in place over the inner sealing member (inner cushion) 202, holding it in place. The outer sheath 201 is secured by a snap-fit to the periphery 205 of the mask hollow body 204. The periphery 205 is shown including an outer bead 206. The outer sheath 201 includes a matching bead 207, whereby once stretched around the periphery 205; the two beads engage to hold the outer sheath 201 in place.

Figure 23:
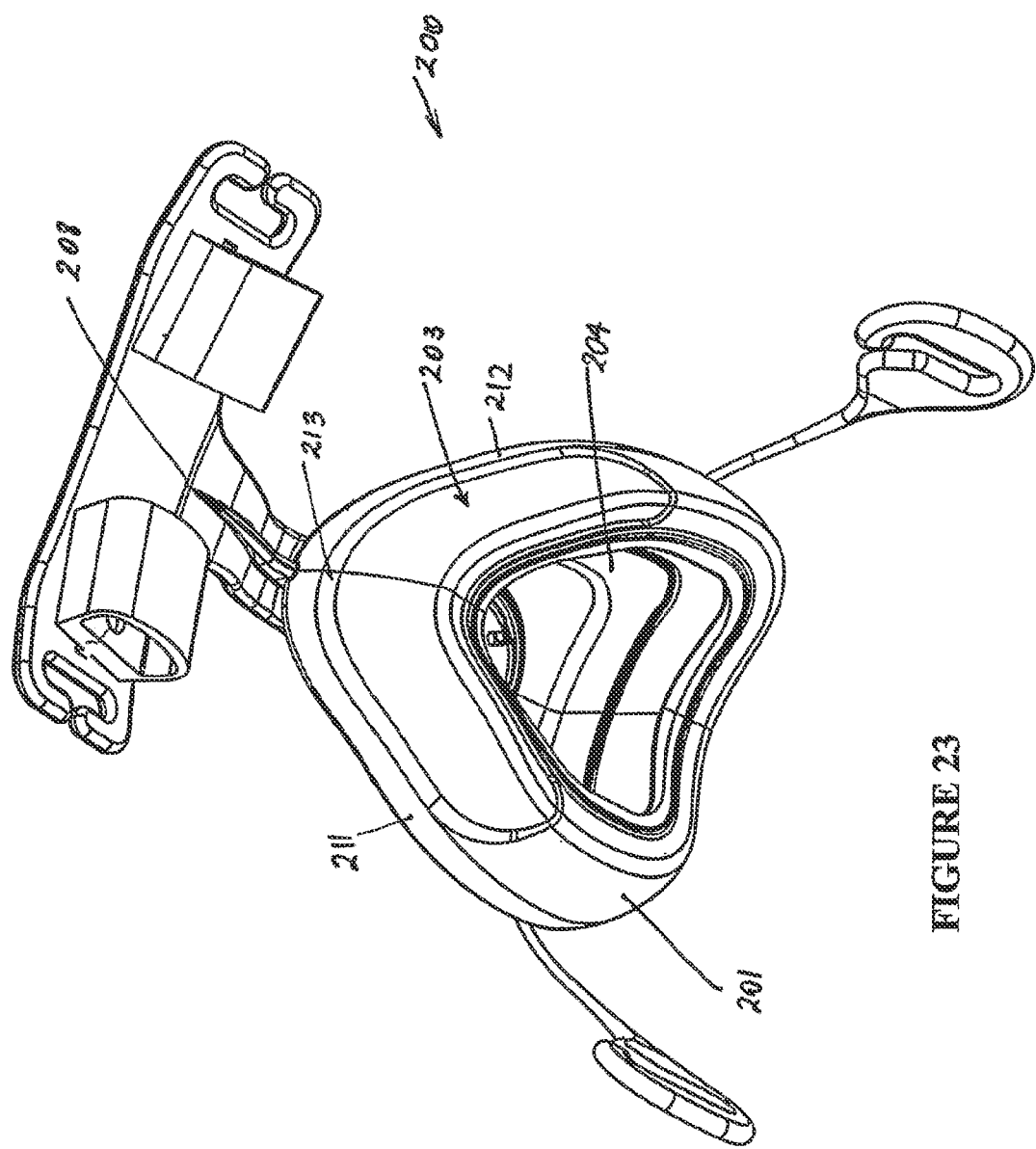
FIG. 23 is a perspective view of the nasal mask of FIG. 21.
Figure 24:
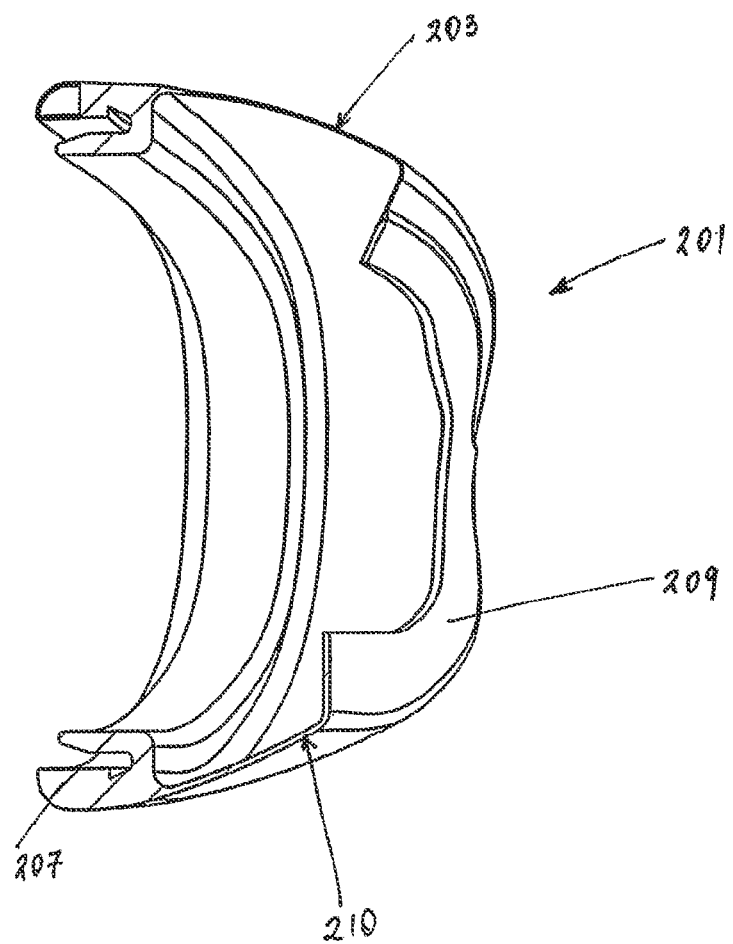
FIG. 24 is a cross-section of the outer sealing member of FIG. 21.

The outer sealing member or sheath 201 is shown in more detail in FIGS. 22 to 24. The outer sheath 201 has formed in it a region 203 that is thinner than the remainder of the cross-sectional thickness 210 of the sheath. In particular, the side walls 211, 212 (see FIG. 23) must be thicker than in the region 203 so as to provide structural support for the sheath and ensure the sheath does not collapse in use, or when being assembled with the mask body. As an example only, for a nasal mask, if the thin bridge region was 0.2 mm thick, the side walls may be 0.3 to 0.6 mm thick. Therefore, the thin bridge region 203 is approximately half the thickness of the rest of the sheath 201 and so can provide a significant effect, such that the pressure to the patient's nose in the nasal bridge region is reduced compared to when a sheath does not have any reduced thickness section. Furthermore, a thin bridge region 203 in the outer sheath 201 allows for different sized patient's to comfortably use the mask and outer sheath of the present invention.

In use, when a force is placed against the outer sheath 201 the thin bridge region 203 will collapse more than the rest of the outer sheath 201. Therefore, this section 203 is more flexible and allows for added patient comfort.

Referring particularly to FIG. 22, the thin bridge region 203 on the outer sheath 201 preferably does not extend completely to She outer edge 211 of the outer sheath 201, but grows thicker in thickness. This is because the outer edges of the outer sheath 201 when thicker are less prone to tearing.

In particular, in FIG. 23, that outer sheath 201 is substantially heart shaped and the thin bridge region 203 is shown to extend more than halfway down the sides of the sheath from the apex 213. As shown in FIG. 23, the thin bridge region 203 does not extend fully down the edges 211 and 212 of the outer sheath 201. This is because support is required in the edges of the sheath 201, to provide structural stability of the sheath.

Figure 30:
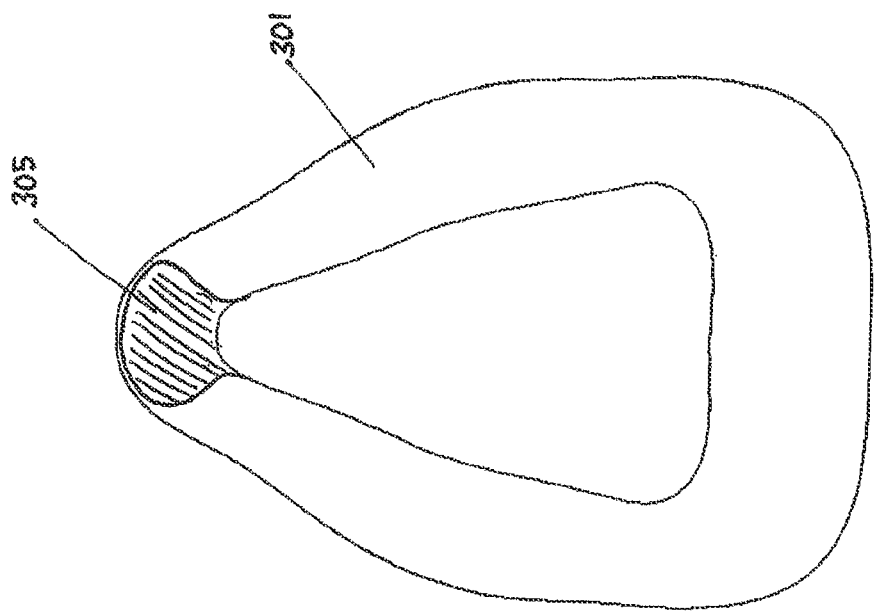
FIG. 30 is a front view of the outer sealing member of FIG. 28.

In other forms of the nasal mask of the present, invention, the thin bridge region may not extend as far as that shown in FIG. 23, but be restricted merely to the nasal bridge region (similar in manner to the mask cushion shown in FIG. 30, in relation to a full face mask).

Full Face Mask

A further embodiment of the present invention is shown in FIGS. 25 to 31 where the patient interface is a full face mask similar to that described in co-pending New Zealand patent application number 528029. The full face mask 300 includes a hollow body 302 and outer sealing member or mask cushion 301. The cushion 301 is attached to the body 302 in a similar manner as described with reference to the nasal mask, but here no inner cushion is provided. Thus, the cushion 303 periphery extends over a flange on the mask body.

The hollow body 302 has an integrally formed recess (not shown) in which an insert 304 is fitted into. The recess and insert 304 each have complimentary circular apertures (generally indicated as 305) that form an inspiratory inlet when the insert 304 is placed in the recess. The inlet 304 is capable of being connected to the tubing that forms the inspiratory conduit 3 (as shown on FIG. 1). Oases, supplied to the inspiratory conduit 3 from the CPAP device and humidifier, enter the mask through the apertures 305 and the patient is able to breathe these gases. The mask 300 is positioned around the nose and mouth of the patient and headgear (not shown) may be secured around the back of the head of the patient to assist in the maintaining of the mask on tire patient's face. The restraining force from the headgear on the hollow body 302 ensures enough compressive force on the mask cushion 301 to provide an effective seal against the patient's face.

The hollow body 302 and insert 304 are injection moulded in a relatively inflexible material, for example, polycarbonate plastic. Such a material would provide the requisite rigidity for the mask as well as being transparent and a relatively good insulator. The mask cushion 301 is preferably made of a soft plastics material, such as silicone, KRATON™ or similar materials.

Figure 29:
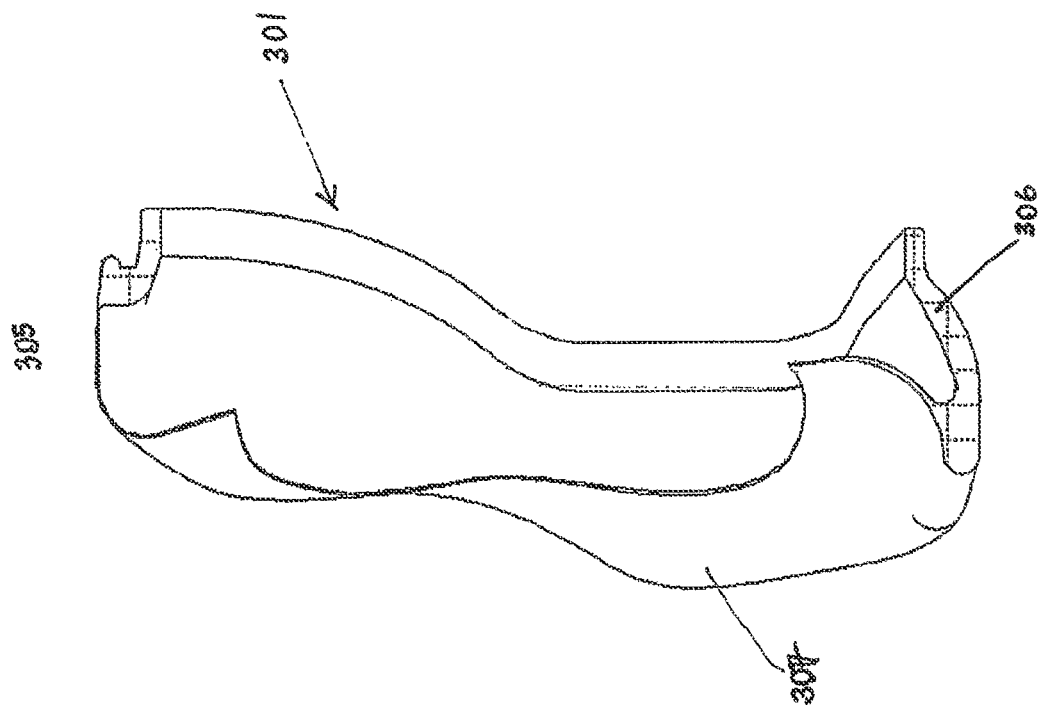
FIG. 29 is a cross-section through CC of the outer sealing member of FIG. 28.

The cushion 301 of the mask 300 includes a thin bridge section 305 in the nasal bridge region of the cushion 301 that is, that part extending over the bridge of a patient's nose. As an example, in the region of the thin bridge section 305 the walls of the cushion may be 0.2 to 0.3 mm thick and the rest of die cushion may have a thickness of 1 mm. In particular, the side walls need to be thicker to provide support in the cushion, so that it does not collapse during use or assembly with the mask body. In FIG. 29, this is particularly illustrated, as the section 305 in the nasal bridge region is shown as being much thinner than the rest of the cushion (in particular the bottom side wail region 306, which are much thicker in cross-section).

Note must be made that the inner flange 307 of the cushion 301 that rests against the patient's face is also thinner in section than the side walls of the cushion 301 to provide flexibility to the cushion and thus comfort to the patient. In use the inner flange 307 is the area of the cushion that seals against the patient's face and the side walls of the cushion provide stability to the cushion 301.

In use, when a force is placed against the cushion 301 the thin bridge section 305 will collapse more than the rest of the cushion 301. There fore, this section 305 is more flexible and allows for added patient comfort.

Figure 33:
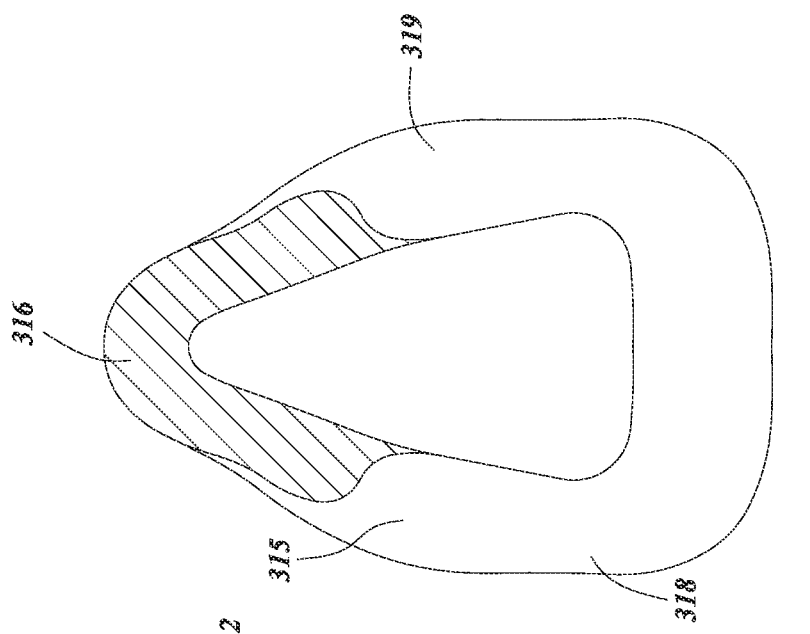
FIG. 33 is a front view of a third alternative outer sealing member.
Figure 32:
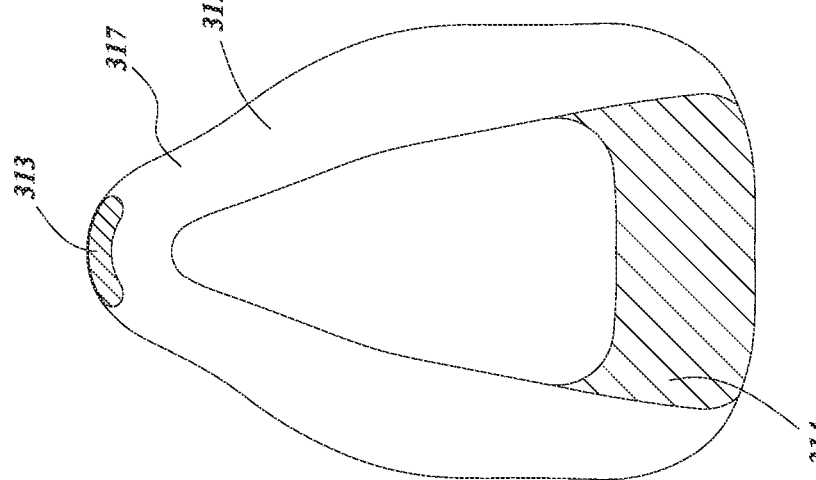
FIG. 32 is a front view of a second alternative outer sealing member.
Figure 31:
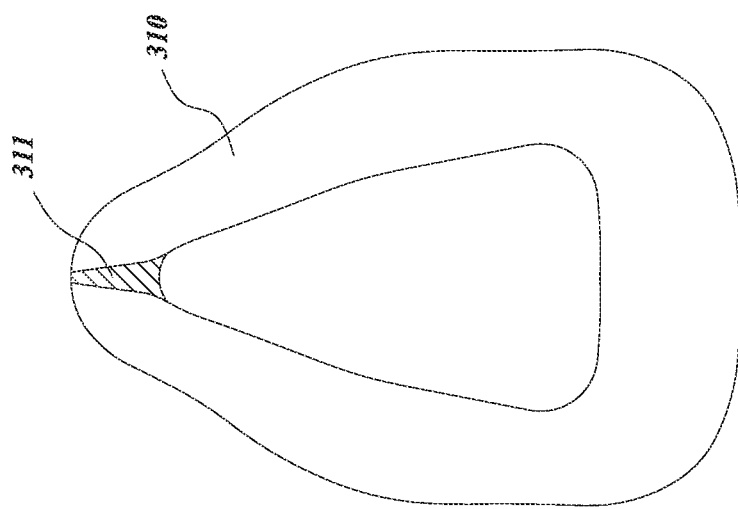
FIG. 31 is a front view of a first alternative outer sealing member.

Other forms of the cushion that may be used with the full face mask of the present invention are shown in FIGS. 31 to 33 and each show alternative thin sections that may be provided for patient comfort, and to allow for fitting to different sized patients.

Referring first to FIG. 31, cushion 310 may have a thin bridge section 313 that is narrower than that shown in FIG. 30.

In FIG. 32 the cushion 312 has a thin bridge section 313 only near the outer edge 317 of the cushion 312. This cushion 312 also had a thin section 314 in the region of the cushion that would rest against the patient's chin.

Finally, in FIG. 33, the thin section 316 of the cushion 315 may extend down the sides 318, 319 of the cushion.

Forehead Rest

Figure 25:
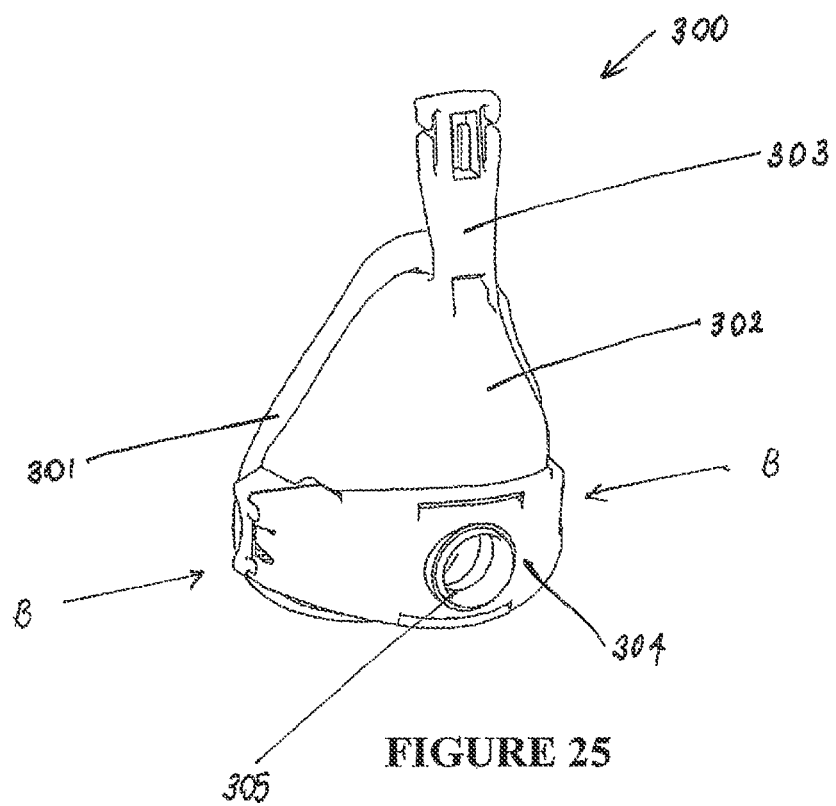
FIG. 25 is a front perspective view of a full face mask of the present invention, where the outer sealing member is substantially thinner in width in the nasal bridge region than the rest of the outer sealing member.
Figure 26:
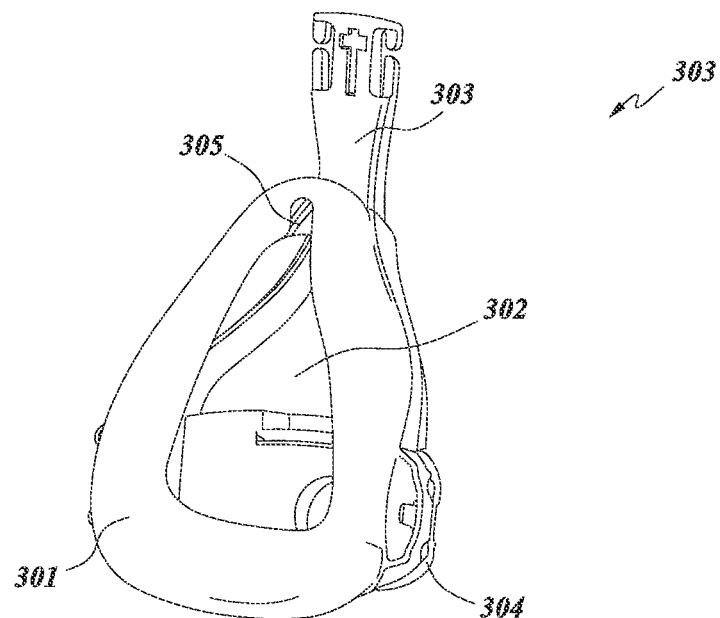
FIG. 26 is a back perspective view of a full face mask of FIG. 25.
Figure 27:
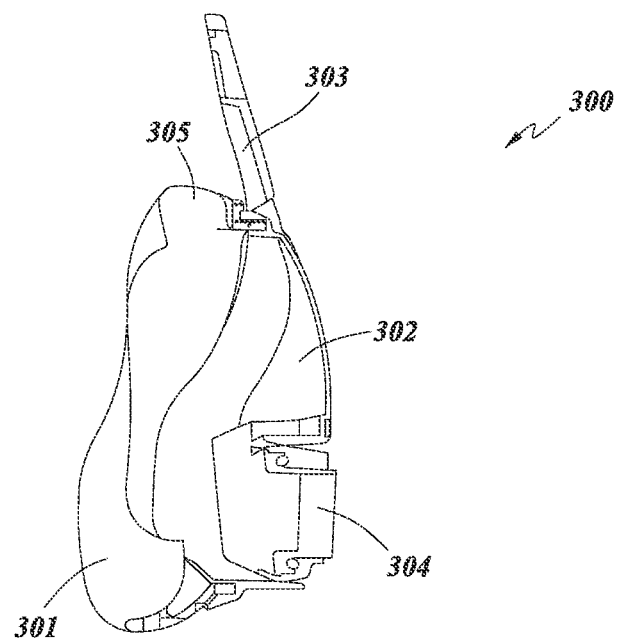
FIG. 27 is a cross-section through BB of the full face mask of FIG. 25.
Figure 28:
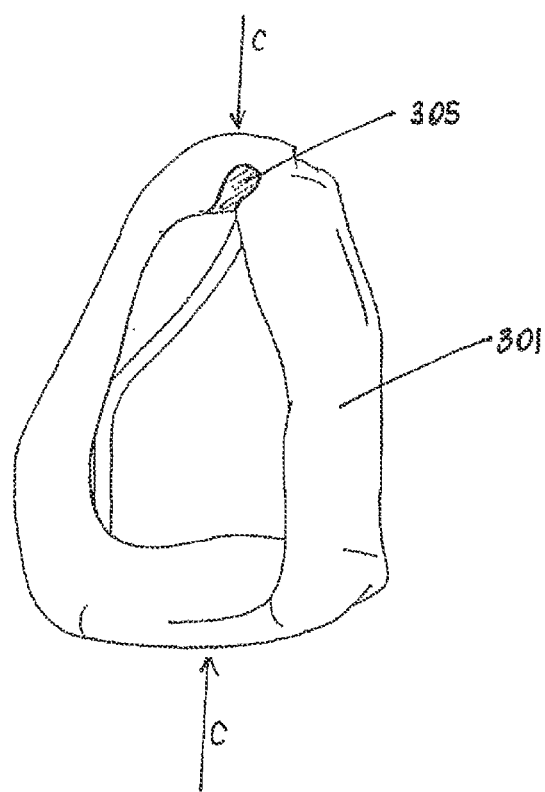
FIG. 28 is a perspective view of the outer sealing member of the full face mask of FIG. 25 in isolation, where the thin nasal bridge region is particularly shown.

The nasal mask and/or full face, mask of the present invention is preferably provided with a fixed forehead rest (208, as shown in relation to the nasal mask in FIGS. 21 and 23 or 303, as shown in relation to the full face mask in FIG. 25). The forehead rest is not required to be adjustable as the cut out in the nasal bridge region of the inner foam (for the nasal mask) and the thin section in the outer sheath (for both the nasal and full face masks) provides enough flexibility of the mask cushion to provide fitting to a number of different patients.

Improved Patient Interface

A further preferred embodiment of the present invention is patient interface 50 described with reference to FIG. 34 and FIG. 35. The patient interlace 50 includes a mask assembly 402 and headgear 421.

Headgear

Headgear 421 is worn by the user in use, and holds the mask assembly 402 in the required position on the user's face. The headgear 421 in the preferred form is comprised of headgear straps 435, 436, 437, 438, and an elongate glider member 434. The elongate glider member extends across the front of the mask assembly 402 and attaches to the mask body 430 of the mask assembly 402 via at least one clip type fitting 433. The elongate member 434 may slide, or glide, within the clip type fitting 433 so that the mask assembly 402 may move laterally with respect to the head gear. This arrangement for attaching the headgear to the mask assembly is the preferred arrangement. Other arrangements may also be used, such as a fixed or static arrangement.

Each end of the elongate glider member may include a hook 432 to which each end of headgear strap 435 may releasably attach. Alternatively, headgear strap 435 may attach directly to the mask body 430.

In the preferred form, the mask assembly 402 includes a forehead support 431. The forehead support, is attached to the mask body 430 by a vertical support member 429, the forehead, support and vertical support member together forming a T shape. The forehead support 431, vertical support member 429 and mask body 430 may be integrally formed as a single piece.

Alternatively, the forehead support may be adjustable in a vertical direction, or may be pivotably attached to the mask body 430.

One end of headgear strap 436 may attach to a first end of the forehead support, and the opposite end of headgear strap 436 may attach to a second end of the forehead support 431. The forehead support may include at least one support pad or cushion 428. In use, the forehead support locates against the user's forehead and provides stability to the nasal interface 50 when fitted, to the user.

Headgear straps 437 and 438 extend substantially vertically between headgear straps 435 and 436. Headgear straps 437 and 438 provide support to straps 435 and 436, positioning straps 435 and 436 a set distance apart around the user's head.

The headgear straps are preferably made from a laminated sheet of open cell foam sandwiched between two sheets of textile fabric.

It should be noted that many equivalent forms of head gear known in the art may be suitable for use with the mask assembly 402. What has been described above is the preferred farm.

Mask Body

Figure 34:
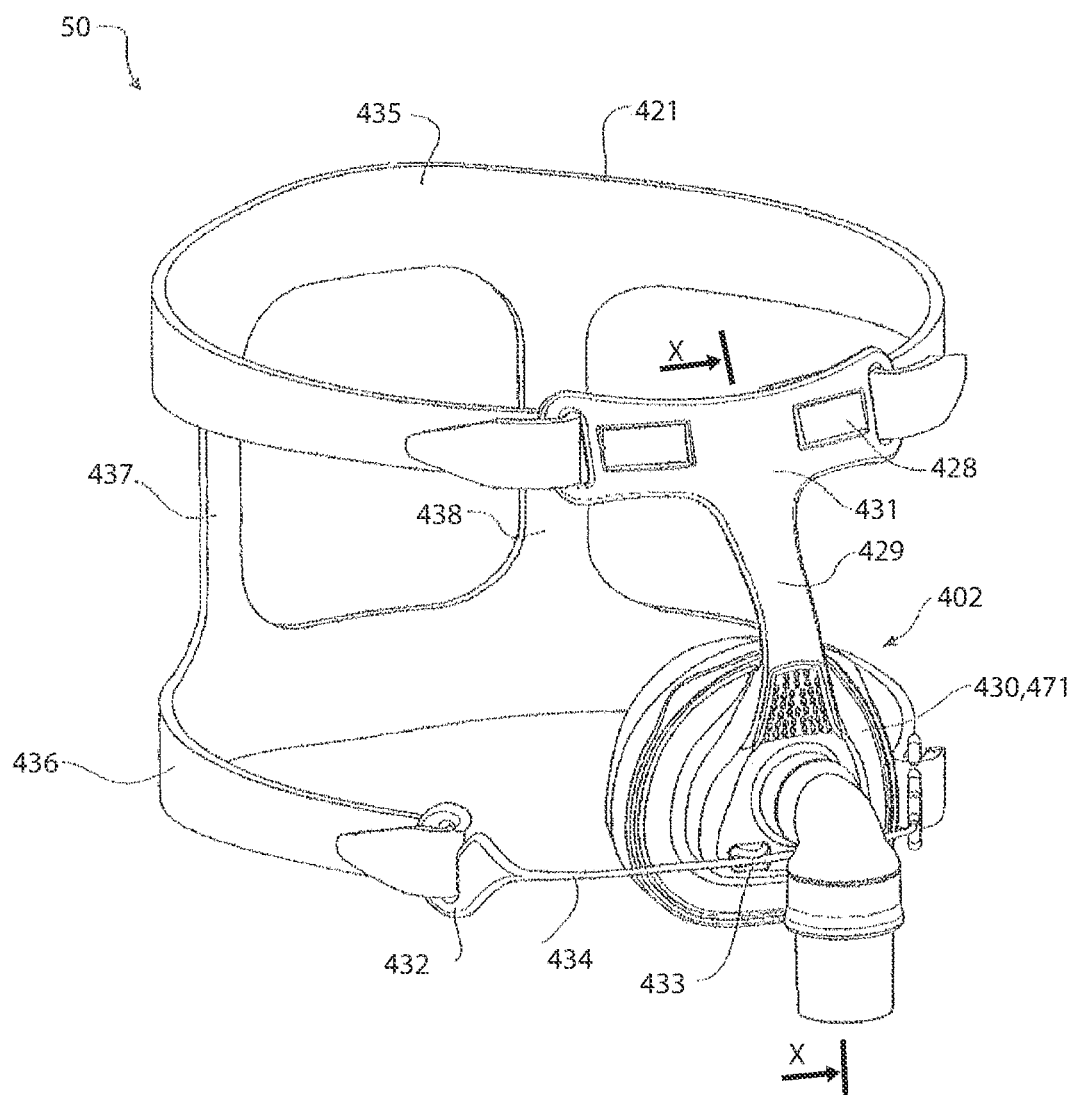
FIG. 34 is a perspective view of a preferred embodiment of a patient interface.
Figure 35:
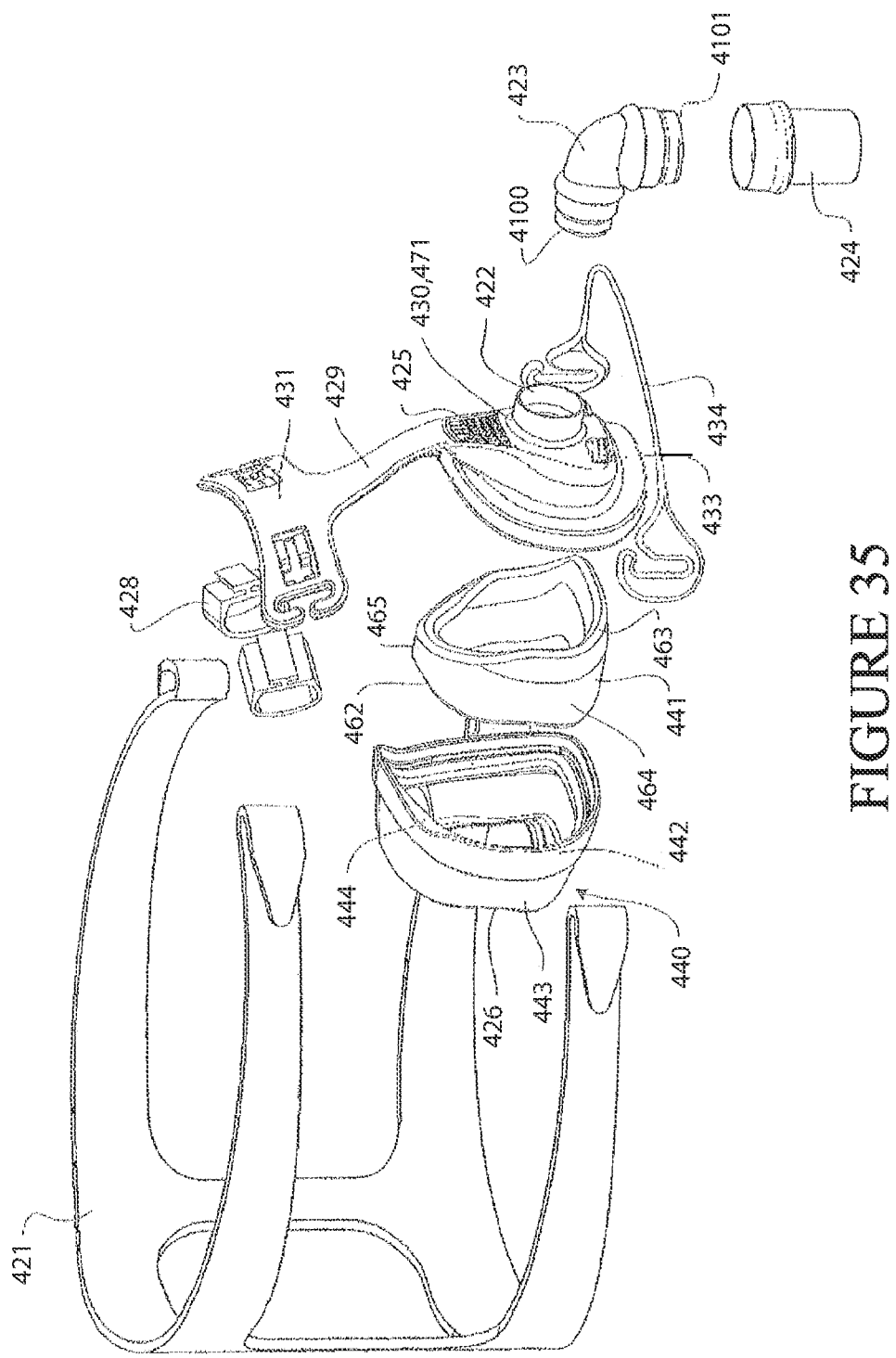
FIG. 35 is an exploded view of the patient interface of FIG. 34, the patient interface comprising headgear, a mask seal assembly, a mask cushion and a mask body.

The mask assembly 402 of FIGS. 34 and 35 comprises a mask body 430 and a mask seal assembly 440.

The mask body 430 provides the overall structural support for the mask assembly, and provides at least one clip type fitting for attaching the mask assembly 402 to the headgear 421.

A rear side of the mask body 30 interfaces to the seal assembly 440, the seal assembly 440 providing a sealing interface against a user's face in use. The rear side of the mask body 430 is the side that faces towards a user, when the user has the mask assembly 402 in place on their face. The mask body 430 has an inlet for receiving a flow of respiratory gases. The mask body forms an internal cavity to which respiratory gases are supplied via the inlet from the CPAP system. The inlet comprises a tubular projection 422 extending from a front side 471 of the mask body 430. The front side 471 of the mask body 430 is the side that faces away from a user, when the user has the mask assembly 402 in place on their face.

Connector

A first end of connector 423 connects to the mask body tubular projection 422. The interface between the tubular projection 422 and the connector 423 preferably allows the connector 423 to swivel with respect to the mask body 430.

Alternatively, as shown in FIGS. 44 a and 44 b, the inlet may comprise a semi-tubular projection 480 extending from the front side 471 of the mask body. The semi-tubular projection forms a socket for receiving a correspondingly shaped first end of the connector 423. In use, the first end of the connector and the semi-tubular projection form a ball joint allowing the connector 423 to swivel and pivot within the socket, relative to the mask body 430. In alternative embodiments the mask body 430 may not include a projection, and the inner surface of the mask body 430 may be curved to form a socket for receiving the connector. In other alternative forms, other types of connection may be utilised between, the mask body and the connector, such as a flexible piece of silicone, or other appropriate connection mechanism.

The connector 423 is preferably an elbow connector having a first leg a bend and a second leg. The bend is preferably a substantially 90 degree bend.

A second end of the connector connects to the inspiratory conduit 3, either directly to the conduit 3, or via a second connector 424. The interface between the elbow connector 423 and the conduit 3 or the second connector 424 preferably allows the conduit 3 to swivel with respect to the connector 423.

Alternatively, the interface between the second end of the connector and the conduit 3 may comprise a ball joint that allows the second end of the connector to swivel and pivot relative to the conduit, as shown in FIG. 44A.

Preferably the connection between the mask body 430 and the conduit 3 can be flexed or rotated to allow for the conduit to be moved without causing the dislodgement of the mask assembly 402 from the user's face. This is a preferred feature, but is not essential.

As best shown in FIG. 35, the preferred form of elbow connector 423 is a substantially right angle connector with the tubular inlet projection 422 aligned substantially perpendicular to the front of the mask body 430. Other alternative arrangements may be incorporated in the mask assembly of the present invention. For example, the connector may be a straight connector, with any necessary bend accommodated by the conduit 3. Alternatively, the tubular inlet projection may extend from the front of the mask body at an angle, for example angling downwards, with the connector having a corresponding obtuse angle.

Preferably the connector 423 may be easily removed from the mask body by pulling the connector 423 away from the mask body 430.

Reducing Diameter Connector

As shown in FIG. 35, in the preferred form, the first end 4100 of the elbow connector 423, interfacing with the mask body 430, is smaller in diameter than the second end 4101 of the elbow connector. Preferably the diameter of the connector 423 reduces around the length of the bend in the connector 423, from the full diameter at the second or outer end, to the reduced diameter at the first or inner end. As an example, the diameter of the inspiratory conduit commonly used in the art is approximately 25 mm. Prior art masks continue this full diameter through to the mask body interface. In the preferred form, the diameter of the connector 423 at the mask body interface is reduced to approximately 20 mm.

It is desirable to have a mask assembly that is as small and lightweight as possible, while at the same time providing an effective seal against a user's face. The reducing diameter of the connector 423 helps to make the mask assembly lightweight and small. The reducing diameter of the connector 423 helps to visually give the mask assembly a small, compact look.

One problem with a connector 423 having a reducing diameter connector is that air flow through the connector can become unacceptably noisy. Noise is created as the air flow passes through the reducing cross section of the connector. It is thought that this noise is created by an increase in the speed and turbulence of the flow of inspiratory gases through the reduced cross section portion 4102 of the connector 423. The additional noise level is clearly undesirable as it can disturb the user's sleep, or the sleep of a user's partner.

To overcome the problem of increased noise levels, the connector 423 of the preferred embodiment includes at least one baffle 4103 located in the reduced cross section portion of connector 423.

FIGS. 45 a and 45 aa show a first alternative form of the connector 423, including six equally spaced baffles 4103, each baffle extending from a first end 4100 of the reduced cross section portion 4102 of connector 423 to a second end 4104 of the reduced cross section portion of connector 423. The introduction of the baffles significantly reduces the noise create by the reduced cross section portion.

A downside to introducing the baffles is a higher pressure drop through the connector 423. It has been determined by the inventors following extensive research that a significant reduction in noise level is achieved by incorporating two baffles only, the baffles located at the third and fifth positions when considering six equally spaced positions spaced from top-dead-centre around the circumference of the reduced cross section portion of connector 423, top-dead-centre being position 1, with the second leg of the elbow at the downwards fourth, or 6 o'clock, position. This arrangement is shown as a fourth alternative embodiment in FIGS. 45 d and 45 dd.

The noise reduction achieved by incorporation of two baffles only in the positions described is similar to the noise reduction achieved with incorporation of all six baffles. The introduction of two baffles in the third and fifth positions results in a significant reduction in noise levels, a similar result to the introduction of six baffles as shown in FIGS. 45 a and 45 aa. However, the pressure drop in the flow of gases through the connector 423 due to the incorporation of two baffles is lower than the pressure drop with six baffles. The most preferred form of baffle arrangement is therefore to include two baffles, located at the positions described, resulting in an acceptable compromise between acceptable noise levels and acceptable resistance to flow through the connector 423. The fourth alternative embodiment, which shows the most preferred form of baffle arrangement, is shown in FIGS. 45 d and 45 dd. The baffles are preferably aligned radially within the reduced cross section portion of connector 423.

In the preferred embodiment the baffles connect to the circumferential wall 4105 of connector 423. The baffles extend along the wall 4105 substantially parallel to a longitudinal axis of the reduced portion 4102. Preferably the baffles extend from the second end 4104 of the reduced diameter portion to the first end 4100 of the reduced portion. Alternatively, the baffles may extend part way along the reduced diameter portion. Preferably the baffles extend along the full length of the reduced diameter portion 4102 and connect along the wall 4105, along the full length of the baffle except for an end portion 4107 near the first end 4100 of the connector 423, the end portion 4107 of each baffle 4103 being detached from the side wall 4105. The end portion 4307 of each baffle 4103 is not connected to the wall 4105 of the connector 423 so that additional strength provided by the baffles is not applied to the connector wall at the first end 4100. This allows the wall 4105 at the first, end 4100 to deflect more easily when connecting connector 423 to the mask body 430.

The baffles are around 1.5 mm thick and around 3 mm in radial height from the side wall 4105. The thickness of the baffle is not overly important for achieving a reduction in noise level. The thickness dimension is chosen to allow ease of manufacturing. The connector 423 is typically manufactured by plastic injection moulding. Other injection moulding techniques may be incorporated for ease of manufacture, such as (halting the internal bore of the connector and drafting the baffles. Preferably the sides 4106 of the baffles 4103 have a draft of around 0.5". The edge 4107 of the baffles 4103 have the same draft as the internal diameter of the reduced diameter portion 4102, that is, a draft of around 1° to 1.5°.

Further research found that the radial height of the baffles had a significant effect on the reduction in noise levels. A significant reduction in noise level was obtained with a baffle radial height of 3 mm. There was a large improvement in noise reduction by increasing the radial height from 2 mm to 3 mm. However, the improvement achieved by increasing the radial height from 3 mm to 4 mm was not as significant.

In an alternative embodiment the baffles 4103 may be connected to form a continuous bridge across the cross section of the reduced diameter portion 4102. However, for performance and ease of manufacture this is not a preferred embodiment.

Alternative baffle arrangements have also been found to be useful in reducing noise levels of gases flow through connector 423. FIGS. 45 b and 45 bb show a single baffle that extends across the reduced cross sectional area of the connector, the baffle being curved to extend towards the side nearest the elbow bend of connector 423, that is, the side opposite top-dead-centre with the second leg in the downward 6 o'clock position. FIGS. 45 c and 45 cc show a single circular baffle located centrally within the reduced cross section portion of connector 423, the circular baffle being supported by extensions at the six and three o'clock positions connecting between the outer wall of the single circular baffle and the inner wall of the connector. However, based on testing carried out by the inventors, these alternative embodiments are not the most preferred forms.

The use of baffles may also be helpful in reducing noise levels in an elbow connector with equal diameter legs, as turbulence in the gases flow is caused by flow around the bend of the elbow.

Alternatively, the use of baffles may also be helpful in reducing noise levels caused by a gases flow through a reducing diameter connector that has a straight through bore.

Mask Seal Assembly and Mask Seat Assembly to Mask Body Interface

Preferred and alternative forms of the mask body 430 and a mask seal assembly 440 shall now be described with reference to FIG. 36-43.

Figure 36A:
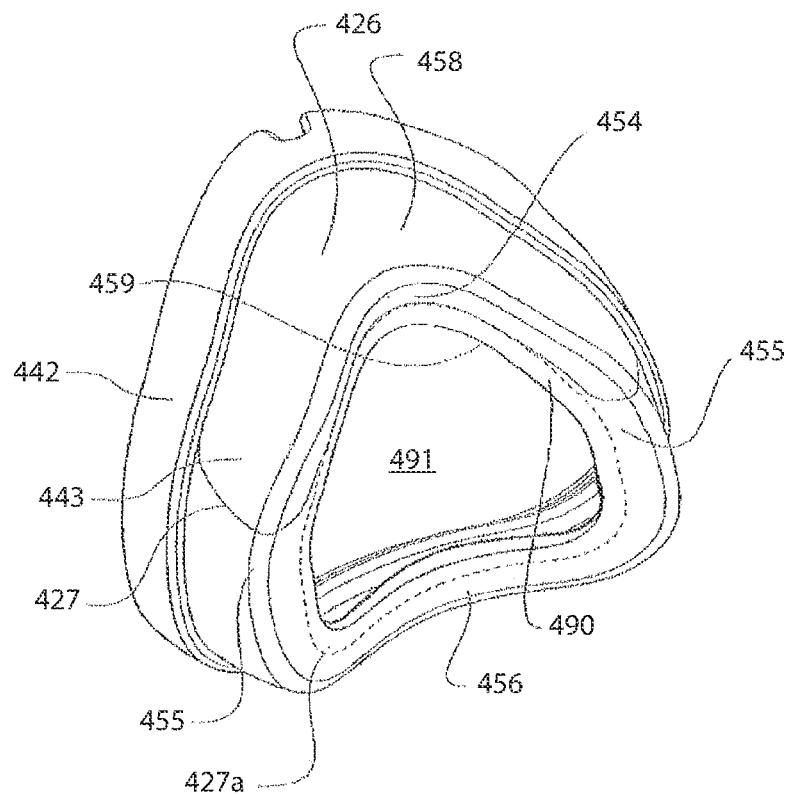
FIG. 36 a is a perspective view of the mask seal assembly of the patient interface of FIG. 34 and FIG. 35, the mask seal assembly comprising a seal and a seal clip.
Figure 36B:
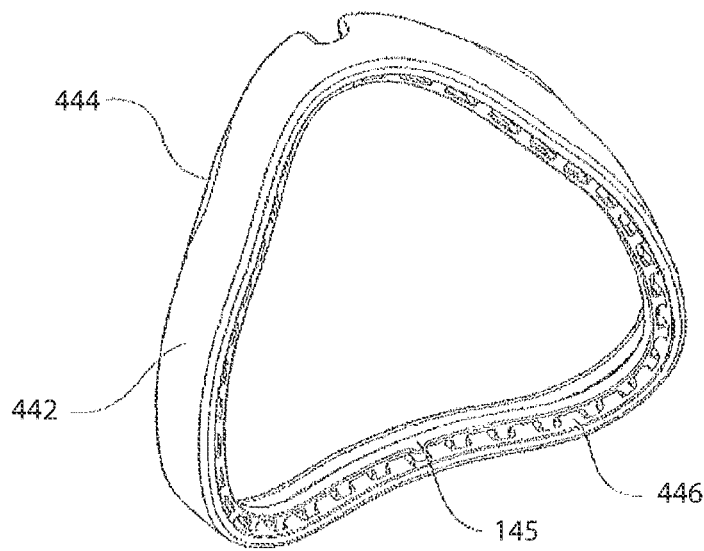
Figure 38:
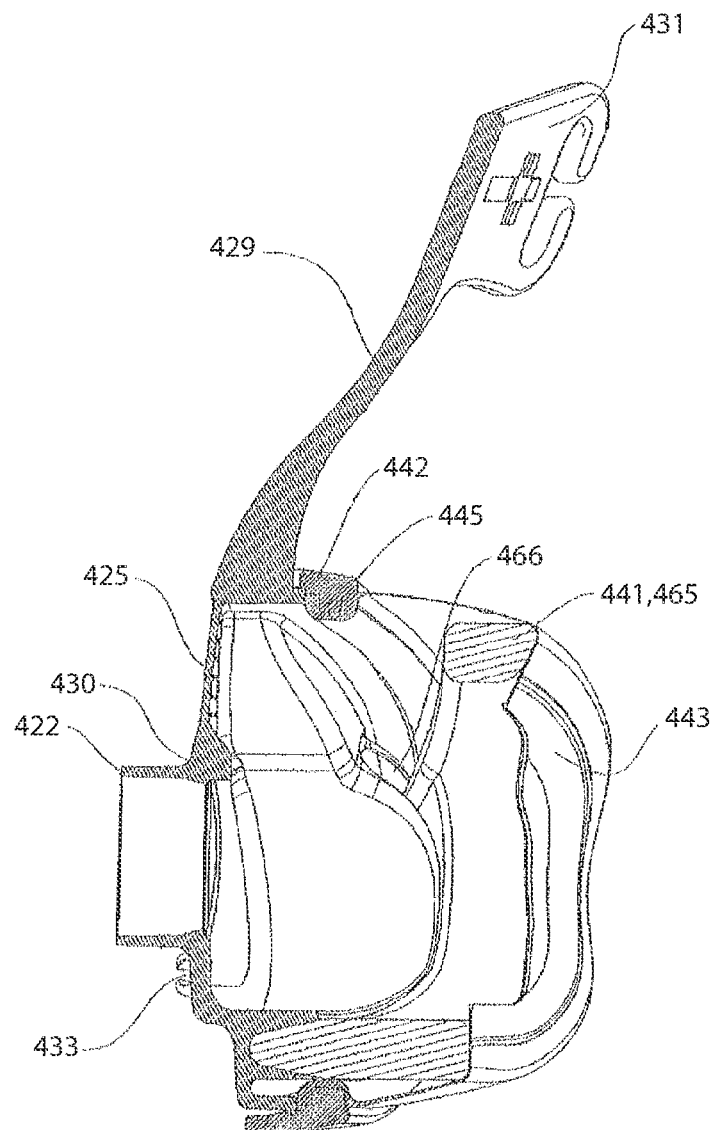
FIG. 38 is a sectional view on line X-X of the patient interface of FIG. 34.
Figure 39A:
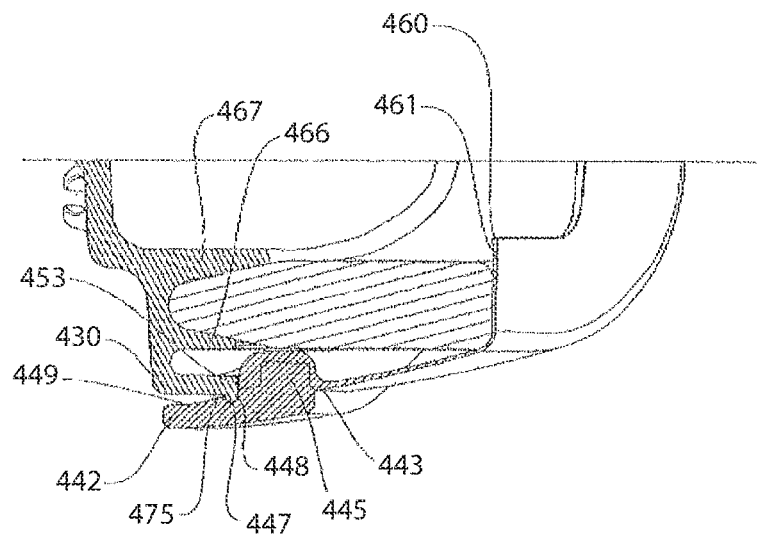
FIG. 39 a is a part sectional view on line X-X showing a preferred form of the interface arrangement between the mask body and the mask seal assembly of the patient interface of FIG. 34.
Figure 39B:
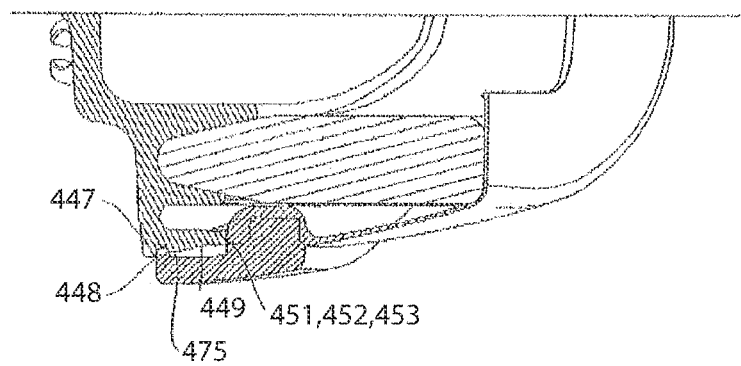
Figure 39C:
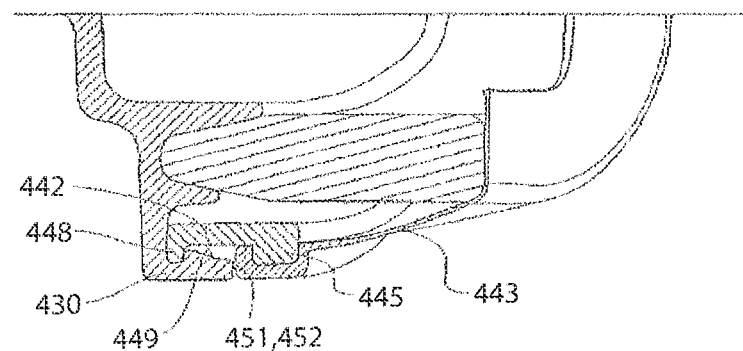
Figure 39D:
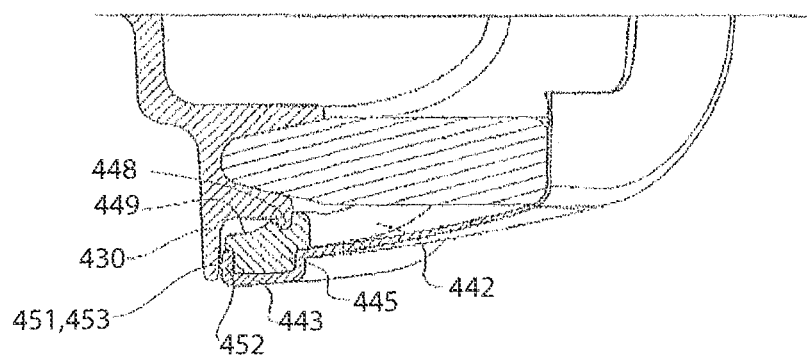
Figure 39E:
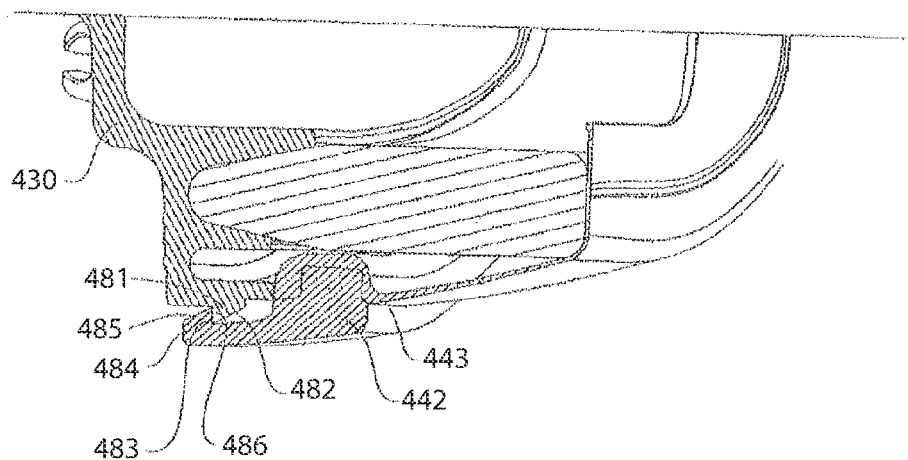
Figure 40B:
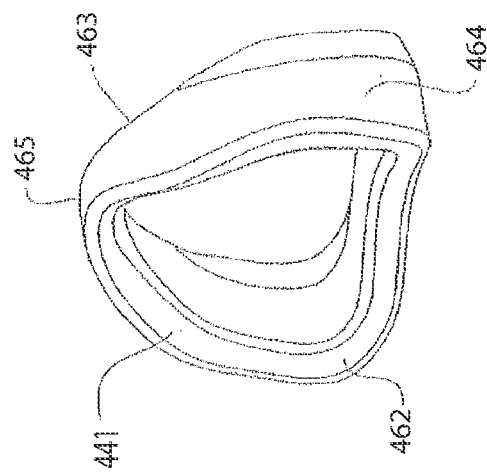
FIGS. 40 a and 40 b are perspective views of the mask cushion of the patient interface of FIG. 34.
Figure 40A:
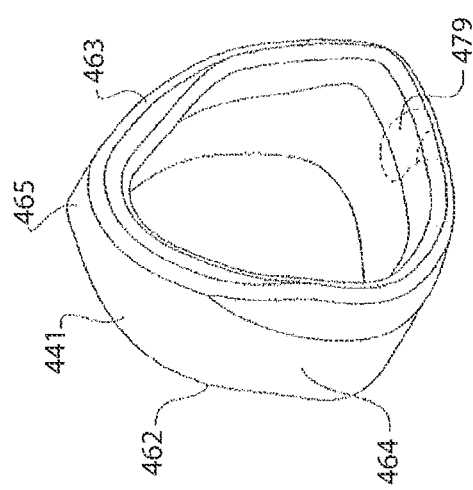

In the preferred form, the seal assembly 440 comprises a flexible seal 443 attached to a relatively rigid plastic clip 442, as shown in FIG. 36 a. Preferably the flexible seal 443 is permanently attached to the plastic clip 442 so that the seal assembly 440 forms a single, item of the mask assembly 402.

In the preferred form, the seal 443 is over-moulded to the plastic clip 442. The plastic clip has a series of holes 446 around its perimeter. During manufacture, over moulding of the seal to the clip causes the seal material to flow through the series of holes 446. During manufacture, the seal material is cured. Once cured, the seal 443 is mechanically linked to the plastic clip 442 via holes 446, providing a mechanical joint between the clip and the seal. In the preferred embodiment, the holes 446 are located through a raised ridge 445 running around the inside perimeter of the clip. Preferably the raised ridge 445 and holes 446 are located on a inside surface of the clip, so that the mechanical bond is located on the inside of the clip, with the joint between the clip 442 and the seal 443 visible as a simple butt joint on the outside surface of the seal assembly 440.

In alternative embodiments, the raised ridge 445 may be located on the outside perimeter of the clip, as shown in FIGS. 39 c and 39 d.

Alternatively, the seal 443 may be chemically bonded to the plastic clip. Chemical bonding may be used in combination with the mechanical bond described above.

Alternatively, the seal 443 could be glued to the plastic clip 442 with an appropriate adhesive, or the seal could be mechanically fixed to the clip. For example the seal could be sandwiched between the clip and a flange, with screws or other mechanical fixings securing clip and the flange together, with the seal sandwiched in between. This type of mechanical fixing could be permanent, or the fixings, such as screws, may allow the seal to be dismantled from the plastic clip.

Alternatively, the seal 443 could be assembled to the clip 442 in a press fit arrangement. The press fit may allow the seal 443 to be attached to and detached from the seal clip 442 many times. Alternatively, the press fit may be a permanent connection of the seal 443 to the clip 442.

The clip 442 forms a rigid perimeter for the seal assembly 440, the clip 442 being rigid relative to the seal 443. The clip provides a rigid interface extending the full perimeter of the seal assembly or at least substantially the full perimeter of the seal assembly.

The interface between the rigid clip 442 and the rigid mask body 430 provides a positive engagement between the seal assembly 440 and the mask body 430. This positive engagement provides an improvement over prior art masks that have a flexible seal interfacing directly to a mask body. The face seal assembly of the present invention may be easily and quickly assembled and disassembled to and from the mask body in a single engagement action. A flexible seal to mask body interface requires a comparatively more difficult seal to body engagement, as discrete portions of the seal must be fitted one at a time to the mask.

Preferably the seal assembly clip 442 and mask body 430 are made from polycarbonate, nylon, acetyl or other similar rigid plastic.

Alternatively, the seal assembly clip 442 and mask body 430 could be made from a semi-rigid material such as a thermoplastic elastomer, silicone rubber or urethane, or other similar semi-rigid material. Preferably the semi-rigid material has a Shore-A hardness of 60 or higher.

The clip 442 is shaped to match the shape of the back perimeter region 452 of the mask body 430. The clip 442 may only be attached to the mask body in a single orientation. It is therefore not possible to attach the seal assembly 440 to the mask body 430 incorrectly.

The clip 442 attaches to the mask body in a 'clip' or 'snap' type engagement. A series of blimps 448, or raised portions, on the mask body 430 interact with corresponding recesses 447 on the clip 442, to hold the clip 442 in place on the body 430. For example, for a mask that has a substantially equilateral perimeter with three sides, three recesses 447 may be located on the inside surface of the clip, the recesses being spaced apart, one recess being located on each side of the equilateral perimeter. The mask body, being correspondingly shaped to match the seal assembly clip, has three corresponding bumps 448. As the clip 442 attaches to the mask body, interference between the clip and each mask body bump 448 causes the clip or the mask body, or both, to deflect to a deflected condition until each bump 448 reaches a corresponding recess 447, Once the clip has been fully engaged with the body, each bump 448 locates within a corresponding recess 447, and the clip or body, or both un-deflect from the deflected condition to an un-deflected or partially deflected condition, the parts being clipped or snapped together in a fully engaged position. Preferably the clip or the mask body or both remain in a slightly deflected condition when fully engaged together.

The recesses 447 may be formed by having a second series of bumps on the clip, each recess effectively created, by a rear shoulder of a bump. In this arrangement, interference between bumps on the clip and bumps on the mask body occurs until the clip bumps and the mask body bumps pass to sit adjacent one other in an engaged position As best shown in FIGS. 39 a and 39 d, the clip 442 preferably has a relatively long lead in, or ramped profile 449, leading to the clip recess 447. This lead in section preferably extends the full inside perimeter length or substantially the full inside perimeter length of the clip 442. Preferably the lead-in section extends at least 50% of the full perimeter length of the clip.

Preferably each recess 447 is located immediately behind the lead-in section. The lead-in section assists with the attachment of the clip to the mask body. The clip 442 or mask body 430, or both, are gradually deflected over the length of the lead-in section until the apex 475 of the lead-in section and each mask body bump 448 pass each other. Once the bumps 448 have passed over the lead-in section, the bumps 448 locate within each corresponding recess 447, such that there is little or no interference between the two parts 430 and 442. The two parts un-deflect in a relatively sudden snap action compared to the gradual deflection caused by the lead, in section 449 during engagement. This arrangement provides a positive, single engagement action. The positive single engagement action provides the user with assurance that the seal assembly has been correctly fitted to the mask body. The clipping arrangement preferably generates a clipping sound as the bumps 448 located into the recesses 447. The clipping sound provides reassurance to the user that the clip has been correctly fitted to the mask body. The seal assembly 440 may be attached to and detached from the mask body 430 many times.

Alternatively, the lead in section, or ramp, described above may be provided on the mask body, as shown in the alternative embodiments of FIGS. 39 b and 39 c.

The lead in or ramped section 449 has a length to height ratio of approximately 3 to 7. In the preferred embodiment the lead in section has a length to height ratio of around 5. That is, for a ramp length of around 5 mm, the ramp height is around 1 mm. The lead in section ratio is best identified in FIG. 43, where the ramp length B is around five times the ramp height A.

The ramp section results in a seal clip cross section with a relatively high width to height ratio. The cross section of the preferred form of the seal clip has a width to height ratio of around 2. Once the seat 443 is attached to the clip 442, the cross section of the seal assembly 440 at the seal clip has a width to height ratio of around 1.5-2, with the shorter dimension transverse to the direction in which the clip is engaged to the mask body. Preferably this ratio is around 1.8.

In the preferred embodiment of FIG. 39, and in die alternative embodiments of FIGS. 39 b and 39 d, the clip 442 interfaces with the mask body such that the clip engages to an outwardly facing surface of the mask body. However, in the alternative embodiment of FIG. 39 c, the clip 442 interfaces to an internal or inwardly facing surface of the mask body.

A series of bumps 448 and recesses 447 around the perimeter of the mask body and clip have been described above. The bumps and recesses are located so that the seal assembly may be disengaged from the mask body by squeezing the sides or opposite perimeter portions of the clip, to deflect the clip and disengage the bumps 448 from the recesses 447. To disengage the clip from the mask body, opposite perimeter portions of the clip are squeezed at positions where bumps 448 are absent, allowing the clip to deflect, to 'pop' the bumps out of the corresponding recesses. Given the ratio of the seal assembly cross section at the clip, as described above, the clip is relatively thin transverse to the direction in which the clip is engaged to the mask body. The thin clip is relatively easy to deflect by squeezing the opposite perimeter portions in a direction transverse to the direction in which the clip engages to the mask body, to easily deflect the clip from the mask body.

Alternatively, a continuous bump extending fully around the mask perimeter may be utilised to provide the snap interface between the seal assembly 440 and the mask body 430. In this configuration, the bump may not have a constant height all the way around the mask perimeter. Having a continuous bump with different heights may allow the clip to be disengaged front the mask body by squeezing the sides or opposite perimeter portions of the clip, to deflect the apex 475 of the lead in section 449 of the clip 442 past a corresponding higher portion of the continuous bump.

Alternatively the clip 442 may have a continuous recess passing around the full perimeter or substantially the full perimeter of the clip, the recess being located immediately behind the lead-in section 449, the mask body bump 448 passing over the lead in section before clipping into a portion of the continuous recess.

In alternative embodiments such as the embodiments shown in FIGS. 39 b and 39 c, the recesses 447 may be provided in the mask body 430, and the corresponding bumps may be formed on the mask clip 442.

The face seal assembly 440 may include at least one wing portion 444 to assist a user to disengage the face seal assembly from the mask body. The wing portions 444 provide a gripping flange to pull the clip 442 away from the mask body 430.

In a further alternative embodiment, the clip may be clipped to the mask body in a permanent engagement. With reference to FIG. 39 e, the mask body 430 has a series of protrusions 481. Each protrusion has a ramped surface 482 and an abutment surface 483. For each body protrusion 481, the mask clip 442 has a corresponding protrusion 484, each mask clip protrusion having a ramp surface 485 and an abutment surface 486. Alternatively, a single continuous protrusion 481 may pass around the perimeter of the mask, with a corresponding continuous protrusion 484 passing around the perimeter of the clip. During an assembly process, the seal assembly clip 442 is interfaced to the mask body in a pressing operation, the mask body and mask clip are pressed together. The mask body, or the mask clip, or both deflect as the ramp surfaces 482 find 485 contact, and slide past one another. Once each mask body protrusion 481 and mask clip protrusion 484 pass each other, mask body 430 or clip 442, or both, return to an un-deflected or partially deflected condition, and mask body protrusion abutment face 483 abuts against clip protrusion abutment face 486, retaining mask, body 430 and clip 442 together. The abutment faces 483 and 486 are aligned substantially laterally relative to the direction in which the clip and body are pressed together. With the abutment faces arranged laterally, or substantially perpendicular to the pressing direction, the clip 442 may not be removed from the mask body easily, creating a substantially permanent joint between the clip and the body.

This alternative embodiment is useful for disposable masks that are disposed of after a single use. Such an embodiment is useful in simplifying the manufacturing process. During manufacture, moulding the seal 443 to the seal clip 442 may be easier than moulding the seal 443 directly to the mask body 430. Once the seal is moulded or attached to the seal clip as in any of the embodiments described above, the subsequent operation of pressing the clip 442 and mask body 443 together is a relatively simple assembly operation.

As best shown, in FIG. 37 and FIG. 39 a, the seal preferably has a bearing surface 451 extending around the perimeter of the clip. The seal bearing surface 451 feces a corresponding bearing surface 452 on the mask body. The seal bearing surface and the mask bearing surface are in contact when the seal assembly is attached to the mask body in a butting engagement. When the seal assembly 440 is attached to the mask body 430, the seal 443 at tire bearing interface is compressed so that a scaling interface is formed between the seal assembly and the mask body. Preferably, the clip has a raised ridge 445 running around the inside perimeter of the clip. The seal 443 is compressed by being squashed between the raised ridge 445 and the mask body bearing surface 452 when the seal assembly 440 is attached to the mask body 430.

To assist with creating a good seal between the seal assembly and the mask body, a continuous rim 453 may be provided on the seal bearing surface 451. The rim provides a small contact area in contact with the mask, body bearing surface 452. The small contact area allows a relatively high compression of the rim, and therefore effective seal, for a relatively small seal assembly to mask body engagement force.

Profiled Seal Clip

The seal 443 is shaped to approximately match the facial contours of a user's face. For the preferred form of the nasal mask shown in FIGS. 34 to 38, the face seal is contoured to approximately match the facial contours of a user around the user's nose, from the bridge of the nose, continuing down the cheek regions adjacent each side of the user's nose and across the user's philtrum area. In particular, there is an indented section 454 intended to fit over the bridge of the patient's nose, a cheek contour 455 on each side to follow the cartilage extending from the middle of the user's nose, and an indented section 456 to seal around the philtrum area of the user.

The present shape of the seal is chosen to 'approximately match' the facial contours of a range of users. To approximately match tire contours of a user's face, the seal is contoured in three dimensions, that is, shaped to fit around a user's nose, and contoured in a direction substantially normal to a user's face, as described above and shown in the accompanying figures.

Similarly, if the invention was applied to a full face mask covering a user's nose and mouth, the face seal would be shaped to approximate the facial contours of the user's chin and wider check regions.

Figure 42:
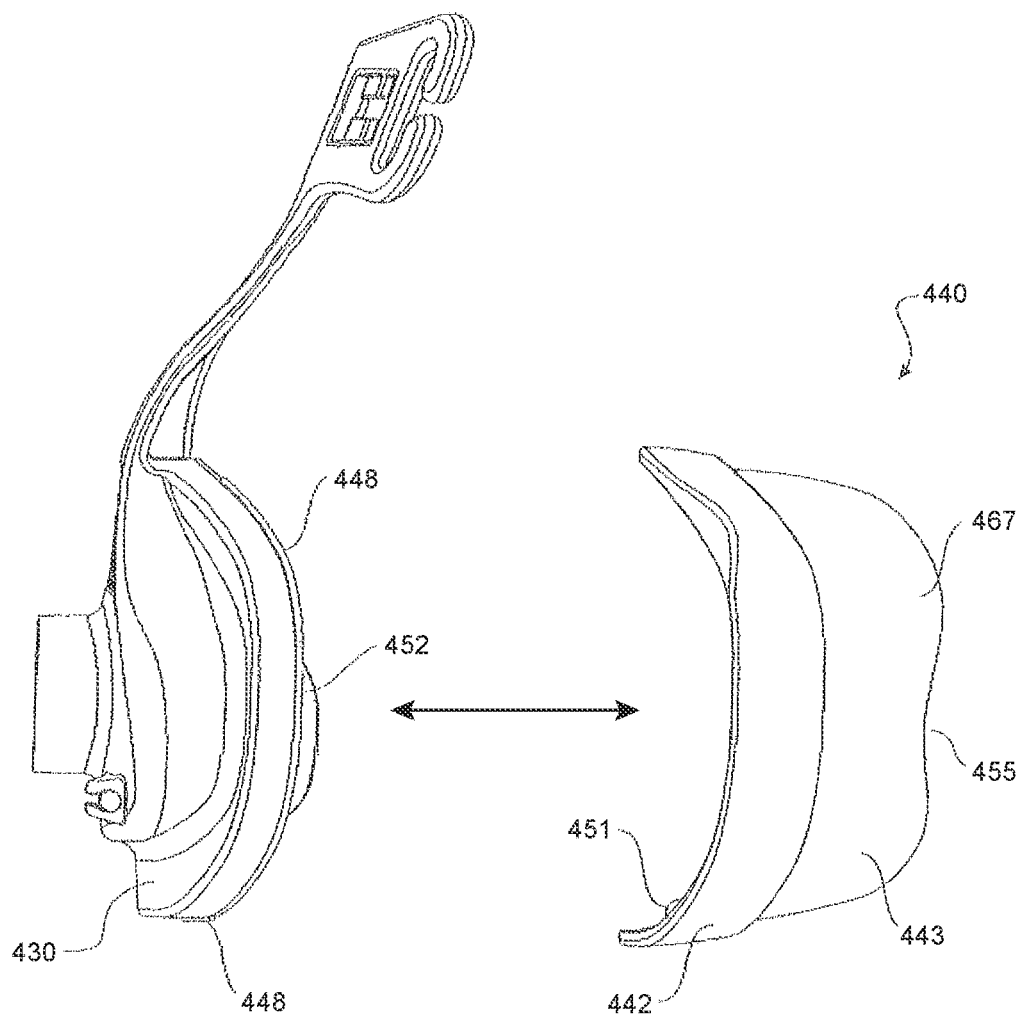
FIG. 42 is a side view of the mask body and the mask seal assembly of FIG. 34.
Figure 45A:
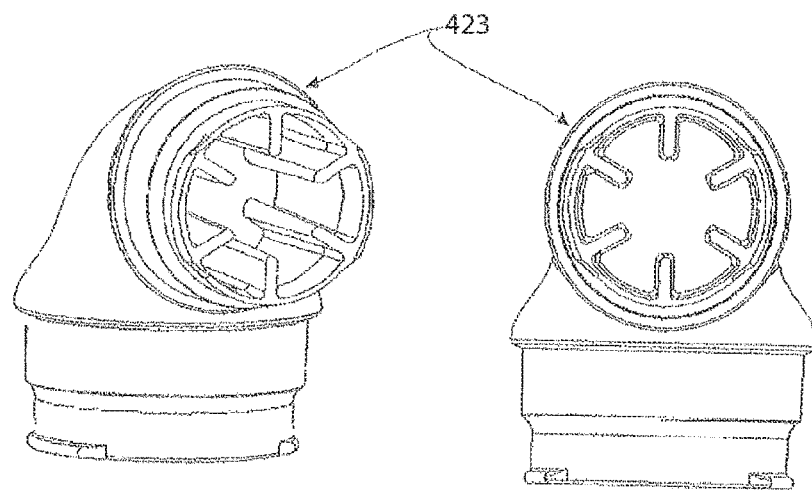
FIGS. 45 a and 45 aa show a perspective view and a rear view of a first alternative form of connector for connecting a conduit to the mask assembly of FIG. 34, the connector incorporating radial baffles extending from the circumferential edge of the connector partway towards the centre.
Figure 45B:
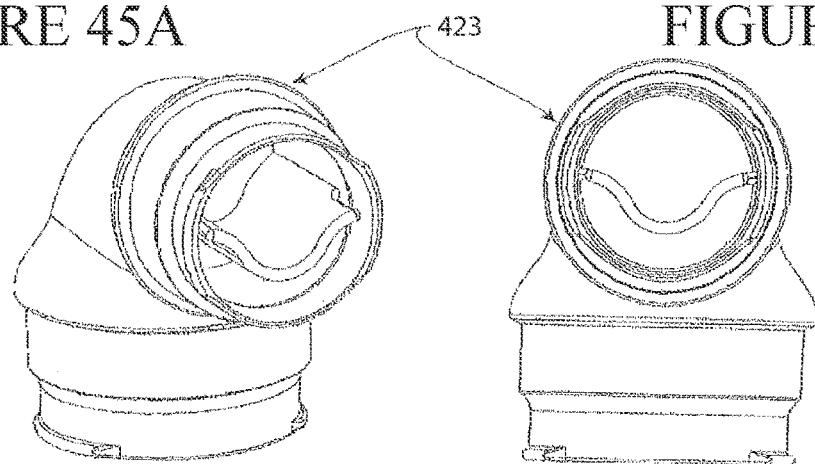
Figure 45C:
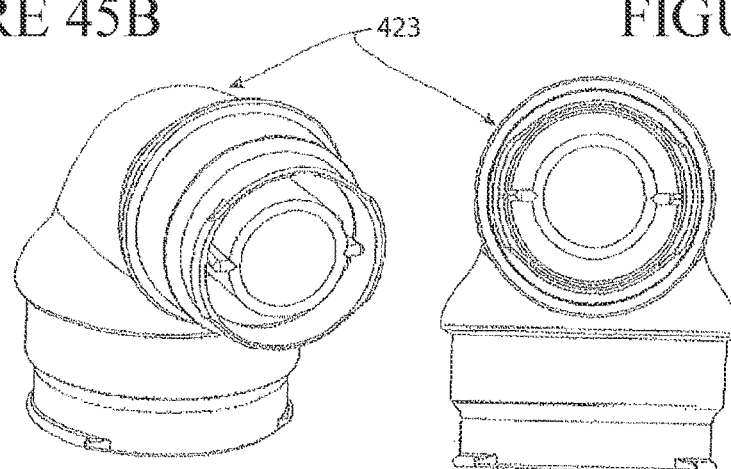
Figure 45D:
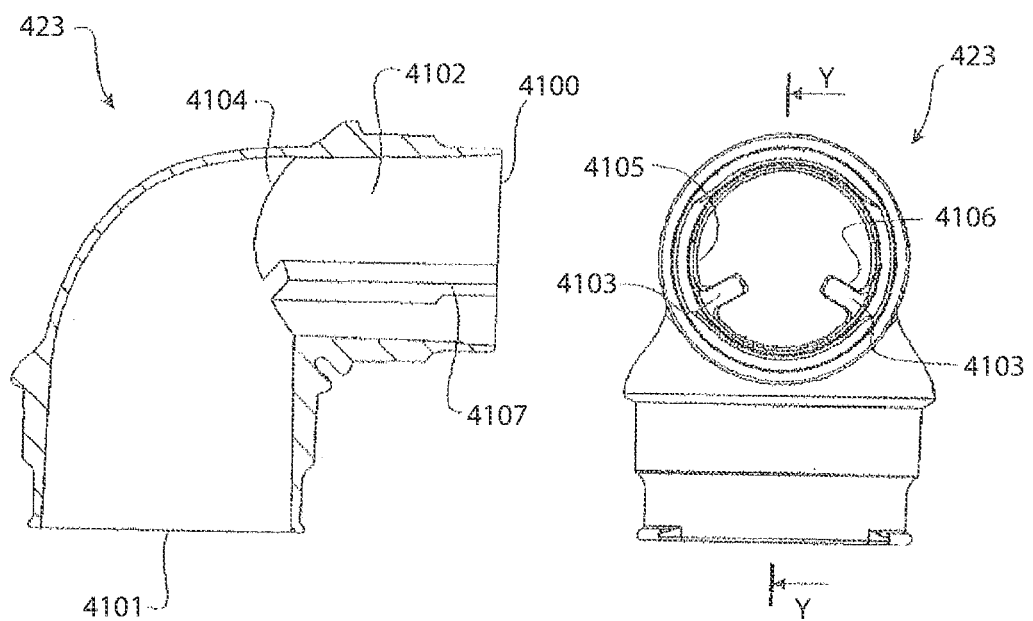

As best shown in FIG. 42, the seal, assembly clip 442 and the rear portion, or back edge 452 of the mask body are shaped to generally follow the contours of the user's face. Shaped to 'generally follow', means that the contoured shape of the portion of the seal in contact with a user's face is generally replicated in the shape of the clip. The profile of the clip and the profile of the seal in contact with the user's face are therefore similar. The main difference in the shape of the clip and the shape of the portion of the seal in contact with the user's face is that the shape of the clip does not include the indent 455 in the cheek contour portion of the seal, the shape of the clip being flatter in this region. The profiled clip allows the walls 457 of seal assembly 440 to have a generally constant depth around the circumference of the seal 443. Preferably the wall depth varies by less than around one third of the deepest wall depth. A generally constant wall depth helps the seal to apply even pressure to the face around the circumference of the seal. The profiled seal clip 442 and mask body 430 also helps to minimise the size of the mask assembly. Minimising the size of the mask is an important feature for a comfortably fitting mask. A small size provides a lightweight mask that is more comfortable to wear and less obstructive to the user.

A profiled seal assembly clip 442 and a corresponding profiled mask body 430 provides the additional benefit that a small amount of misalignment may be corrected when fitting the seal assembly to the mask body due to the shape of the parts. For example, the inventors have found that the profiled shape of the clip and mask body, combined with the ramp section 449 that extends the full perimeter length or substantially the full perimeter length of the clip, automatically corrects an angular misalignment of approximately 5 degrees when engaging the clip to the mask body. When pushing the clip and body together, misalignment is corrected as a portion of the mask body contacts the lead in section 449 of clip 442. For example, given a small amount of angular misalignment between the clip and mask body, the initial contact between the clip and lire mask body occurs at a first position on one side of the nasal bridge region of the mask body and at a second position on the mask body diametrically opposite the first position. The two positions of the mask body in contact with the clip are angled partially in line with the direction in which the clip is engaged to the mask body. As engagement force is applied to the clip and mask body, the angled shape of the clip and mask body causes the clip and the mask body to slide into alignment until the clip and mask body snap together. In prior art masks with a planar interface between the mask body and seal clip, the interface between the clip and the mask body is transverse to the direction in which the clip engages to the mask body; the seal clip and the mask body must be accurately aligned in order to correctly fit the clip to the body.

Inflatable Seal

Preferably the seal 443 includes a thin region 426. The thin region 426 is a region formed in the seal 443 which is thinner than the remainder of the cross-sectional thickness of the seal 443. In the preferred embodiment the thin region is in the nose bridge region, the extent of which is indicated by line 427 in FIG. 36 a. The thin bridge region 426 is shown to extend approximately halfway down the sides of the seal from the apex 458. Alternatively, the thin region 426 may extend around the perimeter of the seal 442, as indicated by line 27 a in FIG. 36 a.

In particular, the edge portion 490 must be thicker than region 426 so as to provide strength to prevent the seal losing its shape under typical CPAP pressures. The seal thickness is also thicker al the interface between the seal 443 and the clip 442, to provide strength in the joint between the seal 442 and the clip 442.

For example, the thick portions of the seal may have a thickness of around 0.3 to 0.6 mm. The thin region has a thickness that is in the range of around 20-80% of the thickness of the rest of the seal, that is, a thickness of around 0.05 mm-0.5 mm. Preferably the thin section is ultra thin with a thickness of around 0.05 mm-0.2 mm. In the preferred embodiment, the ultra thin region reduces the pressure on a patient's nose in the nasal bridge region, compared to when a seal does not have any reduced thickness section. Furthermore, a thin region 426 in the seal 443 allows for different sized patient's to comfortably use the mask and seal of the present invention.

In use, when a force is placed against the seal 443 the thin region 426 will yield more than tire rest of the seal 443. Therefore, this region 426 is more flexible and allows for added patient comfort.

In addition to being more flexible, due to the thin region being so thin, in the preferred embodiment the thin region 426 inflates as the CPAP pressure is applied to the mask.

Prior art masks include seals that inflate under typical CPAP pressures. However, prior art nasal masks inflate to a preformed shape or a displaced preformed shape. The preformed shape is loose when not in use. In use, the loose shape fills with air or gases and is supported in die preformed shape or a displaced preformed shape by the air or gases at positive pressure being supplied by the CPAP system. The prior art mask seal does not inflate to an elastically stretched state significantly larger than the molded or formed shape of the un-pressurized seal. For example, prior art mask seals include a bellows section which is loose when not in use. When in use, the bellows section fills up with air. The seal material of the bellows section is not significantly stretched, as the material thickness of the bellows section does not allow for significant elastic stretch under normal CPAP pressures, the material of the bellows section being too thick.

Figure 46:
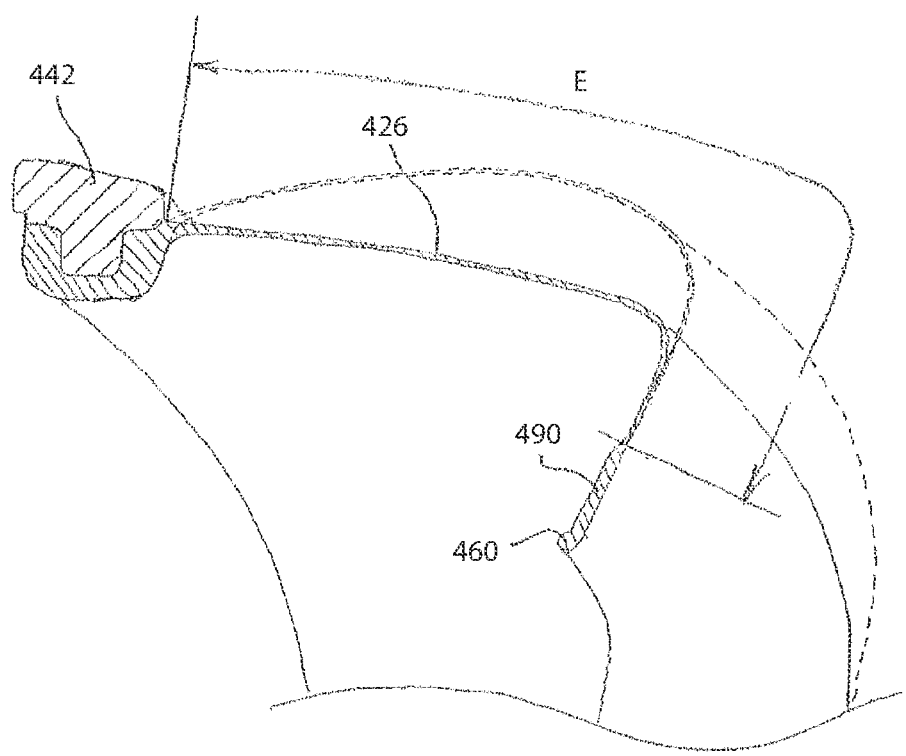
FIG. 46 is a part sectional view of the mask seal assembly showing the seal in an un-pressurised state and a pressurised elastically stretched state.

In the preferred embodiment of the present invention, the ultra thin section 26 inflates under CPAP pressure to an elastically stretched state significantly larger than the molded or formed shape of the seal. The ultra thin region provides a seal that remains tight, with no loose sections that may crimp or fold, when un-deflated. Inflation by typical CPAP pressures to a significantly stretched state helps the sealing performance of the mask, as the seal elastically inflates to the facial contours of the user's face and allows for more movement of the mask on the user's face. The ultra thin region 426 inflates to an elastic stretch condition under typical CPAP pressures of 4 cm-25 cm $H_2O$ head. The seal of the present invention includes a thin region that inflates under typical CPAP pressures to an elastically stretched condition with strain in the thin region greater than 0.1. That is, the length E of the thin region as shown in FIG. 46 increases by at least 10% when pressurized under normal CPAP pressures. In FIG. 46, seal 443 drawn in continuous line type shows the thin region 426 un-pressurized. The dashed lines show the seal 443 pressurized, with the thin region 426 pressurized to a significantly stretched condition, with an elastic stretch of approximately 10%. Preferably the thin region inflates under typical CPAP pressures to an elastically stretched condition with strain in the thin region greater than 0.2.

The seal is typically formed during manufacture by injection molding. Such a thin region has been achieved in manufacture by injecting the seal material into a closed seal mold via the thin region 426. Having the injection point within the thin region allows better control of the seal forming process and allows the ultra thin region to be formed successfully. Injection via the thin section is preferred.

The thickness figures provided above are preferable for silicone with a shore A hardness of approximately 40. If an alternative silicone or other rubber material with similar properties to silicone is used, the thickness figures should be adjusted. The thickness figures may be adjusted inversely proportionally with respect to the hardness or elasticity of the material. For example, for a material with a Shore A hardness of 20, the seal thickness may be twice as thick as the figures provided above.

As best shown in FIG. 36 *a*, the thin region 426 on the seal 443 preferably does not extend completely to the outer edge 459 of the seal 443, but grows in thickness in region 490. This is because the outer edges of the seal 459 when thicker are less prone to tearing. Also thicker region 490 provides structural support to the seal 443 so that seal 443 maintains its perimeter length in contact with the user's face when inflated, the perimeter length extending around the seal opening 491.

In additional, as shown in FIG. 39 *a*, the seal preferably has a bead 460 on the perimeter edge of the seal surrounding the seal opening 491. Preferably this bead is formed at the inside surface 461 of the seal. The diametrical cross-section of the bead will typically be in the range 0.4 mm-1.0 mm. Preferably the bead diameter will be about 0.5 mm. The bead provides additional strength to the edge of the seal, to add additional strength and support at the perimeter of the seal opening 491 and reduce the likelihood of the seal being torn if the seal is inadvertently caught or snagged by a foreign object.

Alternatively, the seal 443 may be molded without an opening. Opening 491 is then cut out of the molded seal in a cutting operation, following the molding process. The opening 491 may be cut with a knife or press in the cutting operation. The cutting operation results in a clean edge which is less susceptible to tearing compared to a molded edge. For a seal manufactured in this way, a bead 460 is less important.

An inflatable seal may also be incorporated into the mask embodiment of FIG. 23. For example, thin region 203 could have a thickness of around 0.05 mm to 0.2 mm, so that this region inflates under typical CPAP pressures to an elastically stretched state, as described above in relation to the embodiment of FIG. 36 *a*.

As shown in FIG. 24, the length 217 of the thin region increases by at least 10% when pressurised under normal CPAP pressure. The stretched pressured seal is indicated by the dashed fines 216. The edge portion 209 of seal 201 is thicker than region 203 so as to provide strength to prevent the seal losing its shape under typical CPAP pressures. The seal thickness is also thicker at the outer edge 211 as described earlier to provide strength in this area of the seal.

Mask Cushion

The mask assembly of FIG. 34 preferably includes a mask cushion 441, as described in the similar earlier embodiment of FIGS. 21 to 23.

In the interface 402 of FIG. 34, the cushion 441 is provided around the periphery of the mask, and is surrounded by the seal assembly 440. When using a thin seal, the cushion 441 provides support to the seal assembly 440 to achieve an effective seal onto the face of the user to prevent leakage.

One end 462 of the mask cushion is shaped to match the shape of the seal in contact with the user's face, and an opposite end 463 is shaped to match the mask body.

As described above, the seal assembly clip 442 and mask body 430 generally follow the contours of the user's face, and therefore provide a generally constant seal depth between the mask body 430 and seal surface in contact with the user's face. The cushion in the preferred embodiment therefore has a wall 464 with a generally constant depth. The constant depth cushion helps to provide an even pressure to the face around the periphery of the mask.

The cushion is constructed of a resilient material, for example polyurethane foam, to distribute the pressure evenly along the seal around the patient's face. In other forms the cushion 441 may be formed of other appropriate material, such as gel, silicone, or other composite materials.

In the preferred embodiment, tire mask cushion includes a raised bridge 465 in the nasal bridge region. The raised bridge 465 can also be described as a cut out section made in the cushion, the cut out being on the mask body end 463 of the cushion. As the raised bridge 465 is unsupported by the mask body 430, it is much more flexible and results in less pressure on the nasal bridge of the patient.

In other forms, the cushion may be provided with other contours or cut outs on the mask body end 463 of the cushion, so that in the areas where there are regions cut out, the cushion is more flexible.

Preferably, the extent of the raised bridge portion 465 of the cushion substantially aligns with the extent 427 of the thin bridge section 426 of the seal described above.

The cushion 441 is located around the outer periphery of the mask body, contacting the mask body except for in the raised bridge portion 465 of the cushion. As best shown in FIG. 37, the cushion is located in a generally triangular cavity 466, the cavity continuing around the periphery of tire body, terminating at each side of the nose bridge region 467 of the mask, where the raised bridge portion 465 of the cushion does not contact the mask body 430. The cavity 466 is generally formed by two spaced apart walls 476 and 477.

The cushion 441 in the preferred embodiment is a separate item, the seal assembly 440 lining in place over the cushion to hold it in place within the mask assembly 402. Alternatively, the cushion may be permanently or releasable attached to the seal assembly 440 so that the seal, seal clip and cushion may be provided as a single assembly. The cushion may be permanently or releasable attached to the seal 443 or to the seal clip 442. Alternatively, the cushion may be permanently or releasable attached to the mask body 430.

Exhaust Holes

In use the user exhales his or her breath either via an expiratory conduit, (not shown in the Figures) or directly to the atmosphere. In use, the user may exhale a portion or his or her breath via the mask assembly, that is, back into the inspiratory side of the mask assembly. In prior art masks, exhaust holes are provided in the connector 423, to assist with flushing exhaled air from the mask assembly. In the preferred form of the patient interface, the mask body 430 has exhaust flow holes 425. The exhaust holes 425 in the mask body 430 improves the flushing of exhaled air from the assembly. The exhaust holes 425 consist of 5-50 holes, each hole with a diameter of 0.3 mm-1.5 mm.

In a preferred form the exhaust holes 425 are provided through the front of the mask body substantially perpendicular to the front of the mask body 430. Alternatively, the exhaust holes may pass through the front of the mask body at an angle, for example, angled approximately 445 degrees upwards, the outlet of the exhaust holes at the outside surface of the mask body being higher than the inlet of the exhaust holes at the inside of the mask body.

The holes may be provided directly through the mask body 430. Alternatively, the holes may be formed in a separate rubber or plastic insert, the insert being fitted to a corresponding aperture (not shown) in the mask body 430.

The exhaust holes 425 may be provided through the front of the mask body in an upper portion of tire mask body. Alternatively, the holes 425 may be provided through a side or sides of the mask body 430, in an upper portion of the mask body. Alternatively, the holes may be provided in a lower portion of the mask body, for example, adjacent a bottom edge of die mask body.

Figure 41A:
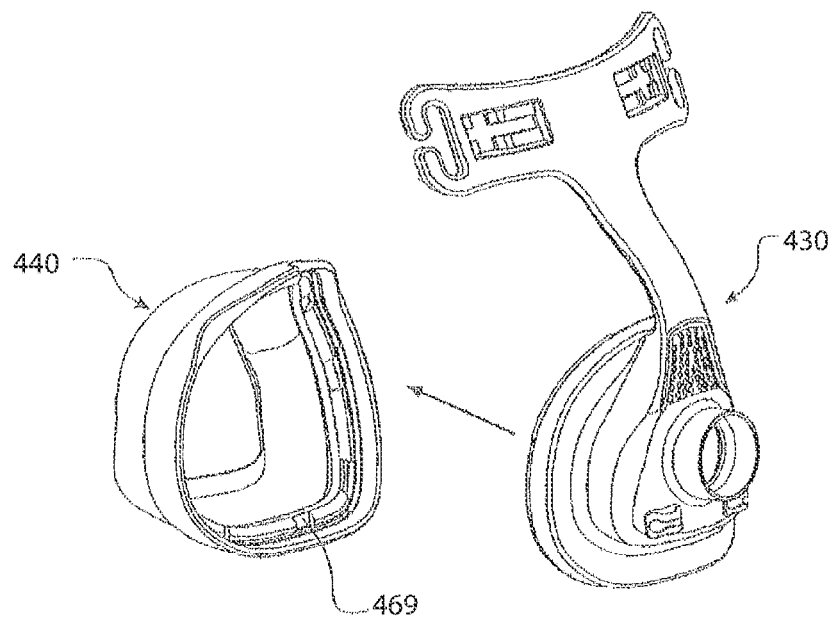
FIGS. 41 a to 41 c illustrate alternative arrangements for providing vent paths between the mask seal assembly and the mask body.
Figure 41B:
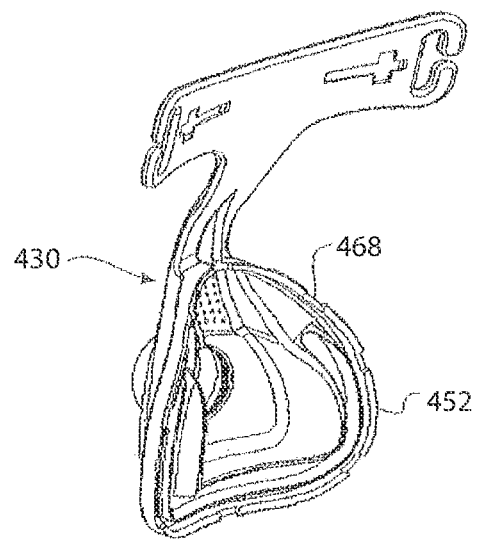
Figure 41C:
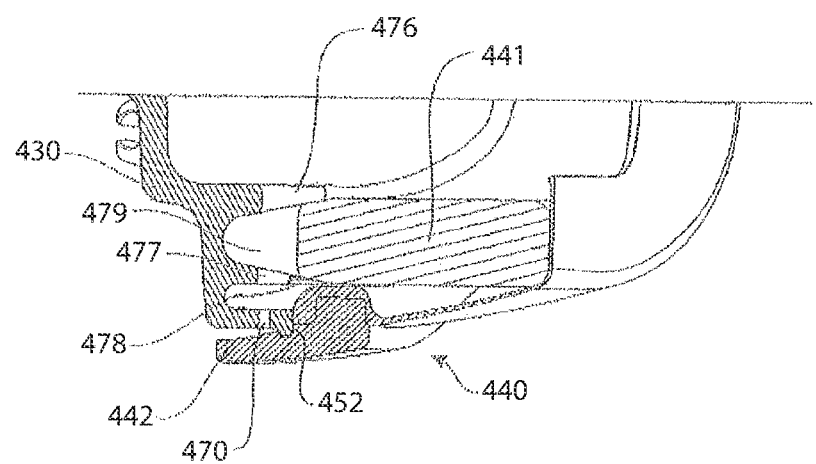

As described above, the mask body 430 preferably includes exhaust holes 425 to allow exhaled breath to be vented from the mask assembly. Alternatively, or in addition to the vent holes, the mask assembly may provide additional vent paths between the seal assembly 440 and the mask body 430, as shown in FIGS. 41 a to 41 c. The bearing surface 452 of the mask body in contact with the rim 453 or seal assembly bearing surface 451 may not extend continuously around the perimeter of the mask body. Discrete portions 468 of the rear edge of the mask body may be removed, providing a flow path from the mask assembly to the atmosphere. Alternatively, discrete portions 469 may be removed from the rim 453, or the seal assembly bearing surface 451, or both.

For clarity, discrete portions 468 and 469 have been shown enlarged in FIGS. 41 a and 41 b. In practice, the How path via either discrete portions 468 or discrete portions 469 should be similar to the flow path via holes 25, discrete portions 468 or discrete portions 469, or both, being provided in place of holes 425.

Vent paths provided by discrete portions 468 or 469 or both are visually hidden from the exterior of the mask. This arrangement provides a desirable look to the mask assembly.

Alternatively, holes 470 through the mask body 430 adjacent to the mask bearing surface 452 may be provided to vent exhaled air. Space 478 is a part annular channel space passing around the mask, the channel being formed between the mask body 430, the mask cushion 441 and the seal assembly 440. Exhaled air passes into the channel space 478 via the raised nasal bridge region of the mask. Such holes 470 provide flow paths from the mask to the atmosphere via channel space 478. Holes 470 are provided through a side of the mask body which is partially concealed by a portion of clip 442. The holes 470 are therefore partially visually hidden from the exterior of the mask assembly in use.

In order to improve venting of exhaled air from the mask, a flow path 479 may be provided directly from the interior of the mask to the vent holes 470. In this embodiment, exhaled air does not need to pass via the raised nasal bridge region and channel space 478, but may pass directly from the interior of the mask, via flow path 479 and through holes 470. Flow path 479 is provided by a cut-out region in the mask cushion 441, indicated by the dashed line in FIG. 40 a. Similar cut out portions are provided in the spaced apart wails 476 and 477 which form cavity 466. The venting of exhaled air is assisted by the downwards flow path 479, with holes 470 preferably being located in a bottom side portion of the mask, body 430. When a user nses the nasal interface of the present invention, air exhaled from the user's nostrils is exhaled substantially in line with the flow path 479 and holes 470, improving the vent flow path.

Circumferential Thin Portion

The seal 201, 443 may comprise a thin portion approximately circumferentially aligned with the circumferential perimeter of the seal. The circumferential thin portion 4200, as shown in FIGS. 47A to 47D, may extend continuously around the full circumference or perimeter of the sea). Alternatively, the circumferential thin portion 4200 may extend around only a portion of the circumference of the seal 201, 443.

The circumferential thin portion 4200 provides flexibility in the wall 457 of the seal. This flexibility can assist with allowing the seal area in contact with the users face to move laterally with respect to the mask body and head gear. Allowing lateral movement can assist with maintaining an effect seal against the user's face. The circumferential thin portion can provide a decoupling between the mask body and the area of tire seal in contact with the user's face.

Typical CPAP pressures applied to the interior of the mask assist with providing support to the seal so that the seal 201, 443 does not collapse in the region of the circumferential thin portion when pressure is applied between the seal and the users face by the head gear. The seal 201, 443 may be used with or without an inner cushion 202, 441.

Figure 48:
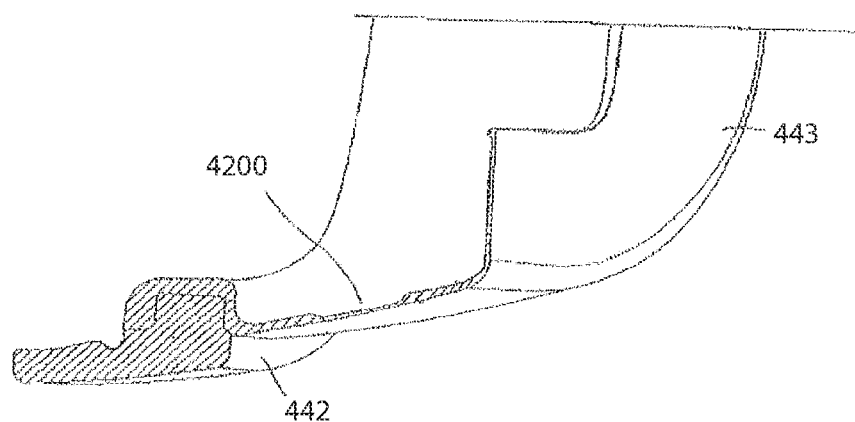
FIG. 48 is a cross sectional view of a seal assembly comprising a circumferential thin portion.

As shown in the partial cross section of FIG. 48, the thin section 4200 may be formed at an interior surface of the seal wail. Alternatively, the thin portion may be formed at an exterior surface of the seal wall, or may be formed centrally with respect to the cross section of the seal wail.

Figure 47A:
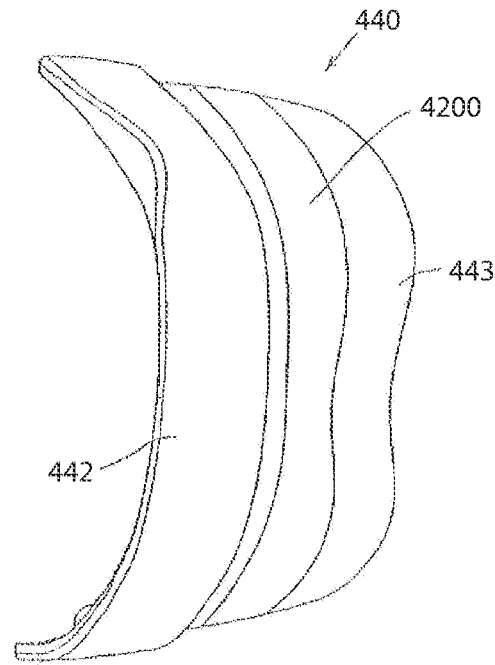
FIGS. 47A to 47F show a side view of various mask seal assemblies each comprising a circumferential thin portion.
Figure 47B:
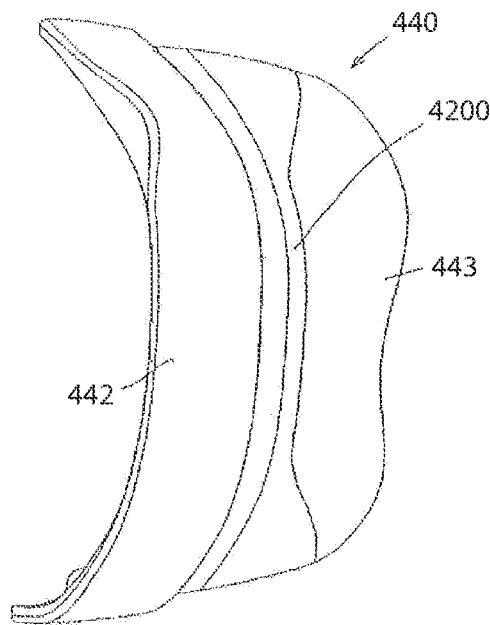

As shown in FIG. 47A, the circumferential thin portion 4200 may have approximately constant width around the circumference of the seal. Alternatively, as shown in FIG. 47B, the circumferential thin portion may comprise wide portions and narrow portions. For example, the circumferential thin portion may be wider in the nasal bridge region, or the chin region or both compared to other circumferential positions around the seal.

Figure 47C:
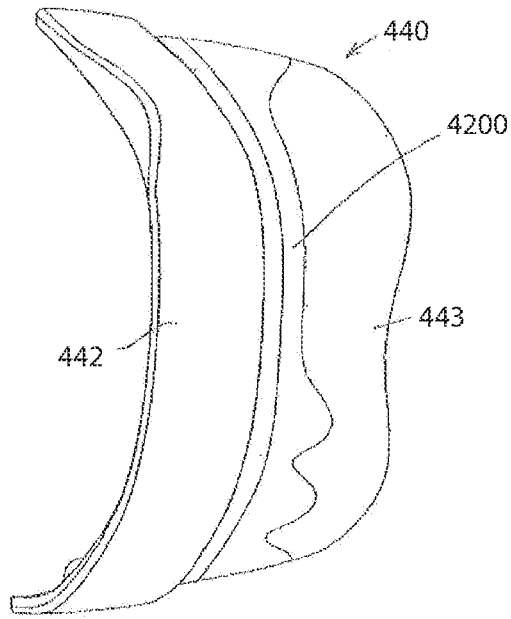
Figure 47D:
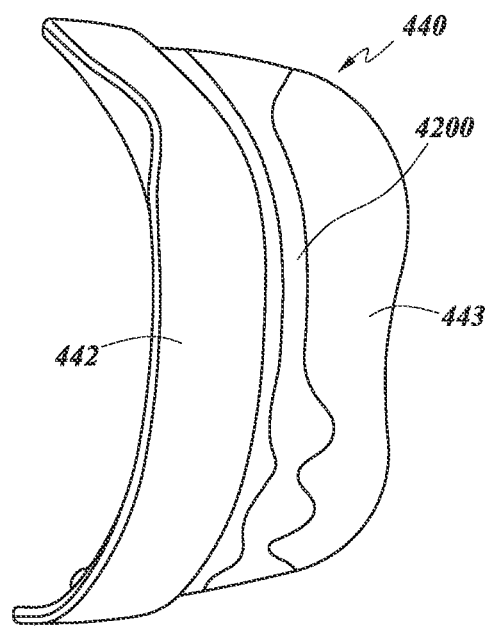

The width of the circumferential thin portion may vary at a repeating pitch around the circumference or a portion of the circumference of the seal. For example, the width may vary at a pitch between wide and narrow sections of between approximately 10 mm to 20 mm. As shown in FIGS. 47C and 47D, the width varies at a repeating pitch in the chin and lower check regions of the seal.

Figure 47E:
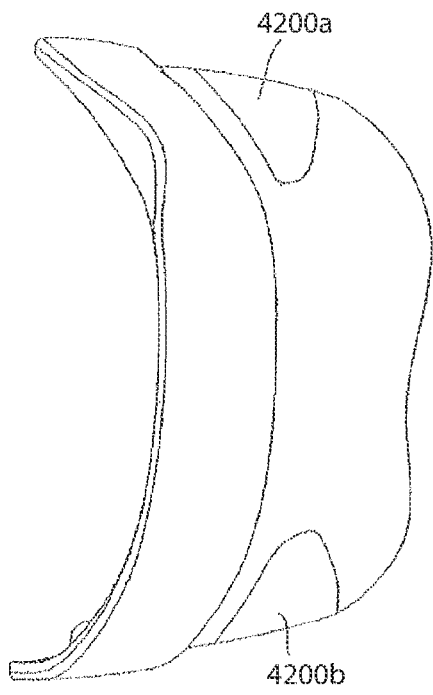
Figure 47F:
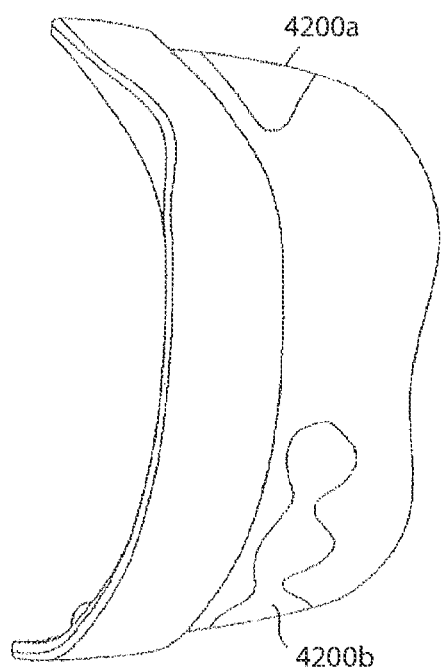

Alternatively, as shown in FIGS. 47E and 47F, the circumferential thin portion may comprise one or more thin portions 4200A, 4200B extending in a circumferential direction around the seal; thin portions 4200A, 4200B may be in the nasal bridge region or chin region or both.

A varying width circumferential thin portion may provide different facial sealing forces at different positions around the seal perimeter. For example, it is desirable to reduce the sealing force in the nasal bridge region. By widening the circumferential thin portion in the nasal bridge region, the seal 201, 443 will provide less resistance in this area against the face of a user.

The circumferential thin portion may have a thickness of approximately 0.2 mm to 0.3 mm, the other sections of the seal wall having a thickness of approximately 1 mm.

The foregoing description of the invention includes preferred forms thereof. Modifications may be made (hereto without departing from the scope of the invention as claimed.

What is claimed is:

1. A mask assembly for use as part of an apparatus for supplying a flow of respiratory gases to a user comprising:
    a flexible seal configured to seal around a nasal area of the user such that gas at positive pressure can be provided to the user, in use, the flexible seal comprising a first seal indented section configured to contact and extend across a philtrum area of the user;
a mask clip comprising:
  a first profiled shape extending about a perimeter of the flexible seal and being permanently connected to the flexible seal, the first profiled shape comprising a first plurality of contours, at least one of the first plurality of contours having a shape corresponding to the first seal indented section; and
  a plurality of mask clip connector portions, each of the plurality of mask clip connector portions comprising an inwardly facing surface facing in a radially inward direction relative to an interior of the mask assembly and a first mask clip connector protrusion positioned on the inwardly facing surface, each of the first mask clip connector protrusions comprising a first ramped surface and a first abutment surface;
a mask body comprising:
  a second profiled shape comprising a second plurality of contours corresponding to a plurality of the first plurality of contours, respectively, so as to make contact and cause the mask clip and the mask body to slide into alignment when the mask clip and mask body are moved together in an angularly misaligned orientation;
  an inlet configured to receive gases, in use, and
  a plurality of mask body connector portions, each of the mask body connector portions comprising an outwardly facing surface facing in a radially outward direction relative to the interior of the mask assembly, and a second abutment surface positioned at the outwardly facing surface;
a headgear strap attachable directly to the mask body; and
an elbow connector configured to connect to the inlet of the mask body, the elbow connector comprising a first end and a second end, the first end configured to provide a swivelable connection to the inlet of the mask body, the second end including a swivelable connection to an inspiratory conduit;
wherein the plurality of mask body connector portions and the plurality of mask clip connector portions are configured to, during attachment of the mask clip to the mask body, in use, provide a positive snap engagement and permanent connection of the mask clip to the mask body after each of the first ramped surfaces slide past respective portions of the mask body connector portions, and the first and second abutment surfaces abut against one another.

2. The mask assembly of claim 1, wherein the plurality of mask body connector portions and the plurality of mask clip connector portions are configured to, during attachment of the mask clip to the mask body, in use, cause portions of at least one of the mask body and the mask clip to deflect as the first ramped surfaces contact and slide past the respective portions of the mask body connector portions and then return to an un-deflected or partially deflected condition, with the first and second abutment surfaces abutted together.

3. The mask assembly of claim 1, wherein the mask body comprises a plurality of recesses positioned adjacent to the second abutment surfaces, respectively.

4. The mask assembly of claim 1, the second plurality of contours comprises a first angled portion at a first position and a second angled portion at a second position opposite the first position, the first and second angled portions being configured to make initial contact with the mask clip as the mask clip and mask body are moved together in an angularly misaligned orientation.

5. The mask assembly of claim 1, wherein the at least one of the second plurality of contours has a shape corresponding to said at least one of the first plurality of contours having a shape corresponding to the first seal indented section.

6. The mask assembly of claim 1, wherein the flexible seal comprises a seal shape including said first seal indented section and a second seal indented section configured to fit over a bridge of a nose of the user in use, and wherein the first profiled shape includes a second clip indented section generally replicating a shape of the second seal indented section.

7. The mask assembly of claim 1, wherein the first end comprises a first portion configured to form a ball joint with the inlet opening of the mask body, the ball joint being configured to provide the swivelable connection.

8. A mask assembly for use as part of an apparatus for supplying a flow of respiratory gases to a user comprising:
a flexible seal configured to seal around at least a nasal area of a user such that gas at positive pressure can be provided to the user, in use, the flexible seal comprising a first seal indented section configured to contact and extend across a philtrum area of the user; and
a mask clip comprising:
  a first profiled shape extending about a perimeter of the flexible seal and being permanently connected to the flexible seal, the first profiled shape comprising a first plurality of contours, at least one of the first plurality of contours having a shape corresponding to the first seal indented section; and
  a plurality of mask clip connector portions, each of the mask clip connector portions comprising a first connector surface portion, a first mask clip connector protrusion positioned on the first connector surface portion, each of the first mask clip connector protrusions comprising a first ramped surface and a first abutment surface;
a mask body comprising:
  a second profiled shape comprising a second plurality of contours corresponding to a plurality of the first plurality of contours, respectively, so as to make contact and cause the mask clip and the mask body to slide into alignment when the mask clip and mask body are moved together in an angularly misaligned orientation;
  an inlet opening; and
  a plurality of mask body connector portions, each of the plurality of mask body connector portions comprising a second connector surface portion and a second mask body connector protrusion positioned on the second connector surface portion, each of the second mask body connector protrusions comprising a second ramped surface and a second abutment surface;
a headgear strap attachable directly to the mask body; and
an elbow connector configured to connect to the inlet opening of the mask body, the elbow connector comprising a first end and a second end, the first end configured to provide a swivelable connection to the inlet opening of the mask body, the second end including a swivelable connection to an inspiratory conduit;
wherein the first mask clip connector protrusions and the second mask body connector protrusions are configured to, during attachment of the mask clip to the mask body, in use, provide a positive snap engagement of the mask clip to the mask body after the first and second ramped surfaces slide past one another.

9. The mask assembly of claim 8, wherein the first mask clip connector protrusions and the second mask body connector protrusions are configured to provide a permanent connection of the mask clip to the mask body.

10. The mask assembly of claim 8, wherein the first mask clip connector protrusions and the second mask body connector protrusions are configured to, during attachment of the mask clip to the mask body, in use, cause portions of at least one of the mask body and the mask clip to deflect as the first and second ramped surfaces contact and slide past one another and then return to an un-deflected or partially deflected condition, with the first and second abutment surfaces abutted together.

11. The mask assembly of claim 8, wherein each of the first mask clip connector protrusions comprises a first apex positioned between the first ramped surface and the first abutment surface, and wherein each of the second mask body connector protrusions comprises a second apex positioned between the second ramped surface and the second abutment surface.

12. The mask assembly of claim 8, wherein the mask clip comprises a plurality of recesses positioned adjacent to the first abutment surfaces, respectively.

13. The mask assembly of claim 8, wherein the mask clip is configured to be attached to and be detached from the mask body multiple times.

14. The mask assembly of claim 8, wherein the mask clip has at least one wing portion configured to provide a gripping flange to assist with removing the mask clip from the mask body, in use.

15. The mask assembly of claim 8, wherein the flexible seal comprises a seal shape including said first seal indented section and a second seal indented section configured to fit over a bridge of a nose of the user in use, and wherein the first profiled shape includes a second clip indented section corresponding to a shape of the second seal indented section.

16. The mask assembly of claim 8, wherein the first end comprises a first portion configured to form a ball joint with the inlet opening of the mask body, the ball joint being configured to provide the swivelable connection.

17. A mask assembly for use as part of an apparatus for supplying a flow of respiratory gases to a user comprising:
a flexible seal configured to seal around at least a nasal and oral area of the user such that gas at positive pressure can be provided to the user, in use;
a mask clip comprising:
a first profiled shape extending about a perimeter of the flexible seal and being permanently connected to the flexible seal; and
a plurality of mask clip connector portions, each of the plurality of mask clip connector portions comprising an inwardly facing surface facing in a radially inward direction relative to an interior of the mask assembly and a first mask clip connector protrusion positioned on the inwardly facing surface, each of the first mask clip connector protrusions comprising a first ramped surface and a first abutment surface;
a mask body comprising:
a second profiled shape;
an inlet opening, in use, and
a plurality of mask body connector portions, each of the plurality of mask body connector portions comprising a second abutment surface, a second connector surface portion facing in radially outward direction relative to an interior of the mask assembly and second mask body connector protrusion positioned on the second connector surface portion;
wherein the first profiled shape corresponds to the second profiled shape so as to cause the mask clip and the mask body to slide into alignment when the mask clip and mask body are moved together in an angularly misaligned orientation, in use;
a headgear strap attachable directly to the mask body; and
an elbow connector configured to connect to the inlet opening of the mask body, the elbow connector comprising a first end and a second end, the first end configured to provide a swivelable connection to the inlet opening of the mask body, the second end including a swivelable connection to an inspiratory conduit;
wherein the plurality of mask body connector portions and the plurality of mask clip connector portions are configured to, during attachment of the mask clip to the mask body, in use, provide a positive snap engagement of the mask clip to the mask body after each of the first ramped surfaces slide past respective portions of the mask body connector portions, and the first and second abutment surfaces abut against one another.

18. The mask assembly of claim 17, wherein the plurality of mask body connector portions and the plurality of mask clip connector portions are configured to, during attachment of the mask clip to the mask body, in use, cause portions of at least one of the mask body and the mask clip to deflect as the first ramped surfaces contact and slide past the respective portions of the mask body connector portions and then return to an un-deflected or partially deflected condition, with the first and second abutment surfaces abutted together.

19. The mask assembly of claim 17, wherein the first mask clip connector protrusion comprises a first apex positioned between the first ramped surface and the first abutment surface, and wherein each of the plurality of mask body connector portions comprise second ramped surface and a second apex positioned between the second ramped surface and the second abutment surface.

20. The mask assembly of claim 17, wherein the mask body comprises a plurality of recesses positioned adjacent to the second abutment surfaces, respectively.

21. The mask assembly of claim 17, wherein the mask clip has at least one wing portion configured to provide a gripping flange to assist with removing the mask clip from the mask body, in use.

22. The mask assembly of claim 17, the second profiled shape comprises a first angled portion at a first position and a second angled portion at a second position opposite the first position, the first and second angled portions being configured to make initial contact with the mask clip as the mask clip and mask body are moved together in an angularly misaligned orientation.

23. The mask assembly of claim 17, wherein the first end comprises a first portion configured to form a ball joint with the inlet opening of the mask body, the ball joint being configured to provide the swivelable connection.

* * * * *